(12) United States Patent
Martin et al.

(10) Patent No.: US 8,455,489 B2
(45) Date of Patent: Jun. 4, 2013

(54) SUBSTITUTED PYRIMIDINE COMPOSITIONS AND METHODS OF USE

(75) Inventors: Richard Martin, San Diego, CA (US); Raju Mohan, Encinitas, CA (US); Peter Ordentlich, San Diego, CA (US)

(73) Assignee: Exelixis, Inc., South San Francisco, CA (US)

( * ) Notice: Subject to any disclaimer, the term of this patent is extended or adjusted under 35 U.S.C. 154(b) by 1275 days.

(21) Appl. No.: 10/595,734

(22) PCT Filed: Nov. 9, 2004

(86) PCT No.: PCT/US2004/037642
§ 371 (c)(1),
(2), (4) Date: May 22, 2007

(87) PCT Pub. No.: WO2005/047268
PCT Pub. Date: May 26, 2005

(65) Prior Publication Data
US 2007/0293464 A1 Dec. 20, 2007

Related U.S. Application Data

(60) Provisional application No. 60/519,030, filed on Nov. 10, 2003.

(51) Int. Cl.
| | |
|---|---|
| C07D 239/34 | (2006.01) |
| A61K 31/505 | (2006.01) |
| A61P 25/00 | (2006.01) |
| A61P 25/16 | (2006.01) |
| A61P 25/18 | (2006.01) |
| A61P 29/00 | (2006.01) |
| A61P 35/00 | (2006.01) |

(52) U.S. Cl.
USPC ............. 514/247; 544/319; 514/269

(58) Field of Classification Search
USPC ................. 514/247, 269
See application file for complete search history.

(56) References Cited

U.S. PATENT DOCUMENTS

| | | | |
|---|---|---|---|
| 3,498,984 A * | 3/1970 | Santilli et al. | 544/319 |
| 3,860,596 A * | 1/1975 | Kim et al. | 544/326 |
| 4,041,030 A * | 8/1977 | Fauran et al. | 544/117 |
| 4,493,726 A * | 1/1985 | Burdeska et al. | 504/105 |
| 4,859,670 A * | 8/1989 | Kampe et al. | 514/252.19 |
| 5,026,708 A * | 6/1991 | Fujikawa et al. | 514/256 |
| 5,707,995 A * | 1/1998 | Munro et al. | 514/256 |
| 5,824,624 A * | 10/1998 | Kleeman et al. | 504/242 |
| 5,849,758 A * | 12/1998 | Kleemann et al. | 514/269 |
| 6,127,376 A * | 10/2000 | Davey et al. | 514/269 |
| 6,414,149 B1 * | 7/2002 | Chu-Moyer et al. | 544/295 |
| 6,608,066 B1 * | 8/2003 | Jiao et al. | 514/252.12 |
| 6,613,776 B2 * | 9/2003 | Knegtel et al. | 514/300 |
| 6,887,870 B1 * | 5/2005 | Ahmad et al. | 514/235.8 |
| 7,226,927 B2 * | 6/2007 | Cai et al. | 514/256 |
| 7,951,820 B2 * | 5/2011 | Bebbington et al. | 514/307 |
| 2002/0004600 A1 * | 1/2002 | Meyer et al. | 544/319 |

FOREIGN PATENT DOCUMENTS

| | | |
|---|---|---|
| DE | 24 44 426 A1 | 3/1975 |
| DE | 27 29 360 A1 | 1/1978 |
| EP | 55693 A1 * | 7/1982 |
| EP | 136976 * | 4/1985 |
| EP | 136976 A3 * | 5/1985 |
| EP | 468695 * | 1/1992 |
| JP | 63107966 * | 5/1988 |
| JP | 11158073 * | 6/1999 |
| JP | 2001139560 * | 5/2001 |
| PL | 130888 * | 9/1984 |
| PL | 164076 * | 6/1994 |
| PL | 194083 * | 4/2007 |
| WO | WO 9820003 * | 5/1998 |
| WO | WO 9823155 * | 6/1998 |
| WO | WO 0041999 * | 7/2000 |
| WO | WO 0222606 * | 3/2002 |
| WO | WO 0222608 * | 3/2002 |
| WO | 02/42280 A | 5/2002 |
| WO | WO 0242280 * | 5/2002 |
| WO | 02/47690 A | 6/2002 |
| WO | WO 2002092576 * | 11/2002 |
| WO | 2004/032716 A | 4/2004 |

(Continued)

OTHER PUBLICATIONS

Walsh, BBC News, International Version, Medical Notes, Feb. 1, 2007.*
PharmaLicensing (Mar. 2005).*
Barish, et al., Molecular Endocrinology 19 (10): 2466-2477, 2005.*
Ramsden, et al., J. Clin. Pathol: Mol. Pathol. 2001; 54:369-380.*
Tao, Hapatobiliary Pancreat. Dis. Int., vol. 6, No. 4, Aug. 15, 2007, pp. 348-357.*
Xing, et al., Schizophrenia Research, vol. 84, No. 1, May 2006, pp. 36-56.*
Dahlqvist, et al., Neuroscience, 2003;119(3):643-52.*
Lammi, et al., Mol. Endocrinol, Jun. 2004, 18(6):1546-1557.*
Cieplik, et al., Acta Poloniae Pharmaceutica (2003), 60(6), 487-492.*
Cieplik, et al., Bollettino Chimico Farmaceutico (2003), 142(4), 146-150.*
Cieplik, et al., Scientia Pharmaceutica (2002), 70(3), 245-252.*
Cieplik, et al., Archiv der Pharmazie (Weinheim, Germany) (1997), 330(8), 237-241.*

(Continued)

*Primary Examiner* — Susanna Moore
*Assistant Examiner* — Cecilia M Jaisle
(74) *Attorney, Agent, or Firm* — McDonnell Boehnen Hulbert & Berghoff LLP

(57) ABSTRACT

Novel compositions and methods of using substituted pyrimidines which have the general formula: (I).

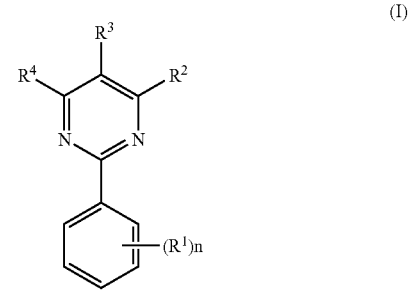

20 Claims, 18 Drawing Sheets

FOREIGN PATENT DOCUMENTS

| WO | WO 2004032716 | * | 4/2004 |
|----|---------------|---|--------|
| WO | WO 2005007143 | * | 1/2005 |
| WO | WO 2005009443 | * | 2/2005 |
| WO | WO 2005020913 | * | 3/2005 |

OTHER PUBLICATIONS

Cieplik, et al., Bollettino Chimico Farmaceutico (1996), 135(8), 459-464.*

Cieplik, et al., Farmaco (1995), 50(2), 131-6.*

Cieplik, et al., Acta Poloniae Pharmaceutica (1994), 51(1), 59-62.*

Ohkubo, et al., Chemical & Pharmaceutical Bulletin (1994), 42(6), 1279-85.*

Machon, et al., European Journal of Medicinal Chemistry (1984), 19(4), 359-63.*

Mincheva, Doklady Bolgarskoi Akademii Nauk (1980), 33(7), 925-7.*

Baker, et al., Inorganica Chimica Acta, vol. 357, # 10, Jul. 20, 2004, 2841-2849.*

Baker, et al., Dalton Trans. Jan. 7, 2005;(1):37-43.*

Zalaudek, et al., J. Am. Acad. Dermat., vol. 54, #, 1106-1107 (Jun. 2006).*

Maurasse, http://www.deepseadrilling.org/15/volume/dsdp15_24.pdf; downloaded Dec. 31, 2008.*

Malf. http://www.youtube.com/watch?v=yoNM8bBBwbE; downloaded Dec. 31, 2008.*

Ohkubo, et al., Chem. & Pharm. Bull. (1994), 42(6), 1279-85.*

El-Bahaie, et al., Pharmazie (1991), 46(1), 26-8.*

El-Kerdawy, et al., Archives of Pharmacal Research (1990), 13(2), 142-6.*

Howe, et al., J. Med. Chem. (1972), 15(10), 1040-5.*

Falch, et al., J. Med. Chem. (1968), 11(3), 608-11.*

Herrera, Tetrahedron, 59 (2003), 7331-7336.*

Sugiyama, et al., Chem. & Pharm. Bull. (1994), 42(6), 1279-85.*

Yonetoku, Yasuhiro et al, "Preparation of 4-aminopyrimidine derivatives as insulin secretion accelerators", Database CA Online, Chemical Abstracts Service, Columbus XP002328217, 2004.

Takatani, Takao et al, "Preparation of pyrimidine derivatives as drugs for treating disease and disorders of cerebral blood vessels", Database CA Online, Chemical Abstracts Service, Columbus XP002328218, 1988.

* cited by examiner

| Compound | Activity |
|---|---|
|  | C |
|  | C |
|  | C |
|  | C |
|  | C |
|  | C |

| | |
|---|---|
|  | C |
|  | C |
|  | C |
|  | C |
|  | C |
|  | C |
|  | C |

US 8,455,489 B2

SUBSTITUTED PYRIMIDINE COMPOSITIONS AND METHODS OF USE

RELATED APPLICATIONS

This application claims benefit of priority from U.S. Provisional Patent Application 60/519,030, filed Nov. 10, 2003, which is hereby incorporated in its entirety as if fully set forth.

BACKGROUND OF THE INVENTION

This invention relates to the receptors of the NGFI-B family and in particular to compounds that modulate the activity of such family members.

The nuclear receptor (NR) superfamily comprises more than 150 different proteins, most of which are believed to function as ligand activated-transcription factors, exerting widely different biological responses by regulating gene expression (for review, see Di Croce et al, EMBO J1 8:6201-6210 (1999); Mangelsdorf, et al Cell 83:825-839 (1995); Perlmann, et al, Cell 90:391-397 (1997)). Members of this family include receptors for endogenous small, lipophilic molecules, such as steroid hormones, retinoids, vitamin D and thyroid hormone.

In addition, many members of this family lack known ligands and are therefore referred to as "orphan receptors" (for review, see Giguere, et al, Endocrine Rev 20:689-725 (1999); Kastner, et al, Cell 83:859-869 (1995)). During recent years small, lipophilic ligands and activators have been identified for several orphan receptors, leading to new insights into mechanisms of metabolic and regulatory control. These findings have dramatically increased understanding of endocrinology and it's relationship to disease and offer the potential for the development of new classes of drugs able to act on previously uncharacterized signaling pathways, (for review, see Mangelsdorf et al, Cell 83:841-850 (1995); Giguere, et al., supra. Specific examples of orphan nuclear receptors which appear to be specifically regulated by ligands include, without limitation, RXR, FXR, LXR, CAR, and ROR.

In addition a number of orphan nuclear receptors exhibit high constitutive activity, or have poorly defined or lack high affinity ligand binding domains. Examples of orphan nuclear receptors within this class include members of the NGFI-B family, and SHP. Even though such receptors are unlikely to be directly regulated by ligands, interactions with other nuclear receptors, which are ligand responsive, such as, RXR, can confer upon the heterodimer complex ligand responsiveness.

Members of the NGFI-B family and their various alternate names include those listed below.

| Receptor name and Subtype | Alternative Names | Accession no. |
| --- | --- | --- |
| NGFI-B-alpha (Nur77) NR4A1 | Nur77, TR3, N10 NAK-1, TIS1 | XM_083884 |
| NGFI-B-beta (Nurr1) NR4A2 | Nurr1, RNR-1 NOT, HZF3, TINUR, TR3β | NM_006186 |
| NGFI-B-gamma (NOR-1) NR4A3 | NOR-1, MINOR, TEC, CHN | XM_037370 |

Nuclear receptors of the NGFI-B family may act on gene expression as monomers, homodimers or heterodimers (with RXR), and each of these entities can bind to different hormone response elements (HREs) and natural promoters. Hormone response elements can contain one or two consensus core half-site sequences. For dimeric HREs, the half-sites can be configured as inverted, (IR) everted (ER) or direct repeats (DR) separated by a variable number of spacer nucleotides.

For monomeric HREs, a single half site is preceded by a 5'-flanking A/T-rich sequence. Half site sequences can deviate quite considerably from the consensus sequences, especially for dimeric HREs in which a single conserved half site is usually sufficient to confer high-affinity binding to the homo- or heterodimer complexes. Naturally HREs rarely contain two perfect consensus half sites. For example NGFI-Bβ, binds to monomeric response elements (NBREs) containing the 5'-extended core motif (AAAGGTCA), and genes shown to be regulated in this manner include tyrosine hydroxylase.

The homodimer binding site consists of two inverted NBREs separated by a 6 base pair spacer and this site confers high responsiveness to gene expression in the presence of NGFI-Bα. Homodimer binding by NGFI-B α, β and γ was also observed on the pro-opiomelanocorticotropin (POMC) gene promoter.

Heterodimers of RXR and NGFI-Bα and β (but not γ) can bind to DR5 response elements and on these elements the heterodimer complex is efficiently activated by RXR ligands. Further it is becoming increasingly apparent that this may be an important physiological mechanism of regulation of NGFI-Bβ mediated gene expression. Additionally, the activity of NGFI-B family members appears to be independently regulated by posttranslational modifications such as phosphorylation that occurs independently of ligand binding to the nuclear receptor or heterodimer complex.

NGFI-Bβ-RXR heterodimers are present in the developing CNS in vivo and naturally occurring RXR ligands accumulate during development and in the postnatal brain consistent with a functional role for NGFI-Bβ-RXR heterodimers in the maintenance of developing and mature neurons.

In mammals three forms of RXR have been identified RXR α (NM_002957), RXR β (XM_042579) and RXR γ (XM_053680). The RXR family is ubiquitously expressed, although individual RXR genes display unique but overlapping patterns of expression during development and in adult tissues.

Known RXR ligands include the vitamin A metabolite 9-cis retinoic acid, and a variety of fatty acid lipid metabolites including the essential fatty acid docosahexaenoic acid (DHA; 22:6n-3). DHA deficiencies lead to neurological abnormalities and diminished learning ability in man (see Gamoh, et al, Neurosci 93:237-241 (1999); Fernstrom, Lipids 34:161-169 (1999); Sheaff Greiner, et al, Lipids Suppl 34:239-243 (1999)). Moreover, dietary DHA may be beneficial in the treatment of atherosclerosis, inflammation and cancer (Horrocks, et al, Pharmacol Res 40:211-225 (1999); Rose, et al, Pharmacol Theraput 83:217-244 (1999)).

Given the ubiquitous expression of RXR, the level of NGFI-Bβ expression may determine the responsiveness of neurons to RXR ligands. NGFI-B family members are highly expressed in the adult nervous system where they are induced as part of the immediate early response to stimuli such as growth factors, membrane depolarization, and seizures. Their-pattern of expression outside the nervous system is broad.

NGFI-Bβ and its highly homologous family members Nur77 and Nor1 can be rapidly induced by various stimuli, including hypoxic/ischemic stress and kainic acid-induced excitotoxicity, (Donaldson et al., Neurosci. Lett (1995) 196 (3) 181-4; Schmidt-Kastner et al., Science World J. 2001 1(1 Suppl 3) 95) and recent studies have identified a function for NGFI-Bβ-RXR heterodimers in neuronal survival in response to injury. The use of NGFI-B/RXR specific compounds could thus provide a novel therapeutic avenue for the treatment of stroke and neuronal damage, healing and repair.

The expression of NGFI-B family members has also been associated with the differentiation and survival of dopaminergic neurons generated from embryonic stem cells. (U.S. Pat. Nos. 6,395,546, 6,312,949, and 6,284,534). The use of NGFI-B/RXR specific compounds could thus also provide a novel method of generating dopaminergic neurons for transplantation and for improving the survival of cells once transplanted into the recipient.

Various studies implicate NGFI-Bβ (Nurr1) as a critical regulator of dopamine production in the ventral mid brain, and have demonstrated that NGFI-Bβ mutant mice fail to generate midbrain neurons with a dopaminergic phenotype, (Science (1997) 276 248-250; Proc. Natl. Acad. Sci. USA (1998) 95 4013-4018). Since loss of midbrain dopaminergic neurons is associated with the etiology of Parkinson's disease, the use of NGFI-B/RXR specific compounds could provide a novel therapeutic avenue for the treatment of this disease.

NGFI-Bβ+/− adult mice also show greater susceptibility to 1-methyl-4-phenyl-1,2,3,6-tetrahydropyridine (MPTP), a neurotoxin that elicits Parkinson's disease symptoms, (Le et al., (1999) Exp. Neurol. 159(2), 451-8) suggesting that Nurr1 expression is protective to the development of Parkinson's in adults. Finally NGFI-Bβ polymorphisms are associated with increased risk for Parkinson's disease and diffuse Lewy body disease (Zheng et al., Arch Neurol 2003 60(5) 722-5).

These results suggest that maintaining Nurr1 activity, for example through administering one of the compounds of the present invention may delay or prevent onset of Parkinson's and other neurodegenerative diseases. Accordingly compounds that modulate NGFI-B or NGFI-Bβ/RXR heterodimers would be likely to have utility for use in the treatment, prevention or amoliration of the symptoms of Parkinson's disease.

Mutations in NGFI-Bβ have also been identified in patients with schizophrenia and manic-depressive illness (WO 01/00907), suggesting that compounds that modulate NGFI-B or NGFI-Bβ/RXR heterodimers would be likely to have utility for use in the treatment, prevention or amoliration of the symptoms of schizophrenia and manic depressive illness.

NGFI-Bβ expression in the paraventricular nucleus and adrenal cortex is induced by stress, and ACTH treatment strongly up regulates NGFI-Bα and, expression in the adrenal gland. In addition NGFI-Bα was shown to regulate the steroid 21-hydroxylase (CYP21) and steroid 17-hydroxylase (CYP17) gene promoters (Mol. Cell. Biol. (1993) 13 861-868. The positive action of CRH on the POMC promoter was shown to be modulated via NGFI-Bα and β with the feedback repression of the hypothalamus-pituitary axis (HPA) by glucocorticoids at the level of the pituitary mediated by direct non-productive GR-NGFI-B interactions. Accordingly compounds that modulate NGFI-B or NGFI-B/RXR heterodimers would be likely to have utility for use in the treatment, prevention or amoliration of the symptoms of HPA dysfunction.

The induction of the genes encoding the NGFI-B family members by pro-inflammatory cytokines suggested a role for this family in mediating inflammatory responses. Indeed recent studies have suggested that these receptors are expressed at sites of chronic inflammation such as the synovium of patients with arthritis and in human atherosclerotic lesions (WO 01/87923). Accordingly compounds that modulate NGFI-B/RXR heterodimers would be likely to have utility for use in the treatment, prevention or amoliration of the symptoms of inflammatory responses including arthritis and in human atherosclerotic lesions.

Over expression of NGFI-Bα in smooth muscle cells inhibits cell proliferation and is protective in a transgenic mouse model of atherosclerosis while a dominant negative receptor has the opposite effects (EMBO. J. (1997) 16 (8) 1865-75). Thus members of the NGFI-B gene family are linked to the control of cell proliferation and may function as natural brake to dampen acute inflammatory reactions.

Retinoic acids and other retinoids exert anticancer effects through the retinoid receptors, the retinoic acid receptors (RARs) and retinoid X receptors (RXRs). Recently it has been demonstrated that the anticancer effects of retinoids on MDA-MB-231 breast cancer cells were mediated by RXR-NGFI-B family heterodimers, (Mol. Cell. Biol. (1997) 17(11) 6598-608). Accordingly compounds that modulate NGFI-B or NGFI-B/RXR heterodimers would be likely to have utility for use in the treatment, prevention or amoliration of cancer.

Although single genetic knockouts of NGFI-B α and γ appear normal, double knockouts of compound heterozygotes (NGFI-B α−/− NGFI-B γ and NGFI-B α+/−NGFI-B γ−/−) develop myeloid leukemia once again coupling the NGFI-B to cell proliferation and immune cell function. Accordingly compounds that modulate NGFI-B or NGFI-B/RXR heterodimers would be likely to have utility for use in the treatment, prevention or amoliration of the symptoms of acute inflammatory reactions.

BRIEF SUMMARY OF THE INVENTION

The present invention provides substituted pyrimidines which are effective modulators of the NGFI-B family. In one embodiment, the invention includes modulators of NGFI-Bβ/RXR heterodimers. As such, the present invention provides novel compositions and methods of using substituted pyrimidines which have the general formula: (I)

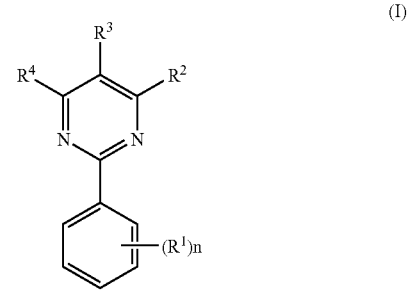

Wherein, n is 0 to 5;
  $R^1$ is each independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;
  $R^2$ and $R^3$ are selected as in a) or b) as below,
  a) $R^2$ is selected from the group consisting of optionally substituted aryl, optionally substituted heteroaryl, optionally substituted cycloalkyl, optionally substituted heterocyclyl, optionally substituted aralkyl, and optionally substituted heteroaralkyl, —OR$^6$, —S(O)$_t$R$^6$, —N(R$^7$)R$^8$, —N(R$^9$)S(O)$_t$R$^{10}$, —C(O)R$^6$, —C(O)OR$^6$, and —C(O)N(R$^7$)R$^8$;

and R$^3$ is independently selected from the group consisting of hydrogen, halo, pseudohalo, cyano, nitro, hydroxy, formyl, mercapto, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl; or b) R$^2$ and R$^3$, together with the carbon atom to which they are attached, form an optionally substituted cycloalkyl ring, optionally substituted heterocyclyl ring, an optionally substituted cycloalkenyl ring;

R$^4$ selected from the group consisting of hydrogen, halo, pseudohalo, cyano, nitro, hydroxy, formyl, mercapto, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl optionally substituted heterocyclylalkyl, —R$^{12}$—OR$^{13}$, —R$^{12}$—N(R$^{14}$)R$^{15}$, —R$^{12}$—C(O)R$^{13}$, —R$^{12}$—C(O)OR$^{15}$, —R$^{12}$—C(O)N(R$^{14}$)R$^{15}$, —R$^{12}$—N(R$^{14}$)C(O)R$^{15}$, —R$^{12}$—N(R$^{14}$)C(O)OR$^{15}$, —R$^{12}$—S(O)$_t$R$^{15}$ and —R$^{12}$—S(O)$_t$N(R$^{14}$)R$^{15}$;

R$^6$ represents optionally substituted alkyl, optionally substituted aryl, optionally substituted aralkyl or optionally substituted heterocyclyl;

R$^7$ represents H or optionally substituted alkyl;

R$^8$ represents optionally substituted alkyl, optionally substituted aryl, optionally substituted aralkyl or optionally substituted heterocyclyl;

R$^9$ represents H or optionally substituted alkyl;

R$^{10}$ represents optionally substituted alkyl, optionally substituted aryl, optionally substituted aralkyl or optionally substituted heterocyclyl;

R$^{12}$ represents a C$_1$-C$_6$ alkyl, C$_1$-C$_6$ alkenyl, C$_1$-C$_6$ alkynyl or C$_1$-C$_6$ alkoxy;

R$^{13}$ represents optionally substituted alkyl, optionally substituted aryl, optionally substituted aralkyl or optionally substituted heterocyclyl;

R$^{14}$ represents H or optionally substituted alkyl;

R$^{15}$ represents optionally substituted alkyl, optionally substituted aryl, optionally substituted aralkyl or optionally substituted heterocyclyl, and where each t is independently 0 to 2.

Methods of use of the compounds and compositions disclosed herein are also provided, including their use as receptor agonists, partial agonists, inverse agonists, partial antagonists, or antagonists of the NGFI-B family, and particularly NGFI-Bβ/RXR heterodimers. In one aspect the invention includes both in vitro and in vivo uses of the compounds and compositions for the treatment, prevention, or amelioration of one or more symptoms of diseases or disorder that is modulated by nuclear receptor activity, including the NGFI-B family, or in which nuclear receptor activity, including the NGFI-B family is implicated.

Methods of altering nuclear receptor activity, including the NGFI-B family and or their corresponding RXR heterodimers, by contacting the receptor with one or more compounds or compositions provided herein, are provided. Also provided are pharmaceutical compositions comprising any of the compounds or compositions provided herein.

Methods of treatment, prevention, or amelioration of one or more symptoms of a disease or disorder in which NGFI-B family activity is implicated are provided, including without limitation Parkinson's disease, cancer, Alzheimer's disease, schizophrenia, manic depressive illness, multiple sclerosis, neuronal inflammatory responses, neuronal injury, stroke, neuronal degeneration, inflammation, acute inflammatory reactions, osteoporosis, arthritis, rheumatoid arthritis, psoriatic arthritis, sarcoid arthritis, osteoarthritis, ulcerative colitis, thyrroiditis, atherosclerosis, and atherosclerosis related cardiovascular and coronary heart disease by administering a compound or composition of the present invention to patient in need of such treatment.

Methods are provided for the treatment, prevention, or amelioration of one or more symptoms of, as well as treating the complications of diseases in which NGFI-B family activity is implicated including without limitation Parkinson's disease, cancer, Alzheimer's disease, schizophrenia, manic depressive illness, multiple sclerosis, neuronal inflammatory responses, neuronal injury, stroke, neuronal degeneration, inflammation, acute inflammatory reactions, osteoporosis, arthritis, rheumatoid arthritis, psoriatic arthritis, sarcoid arthritis, osteoarthritis, ulcerative colitis, thyrroiditis, atherosclerosis, and atherosclerosis related cardiovascular and coronary heart disease by administering a compound or composition of the present invention to patient in need of such treatment.

Methods are provided for regulating the activity of NGFI-B β/RXR heterodimers in neuronal cells, and for improving the differentiation and survival of dopaminergic neuronal cells in culture comprising incubating a stem cell with a compound or composition of the present invention. In one aspect the stem cell can comprise an embryonic stem cell, in another embodiment in can comprise a stem cell derived from an adult.

The present invention also includes methods for the use of any compound or composition of the present invention for the production of neuronal cells for issue transplantation. In another aspect the present invention includes methods for the use of a compound or composition of the present invention for maintaining neuronal cell viability during before and during a transplantation procedure In a further aspect, methods are provided for treatment, prevention, or amelioration of neurological diseases such as Parkinson's, comprising administering to a patient in need thereof of one of the compounds or compositions of the present invention.

The present invention also includes methods for the treatment, prevention, or amelioration of neurological diseases such as Alzheimer's disease, comprising administering to a patient in need thereof of one of the compounds or compositions of the present invention.

Methods are provided for treatment, prevention, or amelioration of neurological diseases such as multiple sclerosis, comprising administering to a patient in need thereof of one of the compounds or compositions of the present invention.

The present invention also provides a method of treating or preventing inflammatory immune disease in a subject by administering to the subject in need of such treatment any compound or composition of the present invention. In one aspect the inflammatory disease includes arthritis, including without limitation rheumatoid arthritis (RA); psoriatic arthritis, infectious arthritis, juvenile rheumatoid arthritis; osteoarthritis, and spondyloarthropaties.

A compound or composition of the present invention may also be administered to prevent or reduce the risk of occurrence, or recurrence where the potential exists, of coronary heart disease event, a cerebrovascular event, and/or intermittent claudication.

In another aspect, the present compounds and compositions are intended to treat, or prevent the occurrence of all diseases classified as osteoporosis, particularly post-menopausal osteoporosis, senile osteoporosis, idiopathic osteoporosis, immobilization osteoporosis, post-partum osteoporosis, juvenile osteoporosis, and osteoporosis secondary to gonadal insufficiency, malnutrition, hyperprolactinemia, prolactinoma, disorders of the gastrointestinal tract, liver, or kidneys, and osteoporosis that is a sequella of prior osteomalacia, chronic acidosis, thyrotoxicosis, hyperparathyroidism, glucocorticoid excess or chronic disorders involving the bone marrow, and heritable forms of osteoporosis such as osteogenesis imperfecta and its variants, and other heritable disorders of connective tissue.

Combination therapies and pharmaceutical compositions including a NGFI-B family receptor agonist, partial agonist, partial antagonist, or antagonist of the present invention and an additional active compound are also provided. In certain embodiments of the combination therapies, a composition of the present invention and the additional active compound are part of a single therapeutic composition (e.g. such that the administration may be accomplished with a single composition). In other embodiments, a composition of the present invention and the additional active compound are separate compositions (e.g. such that each composition may be administered separately to the subject). In preferred embodiments, a compound or composition of the present invention and the additional active compound are administered to the subject at about the same time (e.g., within a few seconds, minutes, or hours of each other).

In one embodiment, the combination therapy includes administration of a compound of the present invention and one or more additional active agents, selected from levodopa (L-DOPA or L-dihydroxyphenylalanine), L-aromatic amino acid decarboxylase (AADC) inhibitors and/or catechol O-methyl transferase (COMT) inhibitors.

In another aspect, the combination therapy includes administration of a compound of the present invention with an anti-inflammatory compound. In one aspect of this combination therapy, the anti-inflammatory compound is selected from a matrix metalloproteinase inhibitor, an inhibitor of pro-inflammatory cytokines (e.g., anti-TNF molecules, TNF soluble receptors, non-steroidal anti-inflammatory drugs (NSAIDs) such as prostaglandin synthase inhibitors (e.g., choline magnesium salicylate, salicylsalicyclic acid), COX-1 or COX-2 inhibitors, aspirin, acetaminophen, ibuprofen or corticosteroids, such as methylprednisone, prednisone, or cortisone.

In another embodiment the combination therapy comprises the administration of one or more of the compounds of the present invention in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; LXR α or β agonists, antagonists, or partial-agonists, FXR agonists, antagonists, or partial agonists, an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin.

The present invention also comprises a combination therapy for the administration, to a human afflicted with osteoporosis, comprising a combination of a parathyroid hormone (PTH) or physiologically active fragment thereof, (hPTHF 1-34) for example with any of the compounds or compositions claimed herein.

In another embodiment the combination therapy further comprises a dietary calcium supplement and any of the compounds or compositions claimed herein. The invention also comprises pharmaceutical compositions intended for use in this method.

BRIEF DESCRIPTION OF THE DRAWINGS

In FIG. 2, fold activations of reporter gene expression are shown for various combinations of RXR and the test nuclear receptor in the presence of a fully activating concentration of a preferred compound of the present invention. In the Figure, "A" represents cells transfected with GAL4-DBD, "B" represents cells transfected with Nurr1 LBD, "C" represents cells transfected with FXR LBD, "D" represents cells transfected with PPARγ LBD, "E" represents cells transfected with PPARδ LBD, "F" represents cells transfected with LXRα LBD, "G" represents cells transfected with LXRβ LBD, "H" represents cells transfected with SXR LBD, "I" represents cells transfected with Nor1 LBD, "J" represents cells transfected with NGFI-Bγ LBD, "K" represents cells transfected with RARα LBD, "L" represents cells transfected with RARβ LBD, "M" represents cells transfected with RARα LBD, "N" represents cells transfected with VDR LBD, and "O" represents cells transfected with RXR LBD. Experimental details are presented in the Examples section of the specification.

FIG. 4A shows a comparison of the effects of a compound of the present invention and a RXR selective compound (LG1305) to activate Gal-4-Nurr1/RXR mediated gene expression in a Gal4 chimera reporter gene assay. FIG. 4B shows a comparison of the effects of a compound of the present invention and the RXR selective compound (LG1305) to activate Gal-4-RXR mediated gene expression in a Gal4 chimera—reporter gene assay.

DETAILED DESCRIPTION OF THE INVENTION

Definitions

Figure 1:
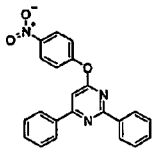
FIG. 1 Shows the activity in a Gal4 chimera/reporter gene assay of representative compounds of formula (I). Activity A represents an $EC_{50}$ of <10 uM, Activity B represents an $EC_{50}$ of 10 uM-50 uM and Activity C represents an $EC_{50}$ of >50 uM.
Figure 1:
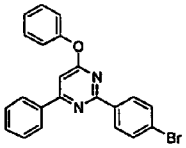
Figure 1:
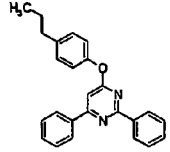
Figure 1:
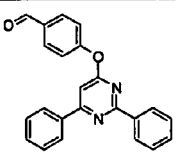
Figure 1:
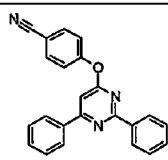
Figure 1:
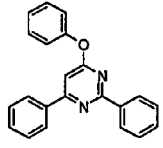
Figure 1:
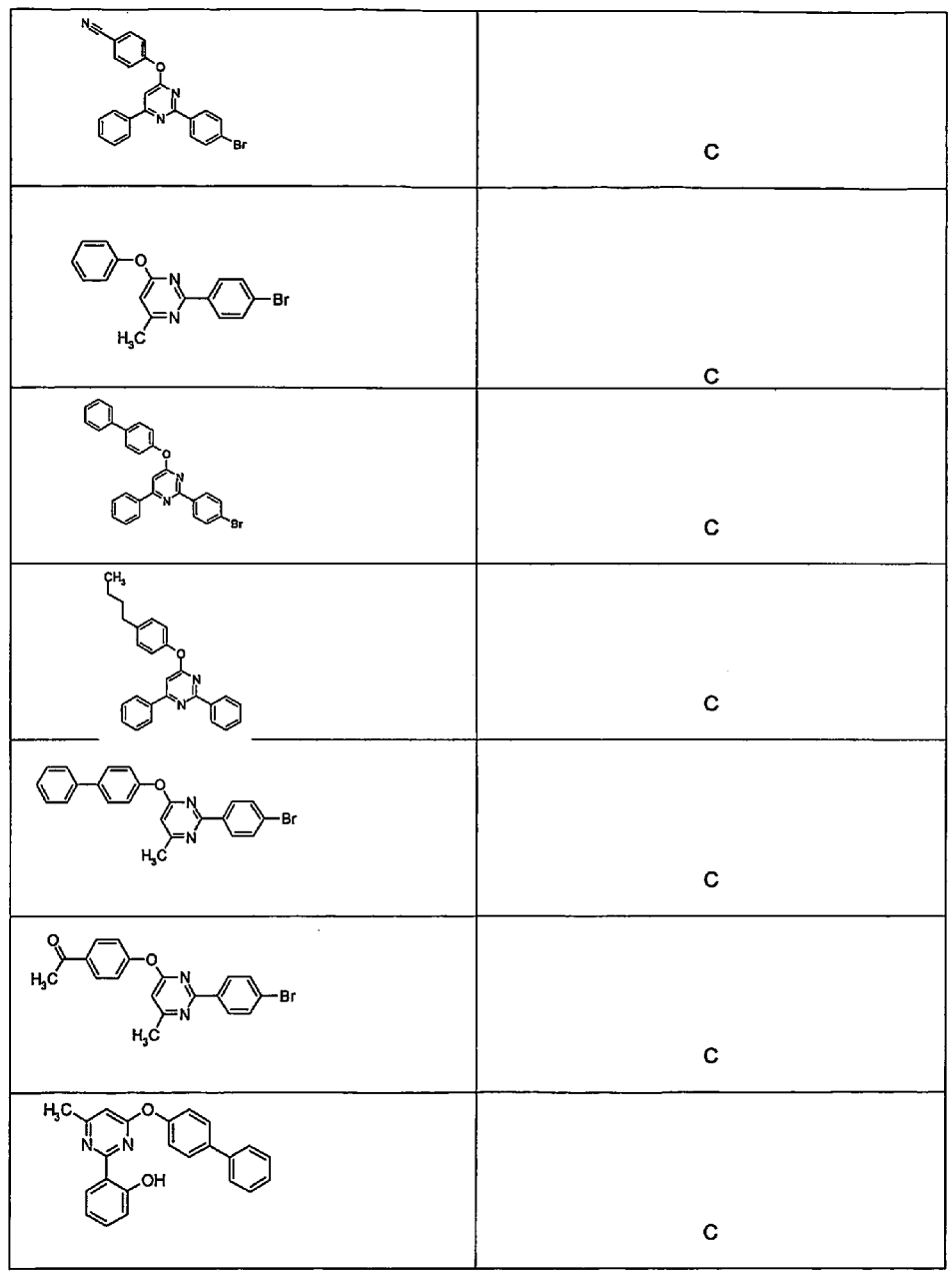
Figure 1:
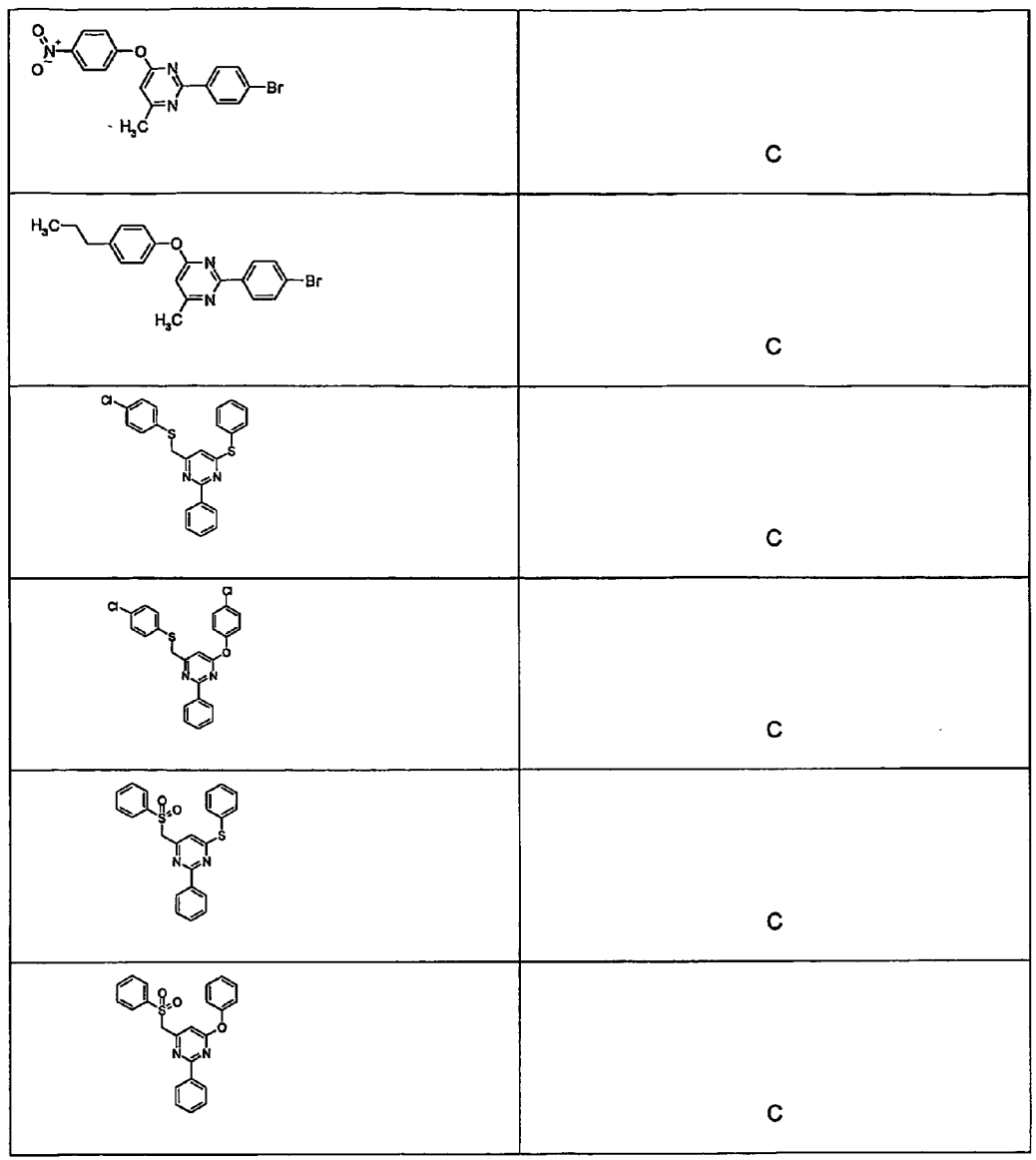
Figure 1:
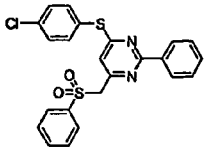
Figure 1:
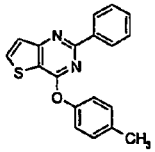
Figure 1:
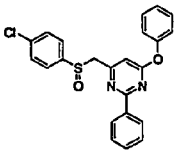
Figure 1:
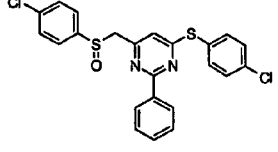
Figure 1:
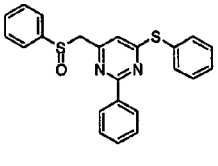
Figure 1:
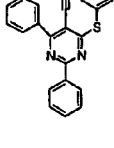
Figure 1:
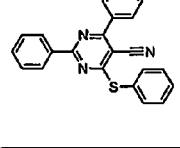
Figure 1:
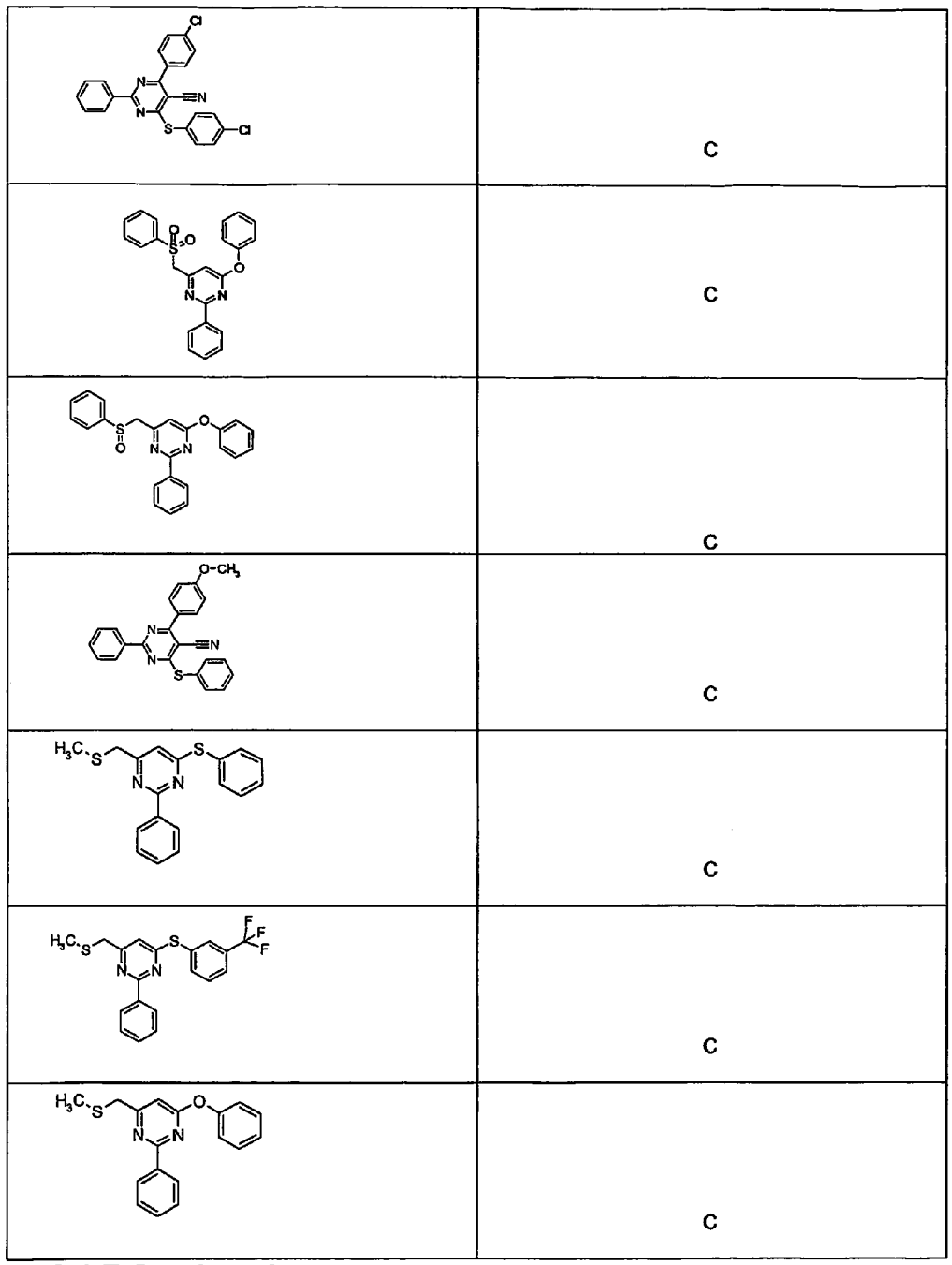
Figure 1:
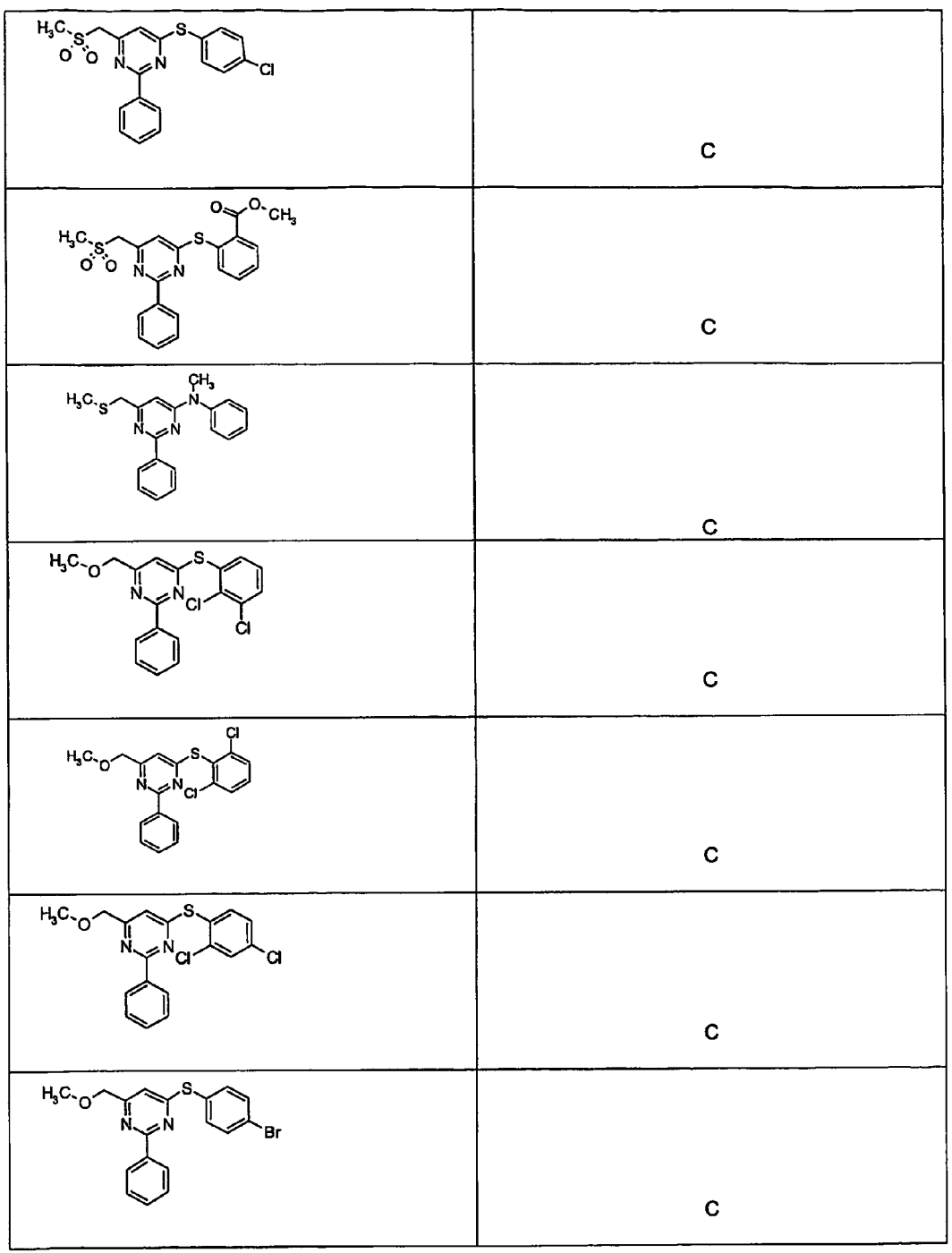
Figure 1:
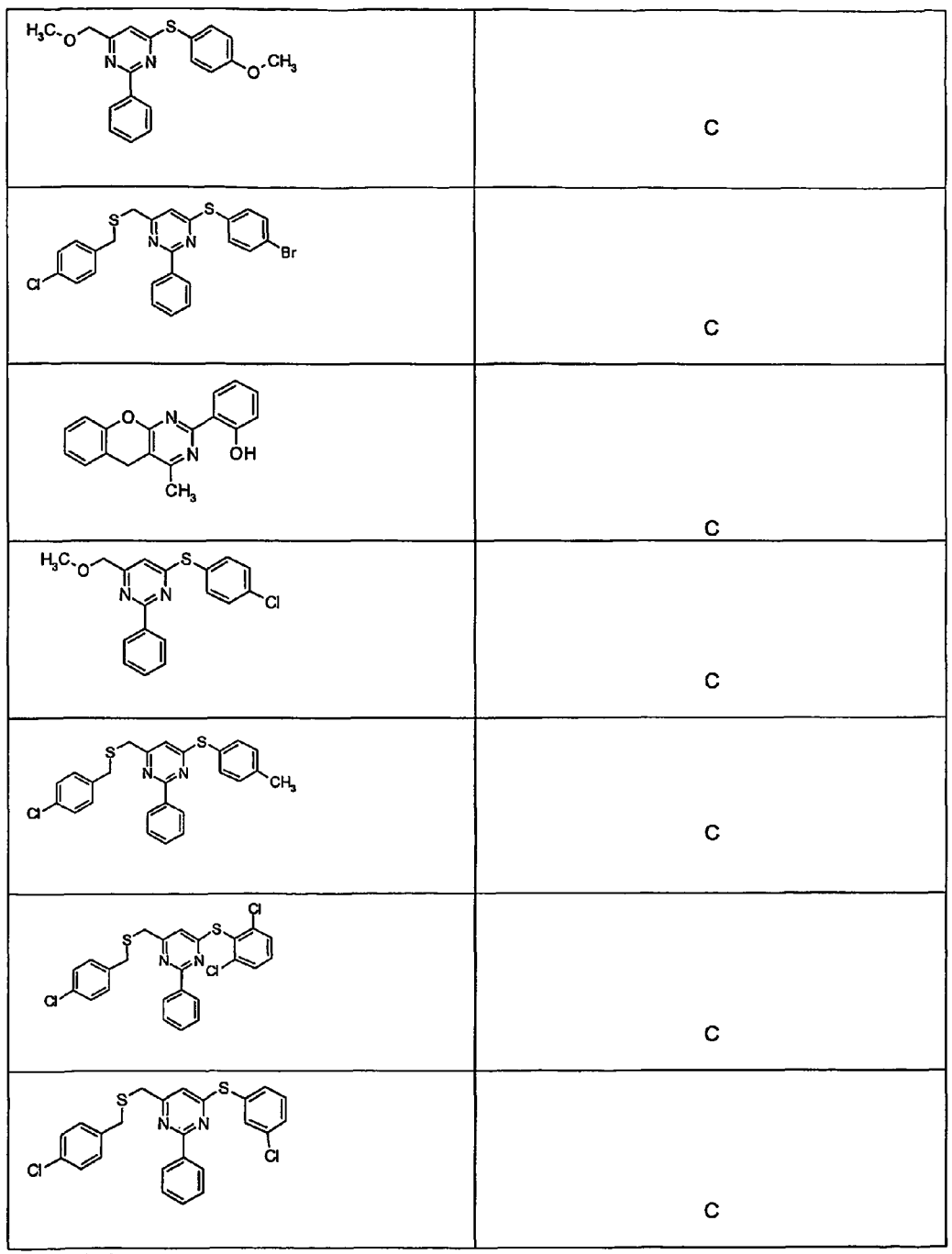
Figure 1:
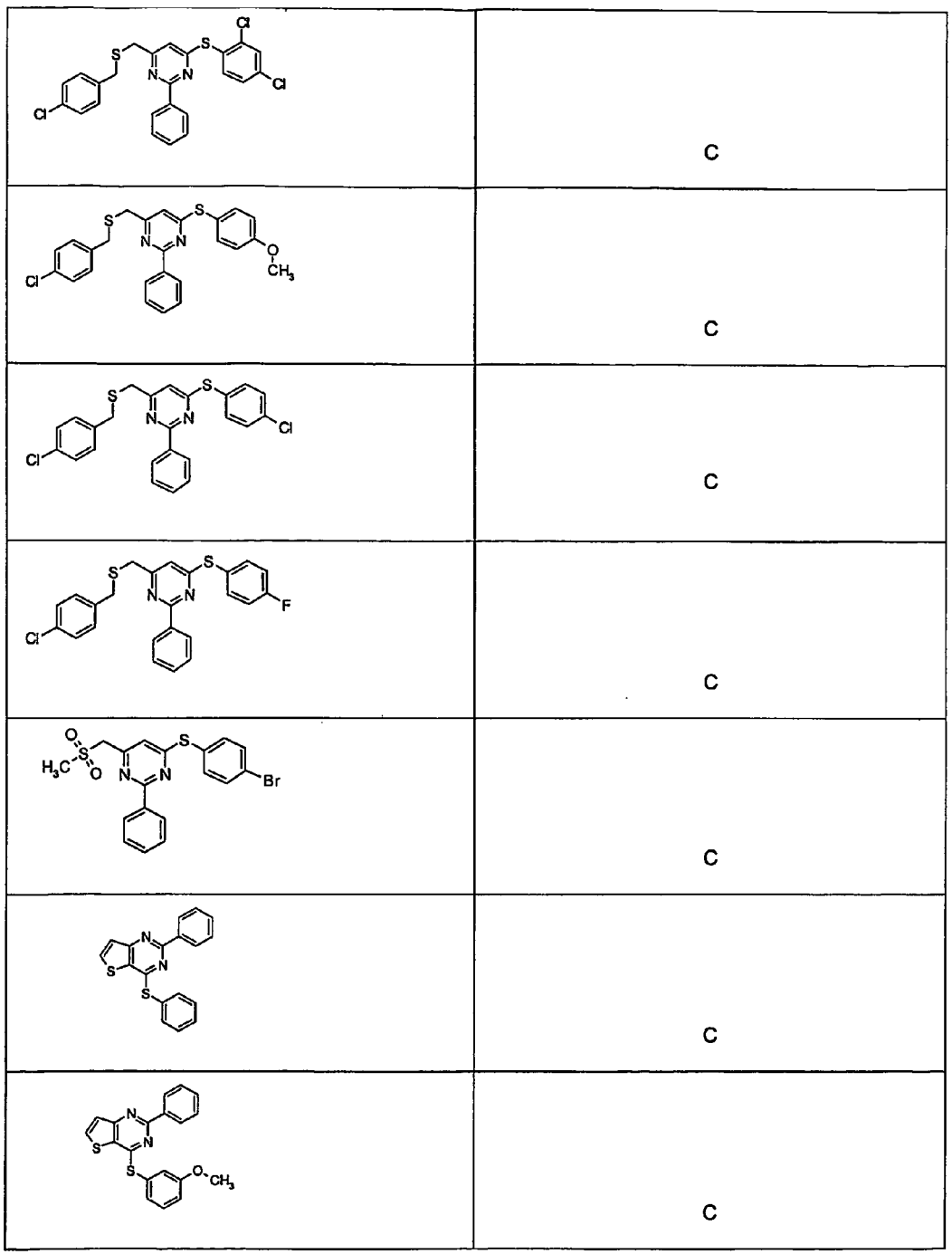
Figure 1:
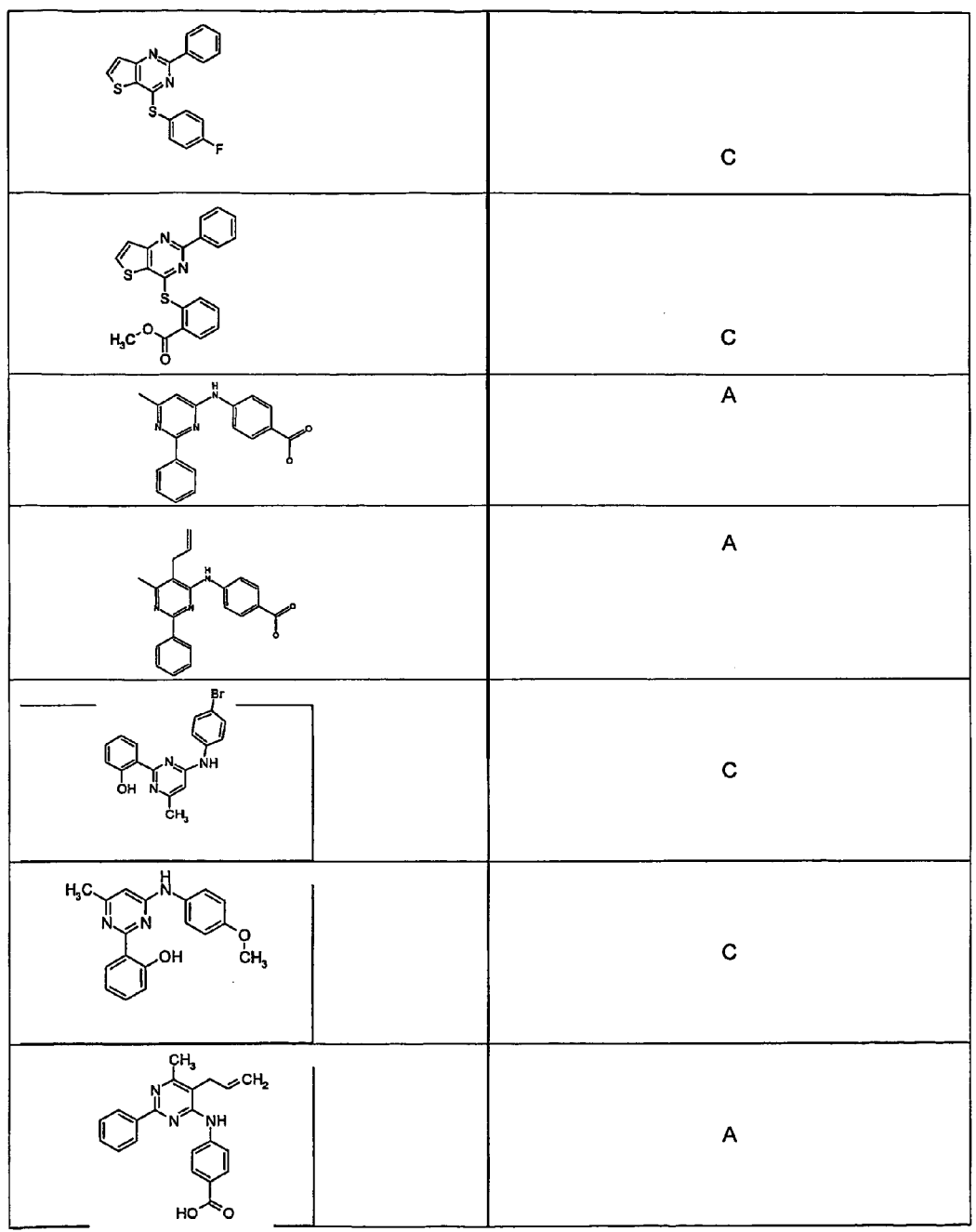
Figure 1:
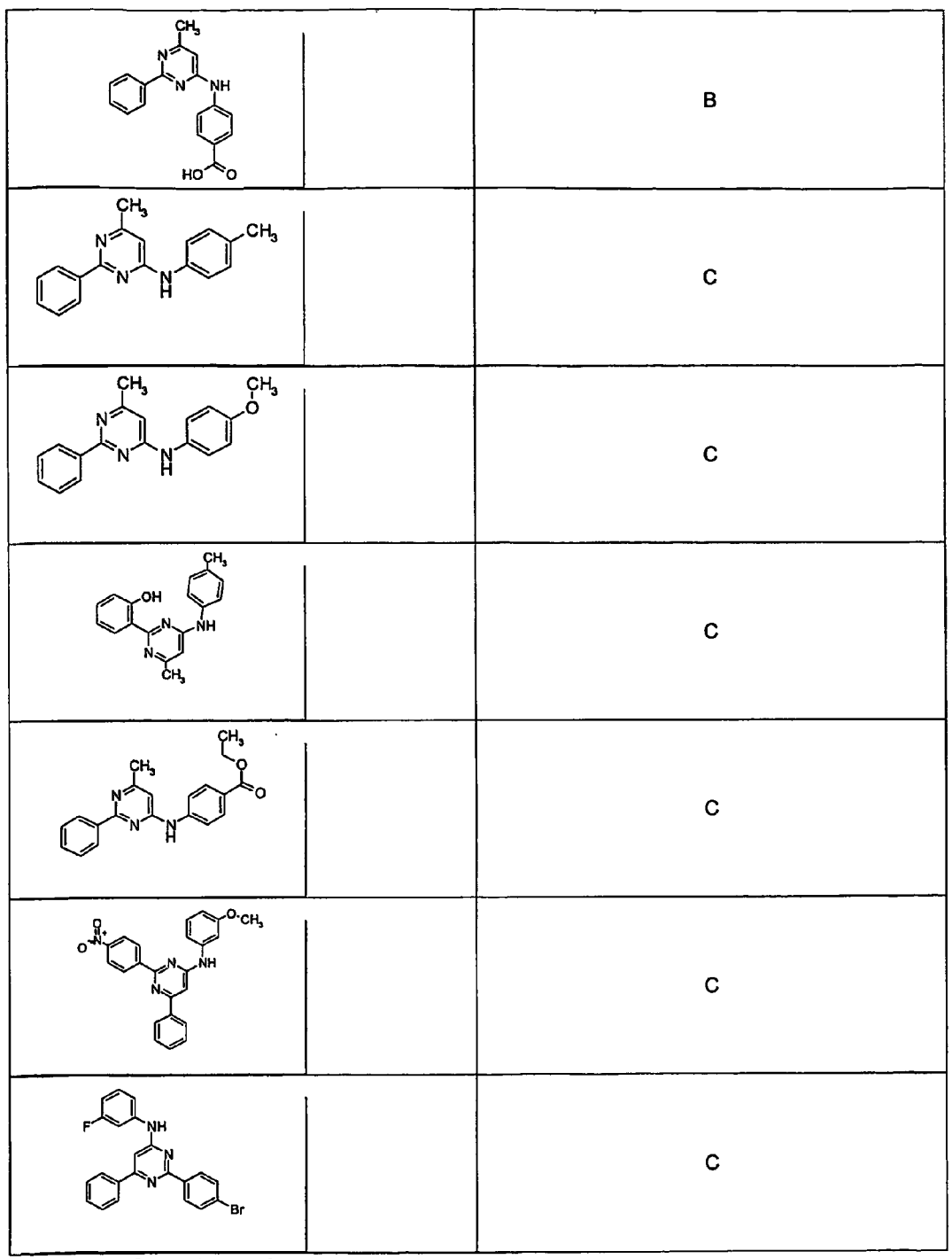
Figure 1:
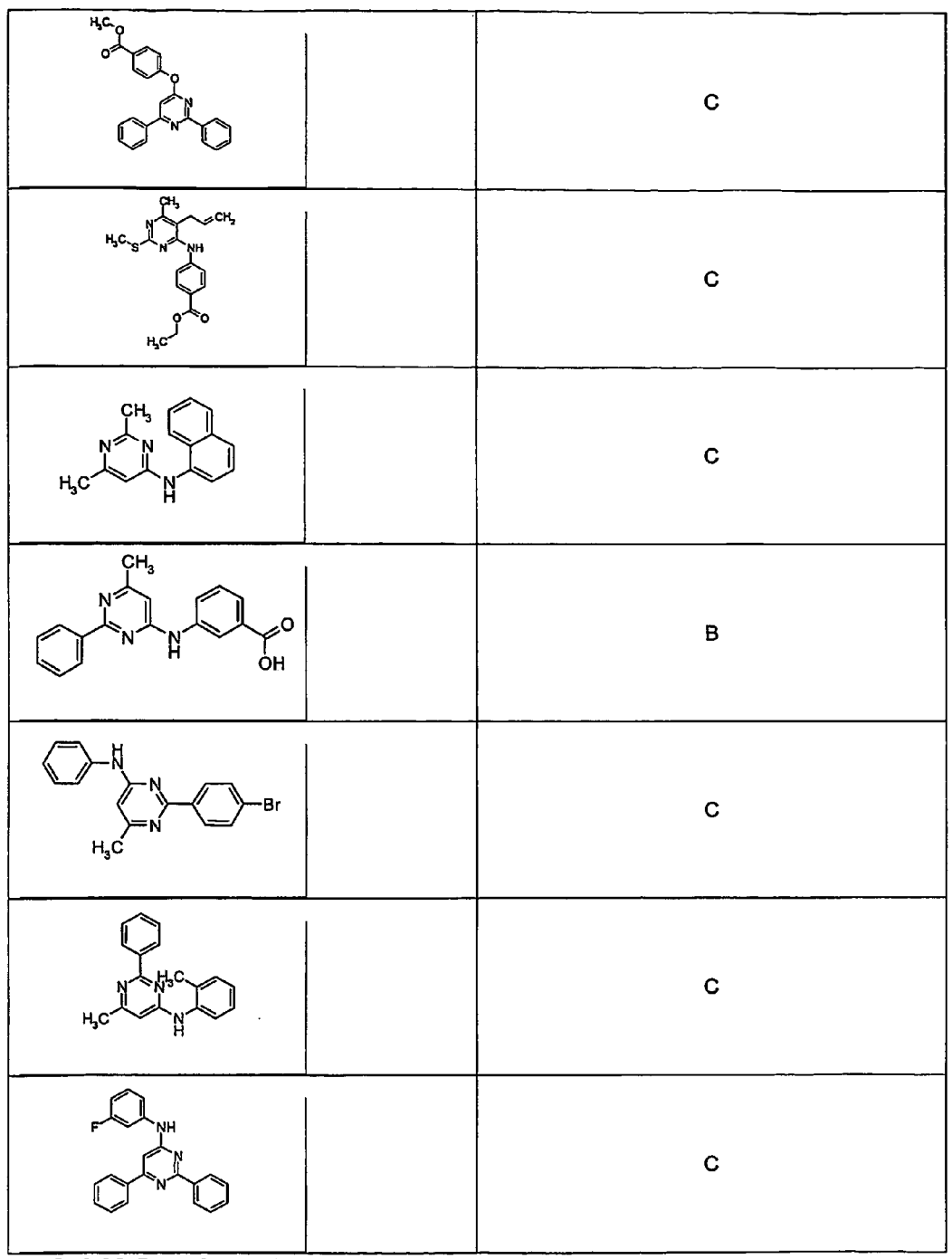
Figure 1:
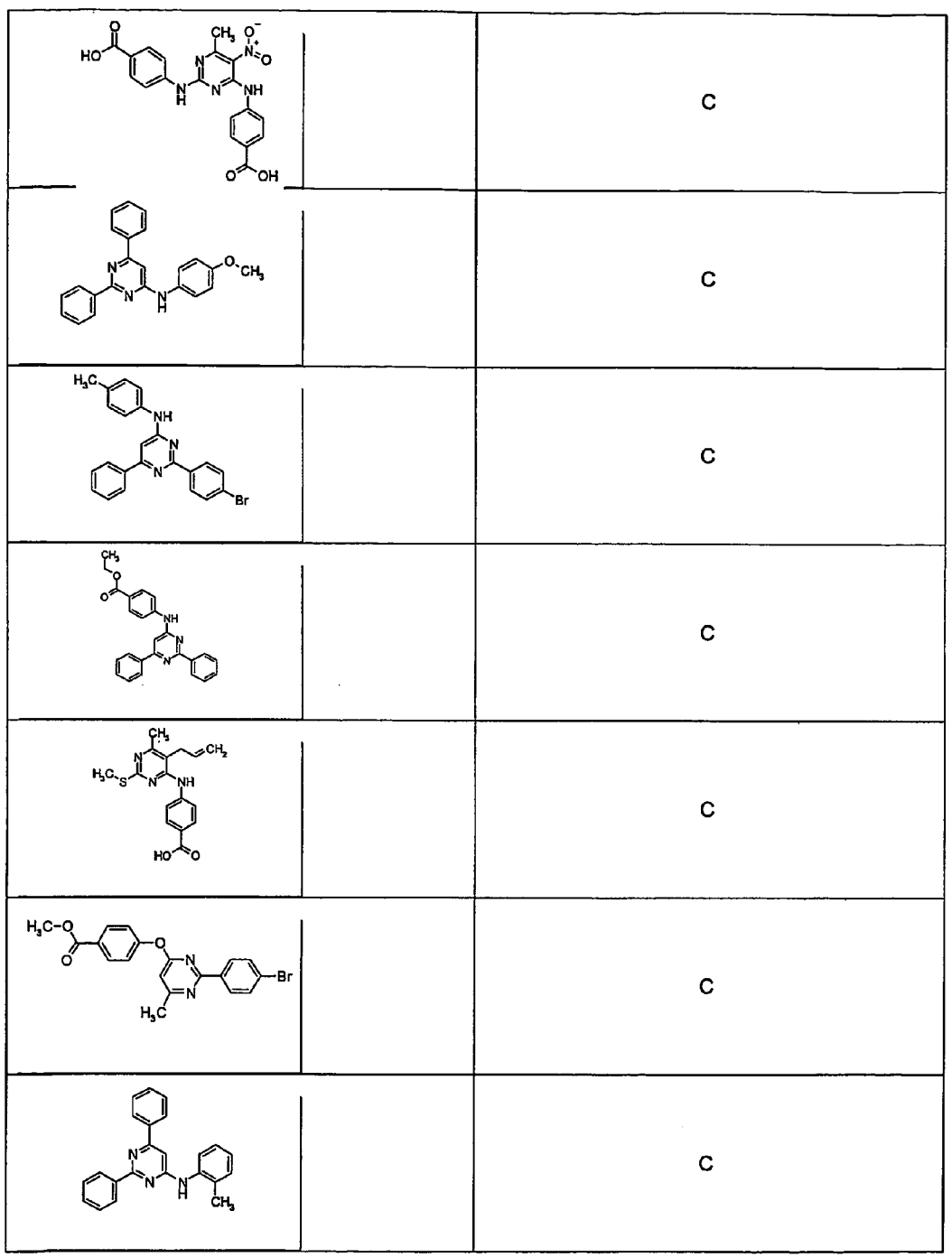
Figure 1:
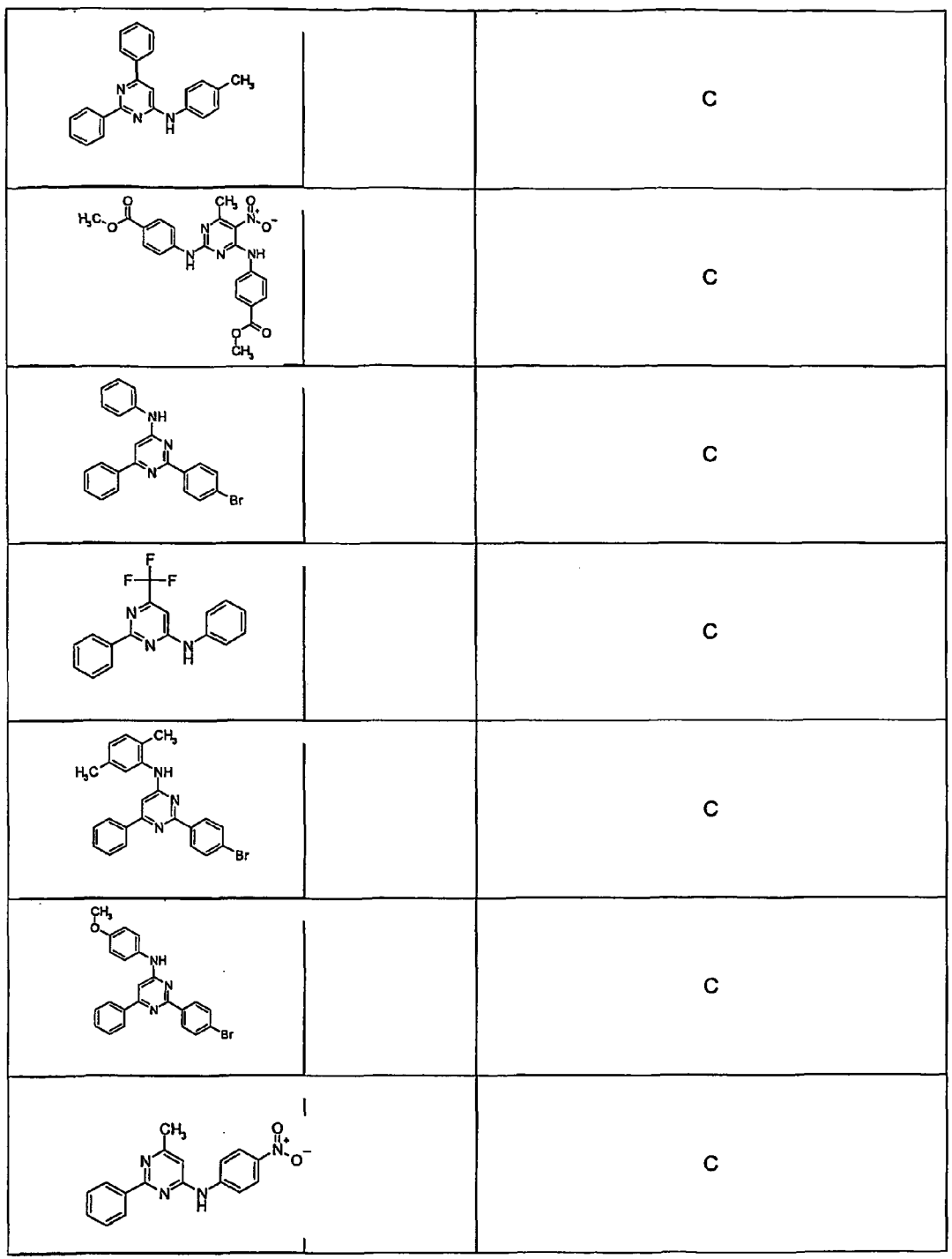
Figure 1:
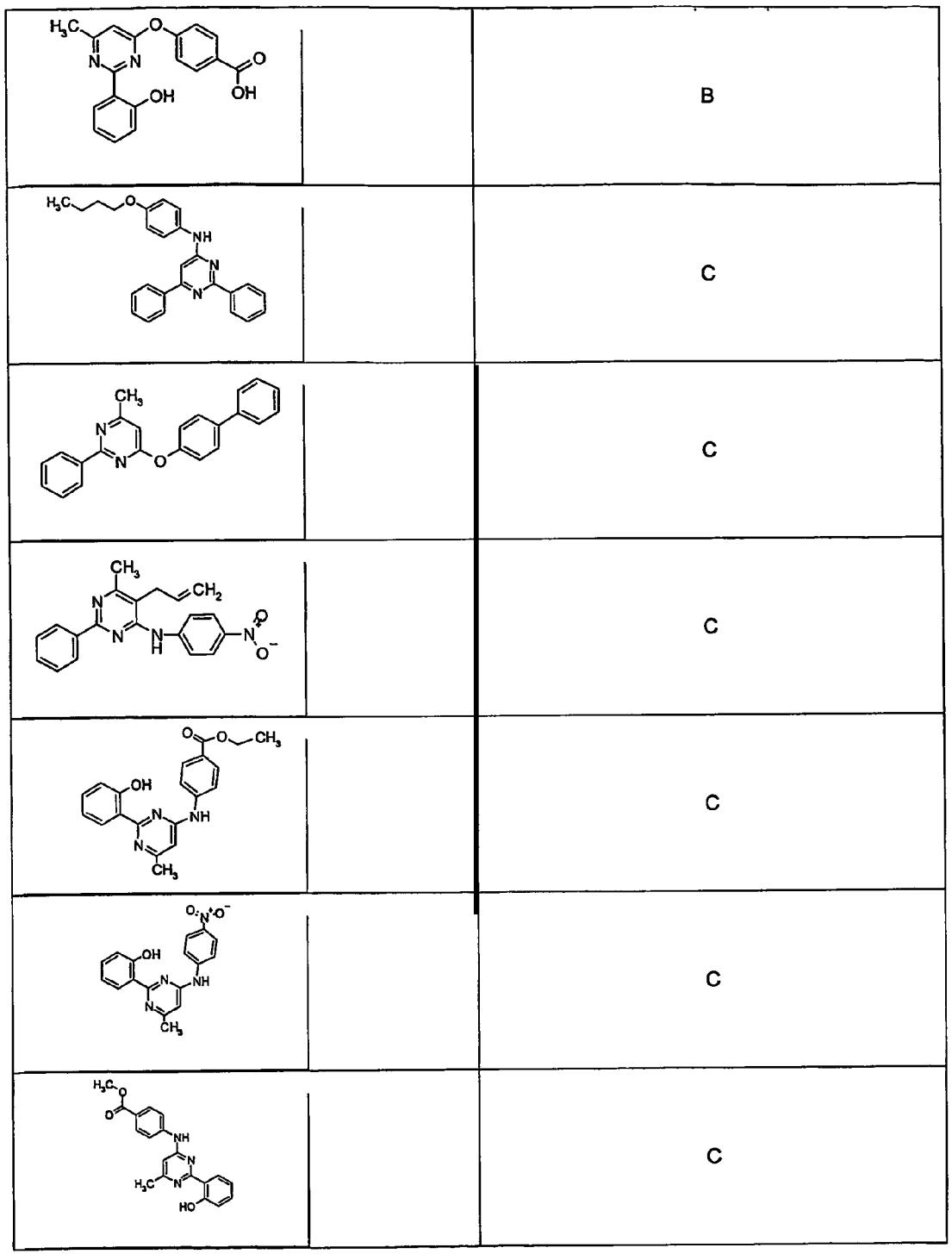
Figure 1:
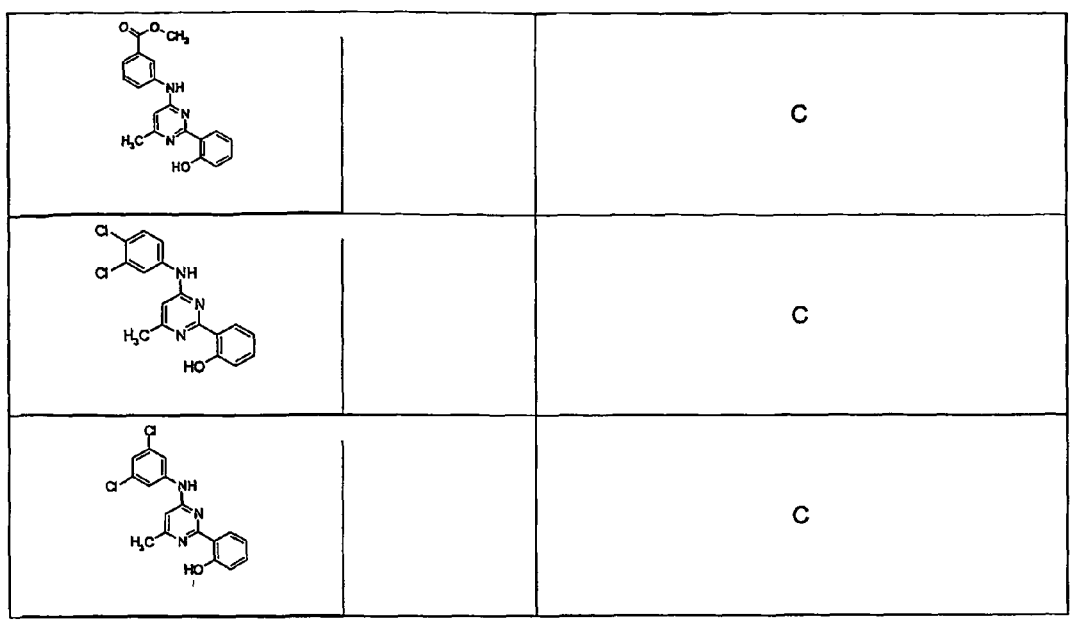

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, a nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is the farnesoid X receptor.

As used herein, an orphan nuclear receptor is a gene product that embodies the structural features of a nuclear receptor that was identified without any prior knowledge of their association with a putative ligand and/or for which the natural ligand is unknown. Under this definition, orphan nuclear receptors include, without limitation, farnesoid X receptors, liver X receptors (LXR α & β), retinoid X receptors (RXRα, β & γ), NGFI-B family receptors (NGFI-B, α, β and γ) and peroxisome proliferator activator receptors (PPAR α, β, & γ) (see, Giguere, *Endocrine Reviews* (1999), Vol. 20, No. 5: pp. 689-725).

The term "NGFI-B family" means all forms of NGFI-B, including NGFI-Bα, NGFI-Bβ and NGFI-Bγ, and their corresponding monomer, homodimer and heterodimeric forms with RXR.

The term "RXR" means all forms of RXR, including RXRα, RXRβ and RXRγ.

As used herein, "NGFI-B α" or "Nur77" refers to all mammalian forms of such receptor including, for example, mouse, rat and human and all alternative splice isoforms and naturally occurring isoforms and polymorphisms thereof.

As used herein, "NGFI-B β" or "Nurr1" refers to all mammalian forms of such receptor including, for example, mouse, rat and human, and all alternative splice isoforms and naturally occurring isoforms and polymorphisms thereof.

As used herein, "NGFI-B γ" or "NOR-1" refers to all mammalian forms of such receptor including, for example, mouse, rat and human, and all alternative splice isoforms and naturally occurring isoforms and polymorphisms thereof.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, "treatment" means any manner in which one or more of the symptoms of a disease or disorder are ameliorated or otherwise beneficially altered. Treatment also encompasses any pharmaceutical use of the compositions herein, such as use for treating a nuclear receptor mediated diseases or disorders, or diseases or disorders in which nuclear receptor activity, including activity derived from a NGFI-B family member or a NGFI-B family member complexed to RXR, is implicated.

As used herein, "amelioration" of the symptoms of a particular disorder by administration of a particular compound or pharmaceutical composition refers to any lessening, whether permanent or temporary, lasting or transient that can be attributed to or associated with administration of the composition.

As used herein, "$IC_{50}$" refers to an amount, concentration or dosage of a particular test compound that achieves a 50% inhibition of a maximal response, such as modulation of nuclear receptor activity, including a NGFI-B family member or a NGFI-B family member complexed to RXR, in an assay that measures such response.

As used herein, "$EC_{50}$" refers to a dosage, concentration or amount of a particular test compound that elicits a dose-dependent response at 50% of maximal expression of a particular response that is induced, provoked or potentiated by the particular test compound.

As used herein, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl(propenyl) and propargyl(propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to, groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to —S(O)$_2$—. As used herein, "sulfo" refers to —S(O)$_2$O—. As used herein, "halosulfonyl" refers to —S(O)$_2$—R in which R is a halo group, preferably fluoro.

As used herein, "carboxy" refers to a divalent radical, —C(O)O—.

As used herein, "aminocarbonyl" refers to —C(O)NH$_2$.

As used herein, "alkylaminocarbonyl" refers to —C(O) NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O) NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O) NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including S(O) and S(O)$_2$ groups, or optionally substituted nitrogen atoms, including —NR— and —N⁺RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, (CRR)$_n$—S(O)—(CRR)$_m$—, and —(CRR)$_n$—S(O)$_2$—(CRR)$_m$—, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or optionally substituted nitrogen atoms, where the nitrogen substituent is alkyl. Alkenylene groups include, but are not limited to, —CH═CH—CH═CH— and —CH═CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or optionally substituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur or optionally substituted nitrogen atoms, where the nitrogen substituent is alkyl. Alk(en)(yn)ylene groups include, but are not limited to, —C═C—(CH$_2$)$_n$—C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "optionally substituted alkyl," "optionally substituted alkenyl," "optionally substituted alkynyl," "optionally substituted cycloalkyl," "optionally substituted cycloalkenyl," "optionally substituted cycloalkynyl," "optionally substituted aryl," "optionally substituted heteroaryl," "optionally substituted heterocyclyl," "optionally substituted alkylene," "optionally substituted alkenylene," "optionally substituted alkynylene," "optionally substituted cycloalkylene," "optionally substituted cycloalkenylene," "optionally substituted cycloalkynylene," "optionally substituted arylene," "optionally substituted heteroarylene" and "optionally substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that when substituted, are independently substituted with one or more substituents, in certain embodiments one, two, three or four substituents, where the substituents are as defined herein, in one embodiment selected from $Q^1$.

In one embodiment, $Q^1$ represents alkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl, pseudohalo, —R$^{30}$—OR$^{31}$, —RF$^{30}$—SR$^{16}$, —R$^{30}$—N(R$^{32}$)(R$^{33}$), —R$^{30}$—C(J)R$^{34}$, —R$^{30}$—C(J)OR$^{31}$, —R$^{30}$—C(J)N(R$^{32}$)(R$^{33}$), —R$^{30}$—C(J)N(R$^{31}$)N(R$^{32}$)(R$^{33}$), —R$^{30}$—N(R$^{31}$)C(J)R$^{34}$, —R$^{30}$—N(R$^{31}$)C(J)OR$^{31}$, —R$^{30}$—N(R$^{31}$)C(J)N(R$^{32}$)(R$^{33}$), —R$^{30}$—OC(J)R$^{34}$, —R$^{30}$—OC(J)OR$^{31}$, —R$^{30}$—OC(J)N(R$^{32}$)(R$^{33}$), —Si(R$^{35}$)$_3$, —N(R$^{31}$)S(O)$_y$R$^{36}$ or —R$^{30}$—S(O)$_y$R$^{36}$;

where each $R^{30}$ is independently a direct bond or a straight or branched alkylene chain;

$R^{31}$ and $R^{34}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{32}$ and $R^{33}$ together with the nitrogen atom to which they are attached, form a heterocyclyl, heterocyclylalkenyl, or heteroaryl;

$R^{35}$ $R^{36}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each y is independently 0 to 2.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylid-ene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO2NHNH—. "Hydrazide" refers to the divalent group —C(O)NHNH—. "Azo" refers to the divalent group —N=N—. "Hydrazinyl" refers to the divalent group —NH—NH—.

Where the number of any given substituent is not specified (e.g., haloalkyl), there may be one or more substituents present. For example, "haloalkyl" may include one or more of the same or different halogens. As another example, "C$_{1-3}$alkoxyphenyl" may include one or more of the same or different alkoxy groups containing one, two or three carbons.

When the compounds described herein contain olefinic double bonds or other centers of geometric asymmetry, and unless specified otherwise, it is intended that the compounds include both E and Z geometric isomers. Likewise, all tautomeric forms are also intended to be included.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as reverse phase HPLC.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As employed herein, the following terms have their accepted meaning in the chemical literature.

Preferred Compounds

The present invention provides substituted pyrimidines which are effective modulators of the NGFI-B family, and in one embodiment modulators of NGFI-Bβ/RXR heterodimers. As such, the present invention provides novel compositions and methods of using substituted pyrimidines which have the general structure: (I)

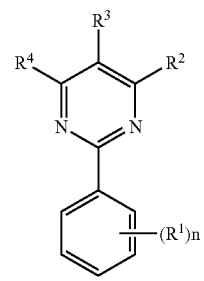

wherein
n is 0 to 5;

$R^1$ is each independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^2$ and $R^3$ are selected as in a) or b) as below, a) $R^2$ is selected from the group consisting of optionally substituted aryl, optionally substituted heteroaryl, optionally substituted cycloalkyl, optionally substituted heterocyclyl, optionally substituted aralkyl, and optionally substituted heteroaralkyl, —$OR^6$, —$S(O)_tR^6$, —$N(R^7)R^8$, —$N(R^9)S(O)_tR^{10}$, —$C(O)R^6$, —$C(O)OR^6$, and —$C(O)N(R^7)R^8$; and $R^3$ is independently selected from the group consisting of hydrogen, halo, pseudohalo, cyano, nitro, hydroxy, formyl, mercapto, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

or b) $R^2$ and $R^3$, together with the carbon atom to which they are attached, form an optionally substituted cycloalkyl ring, optionally substituted heterocyclyl ring, an optionally substituted cycloalkenyl ring;

$R^4$ selected from the group consisting of hydrogen, halo, pseudohalo, cyano, nitro, hydroxy, formyl, mercapto, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl optionally substituted heterocyclylalkyl, —$R^{12}$—$OR^{13}$, —$R^{12}$—$N(R^{14})R^{15}$, —$R^{12}$—$C(O)R^{13}$, —$R^{12}$—$C(O)OR^{15}$, —$R^{12}$—$C(O)N(R^{14})R^{15}$, —$R^{12}$—$N(R^{14})C(O)R^{15}$, —$R^{12}$—$N(R^{14})C(O)OR^{15}$, —$R^{12}$—$S(O)_tR^{15}$ and —$R^{12}$—$S(O)_tN(R^{14})R^{15}$;

$R^6$ represents optionally substituted alkyl, optionally substituted aryl, optionally substituted aralkyl or optionally substituted heterocyclyl;

$R^7$ represents H or optionally substituted alkyl;

$R^8$ represents optionally substituted alkyl, optionally substituted aryl, optionally substituted aralkyl or optionally substituted heterocyclyl;

$R^9$ represents H or optionally substituted alkyl;

$R^{10}$ represents optionally substituted alkyl, optionally substituted aryl, optionally substituted aralkyl or optionally substituted heterocyclyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl, and where each t is independently 0 to 2.

In one embodiment, the substituents, when substituted, are independently substituted with a group selected from $Q^1$, where $Q^1$ represents alkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl, pseudohalo, —$R^{30}$—$OR^{31}$, —$R^{30}$—$SR^{16}$, —$R^{30}$—$N(R^{32})(R^{33})$, —$R^{30}$—$C(J)R^{34}$, —$R^{30}$—$C(J)OR^{31}$, —$R^{30}$—$C(J)N(R^{32})(R^{33})$, —$R^{30}$—$C(J)N(R^{31})N(R^{32})(R^{33})$, —$R^{30}$—$N(R^{31})C(J)R^{34}$, —$R^{30}$—$N(R^{31})C(J)OR^{31}$, —$R^{30}$—$N(R^{31})C(J)N(R^{32})(R^{33})$, —$R^{30}$—$OC(J)R^{34}$, —$R^{30}$—$OC(J)OR^{31}$, —$R^{30}$—$OC(J)N(R^{32})(R^{33})$, —$Si(R^{35})_3$, —$N(R^{31})S(O)_yR^{36}$ or —$R^+$—$S(O)_yR^{36}$;

where each $R^{30}$ is independently a direct bond or a straight or branched alkylene chain;

$R^{31}$ and $R^{34}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{32}$ and $R^{33}$ together with the nitrogen atom to which they are attached, form a heterocyclyl, heterocyclylalkenyl, or heteroaryl;

$R^{35}$ $R^{36}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each y is independently 0 to 2.

In a preferred embodiment, $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Preferred embodiments of the substituted pyrimidines further include compounds of formula (II)

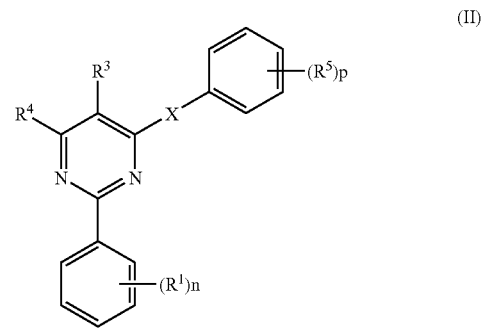

(II)

wherein n is 0 to 2; p is 0 to 2; X is $N(R^7)$, O, or $S(O)_r$ where r is 0 to 2;

$R^1$ is each independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^3$ is independently selected from the group consisting of hydrogen, halo, pseudohalo, cyano, nitro, hydroxy, formyl, mercapto, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^4$ selected from the group consisting of hydrogen, halo, pseudohalo, cyano, nitro, hydroxy, formyl, mercapto, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl optionally substituted heterocyclylalkyl, $-R^{12}-OR^{13}$, $-R^{12}-N(R^{14})R^{15}$, $-R^{12}-C(O)R^{13}$, $-R^{12}-C(O)OR^{15}$, $-R^{12}-C(O)N(R^{14})R^{15}$, $-R^{12}-N(R^{14})C(O)R^{15}$, $-R^{12}-N(R^{14})C(O)OR^{15}$, $-R^{12}-S(O)_tR^{15}$ and $-R^{12}-S(O)_tN(R^{14})R^{15}$;

each $R^5$ independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, $-OR^{20}$, $-S(O)_tR^{20}$, $-N(R^7)R^{20}$, $-N(R^9)S(O)_tR^{20}$, $-C(O)R^{20}$, and $-C(O)OR^{20}$;

$R^7$ and $R^9$ are each independently H or optionally substituted alkyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl, pseudohalo, $-R^{30}-OR^{31}$, $-R^{30}-SR^{16}$, $-R^{30}-N(R^{32})(R^{33})$, $-R^{30}-C(J)R^{34}$, $-R^{30}-C(J)OR^{31}$, $-R^{30}-C(J)N(R^{32})(R^{33})$, $-R^{30}-C(J)N(R^{31})N(R^{32})(R^{33})$, $-R^{30}-N(R^{31})C(J)R^{34}$, $-R^{30}-N(R^{31})C(J)OR^{31}$, $-R^{30}-N(R^{31})C(J)N(R^{32})(R^{33})$, $-R^{30}-OC(J)R^{34}$, $-R^{30}-OC(J)OR^{31}$, $-R^{30}-OC(J)N(R^{32})(R^{33})$, $-Si(R^{35})_3$, $-N(R^{31})S(O)_yR^{36}$ or $-R^{30}-S(O)_yR^{36}$;

where each $R^{30}$ is independently a direct bond or a straight or branched alkylene chain;

$R^{31}$ and $R^{34}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{32}$ and $R^{33}$ together with the nitrogen atom to which they are attached, form a heterocyclyl, heterocyclylalkenyl, or heteroaryl;

$R^{35}$ $R^{36}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each y is independently 0 to 2.

In another preferred embodiment, $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0; p is 0 to 2; X is $N(R^7)$, O, or $S(O)_r$ where r is 0 to 2;

$R^3$ is independently selected from the group consisting of hydrogen, halo, pseudohalo, cyano, nitro, hydroxy, formyl, mercapto, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^4$ selected from the group consisting of hydrogen, halo, pseudohalo, cyano, nitro, hydroxy, formyl, mercapto, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl optionally substituted heterocyclylalkyl, $-R^{12}-OR^{13}$, $-R^{12}-N(R^{14})R^{15}$, $-R^{12}-C(O)R^{13}$, $-R^{12}-C(O)OR^{15}$, $-R^{12}-C(O)N(R^{14})R^{15}$, $-R^{12}-N(R^{14})C(O)R^{15}$, $-R^{12}-N(R^{14})C(O)OR^{15}$, $-R^{12}-S(O)_tR^{15}$ and $-R^{12}-S(O)_tN(R^{14})R^{15}$;

each $R^5$ independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, $-OR^{20}$, $-S(O)_tR^{20}$, $-N(R^7)R^{20}$, $-N(R^9)S(O)_tR^{20}$, $-C(O)R^{20}$, and $-C(O)OR^{20}$;

$R^7$ and $R^9$ are each independently H or optionally substituted alkyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo, $-R^{30}-OR^{31}$, $-R^{30}-SR^{16}$, $-R^{30}-N(R^{32})(R^{33})$, $-R^{30}-C(J)R^{34}$, $-R^{30}-C(J)OR^{31}$, $-R^{30}-C(J)N(R^{32})(R^{33})$, $-R^{30}-C(J)N(R^{31})N(R^{32})(R^{33})$, $-R^{30}-N(R^{31})C(J)R^{34}$, $-R^{30}-N(R^{31})C(J)OR^{31}$, $-R^{30}-N(R^{31})C(J)N(R^{32})(R^{33})$, $-R^{30}-OC(J)R^{34}$, $-R^{30}-OC(J)OR^{31}$, $-R^{30}-OC(J)N(R^{32})(R^{33})$, $-Si(R^{35})_3$, $-N(R^{31})S(O)_yR^{36}$ or $-R^{30}-S(O)_yR^{36}$;

where each $R^{30}$ is independently a direct bond or a straight or branched alkylene chain;

$R^{31}$ and $R^{34}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{32}$ and $R^{33}$ together with the nitrogen atom to which they are attached, form a heterocyclyl, heterocyclylalkenyl, or heteroaryl;

$R^{35}$ $R^{36}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each y is independently 0 to 2.

In a preferred embodiment, $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0 to 2; p is 0 to 2; X is $N(R^7)$, O, or $S(O)_r$ where r is 0 to 2;

$R^1$ is each independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^3$ is independently selected from the group consisting of hydrogen, halo, pseudohalo, cyano, nitro, hydroxy, formyl, mercapto, optionally substituted lower alkyl, optionally substituted lower alkenyl, optionally substituted lower alkynyl, optionally substituted lower alkoxy, and optionally substituted lower aminoalkyl;

$R^4$ selected from the group consisting of hydrogen, halo, pseudohalo, cyano, nitro, hydroxy, formyl, mercapto, optionally substituted alkyl, optionally substituted alkenyl, optionally substituted alkynyl, alkoxy, aminoalkyl, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl optionally substituted heterocyclylalkyl, $-R^{12}-O^{13}$, $-R^{12}-N(R^{14})R^{15}$, $-R^{12}-C(O)R^{13}$, $-R^{12}-C(O)OR^{15}$, $-R^{12}-C(O)N(R^{14})R^{15}$, $-R^{12}-N(R^{14})C(O)R^{15}$, $-R^{12}-N(R^{14})C(O)OR^{15}$, $-R^{12}-S(O)_tR^{15}$ and $-R^{12}-S(O)_tN(R^{14})R^{15}$;

each $R^5$ independently selected from the group consisting of, halo, pseudohalo, cyano, nitro, hydroxy, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, $-OR^{20}$, $-S(O)_tR^{20}$, $-N(R^7)R^{20}$, $-N(R^9)S(O)_tR^{20}$, $-C(O)R^{20}$, and $-C(O)OR^{20}$;

$R^7$ and $R^9$ are each independently H or optionally substituted alkyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ is represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl pseudohalo, $-R30-OR31$, $-R^{30}-SR^{16}$, $-R^{30}-N(R^{32})(R^{33})$, $-R^{30}-C(J)R^{34}$, $-R^{30}-C(J)OR^{31}$, $-R^{30}-C(J)N(R^{32})(R^{33})$, $-R^{30}-C(J)N(R^{31})N(R^{32})(R^{33})$, $-R^{30}-N(R^{30})C(J)R^{34}$, $-R^{30}-N(R^{31})C(J)OR^{31}$, $-R^{30}-N(R^{31})C(J)N(R^{32})(R^{33})$, $-R^{30}-OC(J)R^{34}$, $-R^{30}-OC(J)OR^{31}$, $-R^{30}-OC(J)N(R^{32})(R^{33})$, $-Si(R^{35})_3$, $-N(R^{31})S(O)_yR^{36}$ or $-R^{30}-S(O)_yR^{31}$;

where each $R^{30}$ is independently a direct bond or a straight or branched alkylene chain;

$R^{31}$ and $R^{34}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{32}$ and $R^{33}$ together with the nitrogen atom to which they are attached, form a heterocyclyl, heterocyclylalkenyl, or heteroaryl;

$R^{35}$ $R^{36}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each y is independently 0 to 2.

In a preferred embodiment, $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0 to 2; p is 0 to 2; X is $N(R^7)$, O, or $S(O)_r$ where r is 0 or 2;

$R^1$ is each independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^3$ is independently selected from the group consisting of hydrogen, halo, pseudohalo, cyano, nitro, hydroxy, formyl, mercapto, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

23

$R^4$ selected from the group consisting of hydrogen, halo, pseudohalo, cyano, nitro, hydroxy, formyl, mercapto, optionally substituted alky, optionally substituted aryl, optionally substituted aralkyl, optionally substituted heteroaryl, optionally substituted heteroaralkyl, $—R^{12}—OR^{13}$, $—R^{12}—N(R^{14})R^{15}$, $—R^{12}—C(O)R^{13}$, $—R^{12}—C(O)R^{15}$, $—R^{12}—C(O)N(R^{14})R^{15}$, $—R^{12}—N(R^{14})C(O)R^{15}$, and $—R^{12}—S(O)_tR^{15}$;

each $R^5$ independently selected from the group consisting of, halo, pseudohalo, cyano, nitro, hydroxy, thia, nitrile, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, $—OR^{20}$, $—S(O)_tR^{20}$, $—N(R^7)R^{20}$, $—N(R^9)S(O)_tR^{20}$, $—C(O)R^{20}$, and $—C(O)OR^{20}$;

$R^7$ and $R^9$ are each independently H or optionally substituted alkyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo, $—R^{30}—OR31$, $—R^{30}—SR^{16}$, $—R^{30}—N(R^{32})(R^{33})$, $—R^{30}—C(J)R^{34}$, $—R^{30}—C(J)OR^{31}$, $—R^{30}—C(J)N(R^{32})(R^{33})$, $—R^{30}—C(J)N(R^{31})N(R^{32})(R^{33})$, $—R^{30}—N(R^{31})C(J)R^{34}$, $—R^{30}—N(R^{31})C(J)OR^{31}$, $—R^{30}—N(R^{31})C(J)N(R^{32})(R^{33})$, $—R^{30}—OC(J)R^{34}$, $—R^{30}—OC(J)OR^{31}$, $—R^{30}—OC(J)N(R^{32})(R^{33})$, $—Si(R^{35})_3$, $—N(R^{31})S(O)_yR^{36}$ or $—R^{30}—S(O)_yR^{36}$;

where each $R^{30}$ is independently a direct bond or a straight or branched alkylene chain;

$R^{31}$ and $R^{34}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{32}$ and $R^{33}$ together with the nitrogen atom to which they are attached, form a heterocyclyl, heterocyclylalkenyl, or heteroaryl;

$R^{35}$ $R^{36}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each y is independently 0 to 2.

In a preferred embodiment, $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0 to 2; p is 0 to 2; X is $N(R^7)$, O, or $S(O)_r$ where r is 0 or 2;

$R^1$ is each independently selected from the group consisting of halo, pseudohalo, cyano, nitro, hydroxy, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^3$ is independently selected from the group consisting of hydrogen, halo, pseudohalo, cyano, nitro, hydroxy, formyl, mercapto, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^4$ selected from the group consisting of hydrogen, halo, pseudohalo, cyano, nitro, hydroxy, formyl, mercapto, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl optionally substituted heterocyclylalkyl, $—R^{12}—OR^{13}$, $—R^{12}—N(R^{14})R^{15}$, $—R^{12}—C(O)R^{13}$, $—R^{12}—C(O)OR^{15}$, $—R^{12}—C(O)N(R^{14})R^{15}$, $—R^{12}—N(R^{14})C(O)R^{15}$, $—R^{12}—N(R^{14})C(O)OR^{15}$, $—R^{12}—S(O)_tR^{15}$ and $—R^{12}—S(O)_tN(R^{14})R^{15}$;

each $R^5$ independently selected from the group consisting of halo, cyano, nitro, hydroxy, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, $—OR^{20}$, $—S(O)_tR^{20}$, $—N(R^7)R^{20}$, $—C(O)R^{20}$, and $—C(O)OR^{20}$;

$R^7$ and $R^9$ are each independently H or optionally substituted alkyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo, $—R30-OR31$, $—R^{30}—SR^{16}$, $—R^{30}—N(R^{32})(R^{33})$, $—R^{30}—C(J)R^{34}$, $—R^{30}—C(J)OR^{31}$, $—R^{30}—C(J)N(R^{32})(R^{33})$, $—R^{30}—C(J)N(R^{31})N(R^{32})(R^{33})$, $—R^{30}—N(R^{31})C(J)R^{34}$, $—R^{30}—N(R^{31})C(J)OR^{31}$, $—R^{30}—N(R^{31})C(J)N$ $(R^{32})(R^{33})$, $-R^{30}-OC(J)R^{34}$, $-R^{30}-OC(J)OR^{31}$, $-R^{30}-OC(J)N(R^{32})(R^{33})$, $-Si(R^{35})_3$, $-N(R^{31})S(O)_y R^{36}$ or $-R^{30}-S(O)_y R^{36}$;

where each $R^{30}$ is independently a direct bond or a straight or branched alkylene chain;

$R^{31}$ and $R^{34}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

or $R^{32}$ and $R^{33}$ together with the nitrogen atom to which they are attached, form a heterocyclyl, heterocyclylalkenyl, or heteroaryl;

$R^{35}$ $R^{36}$ and $R^{16}$ are each independently alkyl, alkenyl, alkynyl, haloalkyl, alkoalkenyl, cycloalkyl, cycloalkylalkyl, heterocyclyl, heterocyclylalkyl, aryl, aralkyl, heteroaryl or heteroaralkyl;

each J is independently O or S; and each y is independently 0 to 2.

In a preferred embodiment, $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0 or 1; p is 1 to 2; X is $N(R^7)$;

$R^1$ is each independently selected from the group consisting of halo, pseudohalo, cyano, nitro, hydroxy, hydroxycarbonyl, optionally substituted alkyl, alkoxy, and aminoalkyl;

$R^3$ is independently selected from the group consisting of hydrogen, halo, pseudohalo, cyano, nitro, hydroxy, formyl, mercapto, optionally substituted lower alkyl, optionally substituted lower alkenyl, optionally substituted lower alkynyl, lower alkoxy, and optionally substituted lower aminoalkyl;

$R^4$ selected from the group consisting of hydrogen, halo, pseudohalo, cyano, nitro, hydroxy, formyl, mercapto, optionally substituted alky, optionally substituted aryl, optionally substituted aralkyl, optionally substituted heteroaryl, optionally substituted heteroaralkyl, $-R^{12}-OR^{13}$, $-R^{12}-N(R^{14})R^{15}$, $-R^{12}-C(O)R^{13}$, $R^{12}-C(O)OR^{15}$, $-R^{12}-C(O)N(R^{14})R^{15}$, $-R^{12}-N(R^{14})C(O)R^{15}$, and $-R^{12}-S(O)_t R^{15}$;

each $R^5$ independently selected from the group consisting of halo, cyano, nitro, hydroxy, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, $-OR^{20}$, $-S(O)_t R^{20}$, $-N(R^7)R^{20}$, $-C(O)R^{20}$, and $-C(O)OR^{20}$;

$R^7$ and $R^9$ are each independently H or optionally substituted alkyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0 or 1; p is 1 to 2; X is $S(O)_r$ where r is 0;

$R^1$ is each independently selected from the group consisting of halo, pseudohalo, cyano, nitro, hydroxy, hydroxycarbonyl, and optionally substituted alkyl, alkoxy, and aminoalkyl;

$R^3$ is independently selected from the group consisting of hydrogen, halo, pseudohalo, cyano, nitro, hydroxy, formyl, mercapto, optionally substituted lower alkyl, optionally substituted lower alkenyl, optionally substituted lower alkynyl, lower alkoxy, and lower aminoalkyl;

$R^4$ selected from the group consisting of hydrogen, halo, pseudohalo, cyano, nitro, hydroxy, formyl, mercapto, optionally substituted alky, optionally substituted aryl, optionally substituted aralkyl, optionally substituted heteroaryl, optionally substituted heteroaralkyl, $-R^{12}-OR^{13}$, $-R^{12}-N(R^{14})R^{15}$, $-R^{12}-C(O)R^{13}$, $-R^{12}-C(O)OR^{15}$, $-R^{12}-C(O)N(R^{14})R^{15}$, $-R^{12}-N(R^{14})C(O)R^{15}$, and $-R^{12}-S(O)_t R^{15}$;

each $R^5$ independently selected from the group consisting of halo, cyano, nitro, hydroxy, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, $-OR^{20}$, $-S(O)_t R^{20}$, $-N(R^7)R^{20}$, $-C(O)R^{20}$, and $-C(O)OR^{20}$;

$R^7$ and $R^9$ are each independently H or optionally substituted alkyl;

$R^{12}$ represents a $C_1$-$C_6$ alkyl, $C_1$-$C_6$ alkenyl, $C_1$-$C_6$ alkynyl or $C_1$-$C_6$ alkoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0 or 1; p is 1 to 2; X is O;

R¹ is each independently selected from the group consisting of halo, pseudohalo, cyano, nitro, hydroxy, hydroxycarbonyl, and optionally substituted alkyl, alkoxy, and aminoalkyl;

R³ is independently selected from the group consisting of hydrogen, halo, pseudohalo, cyano, nitro, hydroxy, formyl, mercapto, optionally substituted lower alkyl, optionally substituted lower alkenyl, optionally substituted lower alkynyl, lower alkoxy, and lower aminoalkyl;

R⁴ selected from the group consisting of hydrogen, halo, pseudohalo, cyano, nitro, hydroxy, formyl, mercapto, optionally substituted alky, optionally substituted aryl, optionally substituted aralkyl, optionally substituted heteroaryl, optionally substituted heteroaralkyl, $-R^{12}-OR^{13}$, $-R^{12}-N(R^{14})R^{15}$, $-R^{12}-C(O)R^{13}$, $-R^{12}-C(O)OR^{15}$, $-R^{12}-C(O)N(R^{14})R^{15}$, $-R^{12}-N(R^{14})C(O)R^{15}$, and $-R^{12}-S(O)_tR^{15}$;

each R⁵ independently selected from the group consisting of halo, cyano, nitro, hydroxy, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, $-OR^{20}$, $-S(O)_tR^{20}$, $-N(R^7)R^{20}$, $-C(O)R^{20}$, and $-C(O)OR^{20}$;

R⁷ and R⁹ are each independently H or optionally substituted alkyl;

R¹² represents a $C_1$-$C_6$ alkyl, $C_1$-$C_6$ alkenyl, $C_1$-$C_6$ alkynyl or $C_1$-$C_6$ alkoxy represents H or optionally substituted alkyl;

R¹³ represents optionally substituted alkyl, optionally substituted aryl, optionally substituted aralkyl or optionally substituted heterocyclyl;

R¹⁴ represents H or optionally substituted alkyl;

R¹⁵ represents optionally substituted alkyl, optionally substituted aryl, optionally substituted aralkyl or optionally substituted heterocyclyl;

R²⁰ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Another preferred set of compounds of formula (II) are those in which;

n is 0 or 1; p is 1 to 2; X is S(O), where r is 2;

R¹ is each independently selected from the group consisting of halo, pseudohalo, cyano, nitro, hydroxy, hydroxycarbonyl, and optionally substituted alkyl, alkoxy, and aminoalkyl;

R³ is independently selected from the group consisting of hydrogen, halo, pseudohalo, cyano, nitro, hydroxy, formyl, mercapto, optionally substituted lower alkyl, optionally substituted lower alkenyl, optionally substituted lower alkynyl, lower alkoxy, and lower aminoalkyl;

R⁴ selected from the group consisting of hydrogen, halo, pseudohalo, cyano, nitro, hydroxyl, formyl, mercapto, optionally substituted alky, optionally substituted aryl, optionally substituted aralkyl, optionally substituted heteroaryl, optionally substituted heteroaralkyl, $-R^{12}-OR^{13}$, $-R^{12}-N(R^{14})R^{15}$, $-R^{12}-C(O)R^{13}$, $-R^{12}-C(O)R^{15}$, $-R^{12}-C(O)N(R^{14})R^{15}$, $-R^{12}-N(R^{14})C(O)R^{15}$, and $-R^{12}-S(O)_tR^{15}$;

each R⁵ independently selected from the group consisting of halo, cyano, nitro, hydroxy, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, $-OR^{20}$, $-S(O)_tR^{20}$, $-N(R^7)R^{20}$, $-C(O)R^{20}$, and $-C(O)OR^{20}$;

R⁷ and R⁹ are each independently H or optionally substituted alkyl;

R¹² represents a $C_1$-$C_6$ alkyl, $C_1$-$C_6$ alkenyl, $C_1$-$C_6$ alkynyl or $C_1$-$C_6$ alkoxy;

R¹³ represents optionally substituted alkyl, optionally substituted aryl, optionally substituted aralkyl or optionally substituted heterocyclyl;

R¹⁴ represents H or optionally substituted alkyl;

R¹⁵ represents optionally substituted alkyl, optionally substituted aryl, optionally substituted aralkyl or optionally substituted heterocyclyl;

R²⁰ represents optionally substituted alkyl, optionally substituted aryl, optionally substituted aralkyl or optionally substituted heterocyclyl; and where each t is independently 0 to 2.

In one embodiment, the substituents, when substituted, are independently substituted with a group selected from $Q^1$, where $Q^1$ represents alkyl, alkoxy, aminoalkyl, haloalkyl, cycloalkyl, cycloalkylalkyl, heterocyclyl, heterocyclylalkyl, aryl, aralkyl, heteroaryl, heteroaralkyl, cyano, nitro, halo, hydroxyl, hydroxycarbonyl or pseudohalo.

Methods of Preparation

The following illustrations depict general preparations of compounds claimed herein and consist of reactions typically known to one skilled in the art of chemical synthesis. The following references are provided as supporting information: Joule et al. (1995) *Heterocyclic Chemistry*, 3ʳᵈ Ed., Chapman & Hall, London, UK; Katritzky et al. (1984) *Comprehensive Heterocyclic Chemistry*, Pergamon Press, Oxford, UK; Katritzky et al. (2000) *Handbook of Heterocyclic Chemistry*, 2ⁿᵈ Ed., Pergamon Press, Oxford, UK; March (1992) *Advanced Organic Chemistry*, 4ᵗʰ Ed.; John Wiley, New York. Starting materials in the synthesis examples provided herein are either available from commercial sources of via literature procedures. The substituents R¹-R¹⁰, R¹²-R¹⁵, R²⁰ and X, as well as n, p and t have been previously described. Also it will be apparent to one skilled in the art that the substituents, when present, could exist as one or more isomers, that is E/Z isomers, enantiomers and/or diastereomers.

In general, compounds of Formula I are substituted 2-phenylpyrimidines (3), and can be prepared via condensation of a substituted benzamidine (1) with an appropriately substituted 1,3-diketo compound (2) as depicted in Scheme 1. These types of reactions are usually performed in an alcoholic solvent with the presence of a base.

Scheme 1

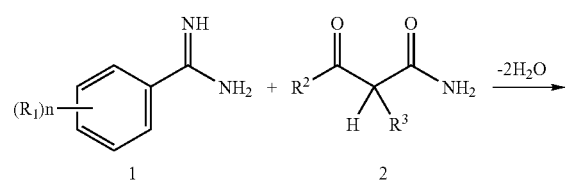

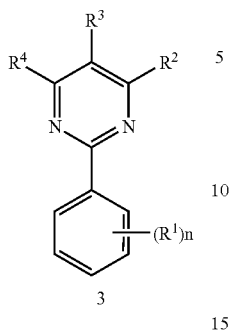

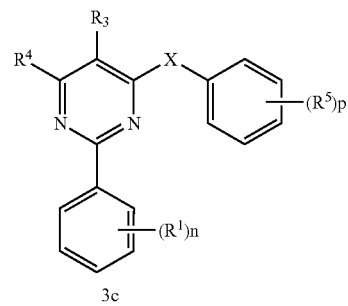

More specifically, compounds of Formula II (3c) can be prepared according to Scheme 2. A substituted benzamidine (1) can be condensed with an appropriately substituted 3-keto ester (2a) in the presence of a base. Treatment of 3a with a halogenating agent such as $POCl_3$ provides 3b, which can be reacted with appropriately substituted anilines (X=N(R$^7$)), phenols (X=O) or thiophenols (X=S) in the presence of a base to give the desired 3c. When X=S, the resulting product can be oxidized with an appropriate oxidizing agent (such as $H_2O_2$) to a sulfoxide (X=SO) or a sulfone (X=SO$_2$).

Instead of being incorporated from 1,3-diketo compounds 2, the substituents $R^2$, $R^3$ and $R^4$ can also be varied by forming the appropriate halogenated compound (3b, 3d or 3e, Scheme 2 and 3) and reacting it with various nucleophiles, such as a grignard reagents, cyanides, alcohols, amines, thiols, and others as shown in scheme 4. Also, reactions such as Stille, Suzuki or Heck couplings or treatment with a suitable lithiating agent followed by an electrophile can also be performed on these halogenated compounds as shown in Scheme 4.

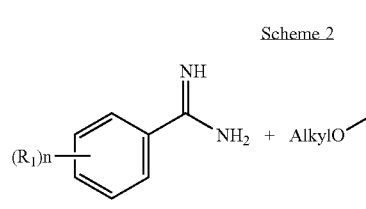

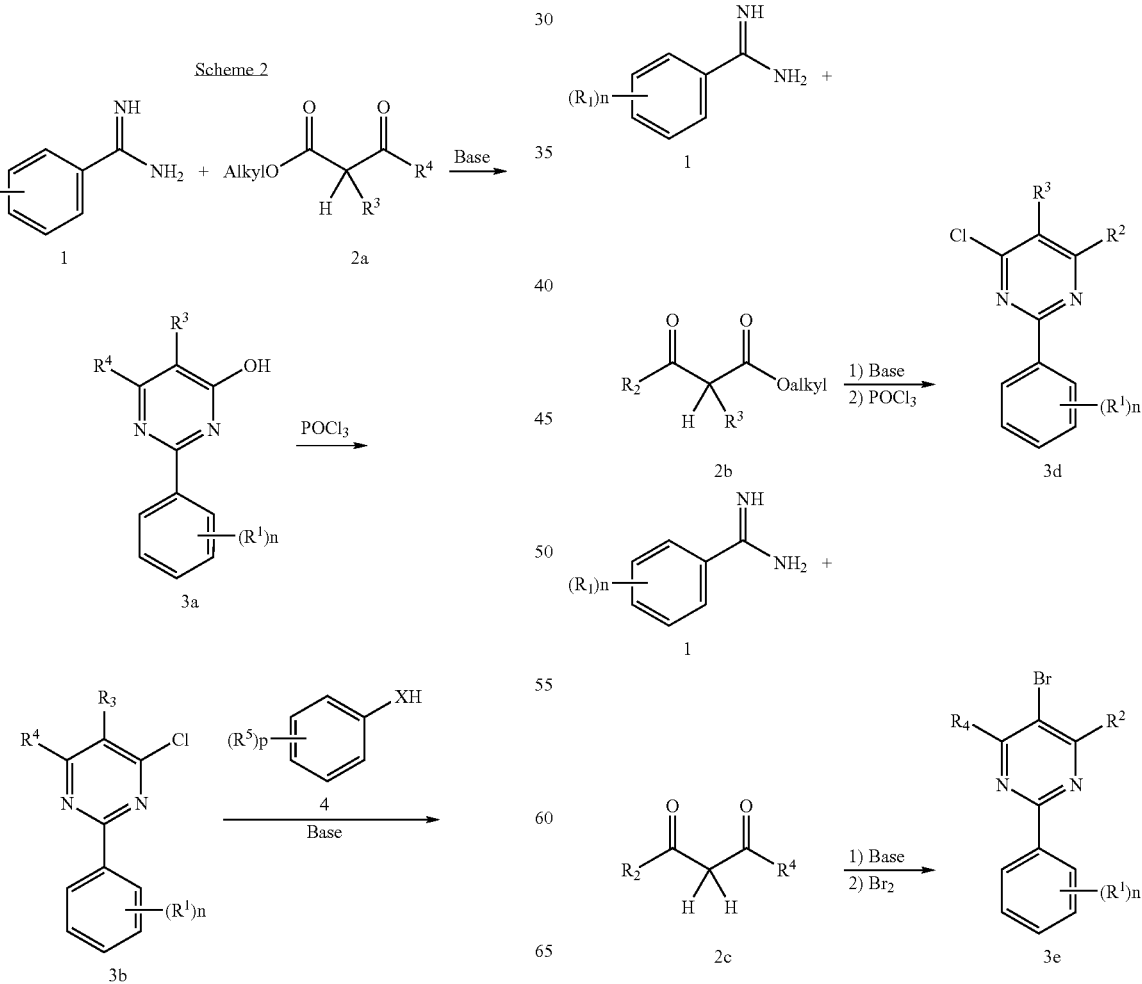

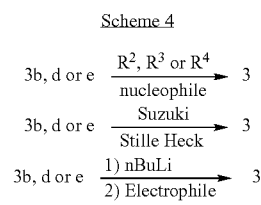

Scheme 4

Formulation of Pharmaceutical Compositions

The pharmaceutical compositions provided herein contain therapeutically effective amounts of one or more of the nuclear receptor activity modulators provided herein that are useful in the prevention, treatment, or amelioration of one or more of the symptoms of diseases or disorders associated with nuclear receptor activity, including the NGFI-B family. Such diseases or disorders include, but are not limited to, Parkinson's disease, cancer, Alzheimer's disease, schizophrenia, manic depressive illness, multiple sclerosis, neuronal inflammatory responses, neuronal injury, stroke, neuronal degeneration, inflammation, acute inflammatory reactions, osteoporosis, arthritis, rheumatoid arthritis, psoriatic arthritis, sarcoid arthritis, osteoarthritis, ulcerative colitis, thyrroiditis, atherosclerosis, and atherosclosis related cardiovascular and coronary heart disease.

Further the pharmaceutical compositions provided herein contain therapeutically effective amounts of one or more of the nuclear receptor activity modulators provided herein that are useful in the prevention, treatment, or amelioration of one or more of the symptoms of diseases or disorders that are not directly associated with a nuclear receptor, but for which a complication of the disease or disorder is treatable with claimed compounds and compositions.

The pharmaceutical compositions contain one or more compounds provided herein. In one aspect such pharmaceutical compositions comprise one or more of the claimed compounds modified to a pharmaceutical derivative or to a prodrug form. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In the pharmaceutical compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with nuclear receptor activity or in which nuclear receptor activity is implicated.

Such diseases or disorders include, but are not limited to, Parkinson's disease, cancer, Alzheimer's disease, schizophrenia, manic depressive illness, multiple sclerosis, neuronal inflammatory responses, neuronal injury, stroke, neuronal degeneration, inflammation, acute inflammatory reactions, osteoporosis, arthritis, rheumatoid arthritis, psoriatic arthritis, sarcoid arthritis, osteoarthritis, ulcerative colitis, thyrroiditis, atherosclerosis, and atherosclosis related cardiovascular and coronary heart disease.

Typically, the pharmaceutical compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the pharmaceutical composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in International Patent Application Publication Nos. 99/27365 and 00/25134 and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with nuclear receptor activity or in which nuclear receptor activity is implicated, as described herein.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with nuclear receptor activity or in which nuclear receptor activity is implicated, as described herein. The concentration of active compound in the composition will depend on absorption, inactivation, excretion rates of the active compound, the dosage schedule, amount administered, particular formulation as well as other factors known to those of skill in the art.

The pharmaceutical compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or single or multiple dose vials made of glass, plastic or other suitable material. In instances in which the compounds exhibit insufficient solubility, methods for solubilizing compounds may be used. Such methods are known to those of skill in this art, and include, but are not limited to, using co-solvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The pharmaceutical composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings. The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with nuclear receptor activity or in which nuclear receptor activity is implicated. It is to be understood that such combination therapy constitutes a further aspect of the compositions and methods of treatment provided herein.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It, is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Compositions for other Routes of Administration

Other routes of administration, such as topical application, transdermal patches, and rectal administration are also contemplated herein. Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Articles of Manufacture

The compounds or pharmaceutically acceptable derivatives may be packaged as articles of manufacture comprising packaging material, a compound or composition of the present invention or a pharmaceutically acceptable derivative thereof provided herein within the packaging material, and a label that indicates that the compound or composition, or pharmaceutically acceptable derivative thereof, is used for modulating the activity of one or more nuclear receptors, including the NGFI-B family, or for treatment, prevention or amelioration of one or more symptoms of a diseases or disorders.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which nuclear receptor activity, including the NGFI-B family, are implicated as a mediator or contributor to the symptoms or cause.

Evaluation of the Utility of the Compounds of the Invention

Those of skill in the art recognize that various methods may be used to characterize and profile the activity of the claimed compounds and compositions. Preferably such compounds exhibit an $EC_{50}$ of 2000 nM or less for a NGFI-B/RXR heterodimer in one of the in vivo or in vitro assays described herein. More preferably such compounds will not significantly (less than about 10% of maximal activation) activate RXR alone or other nuclear receptor/RXR heterodimer complexes, in one of the in vivo or in vitro assays described herein at a concentration equivalent to the $EC_{50}$ value for the interaction of the compound with the NGFI-B/RXR heterodimer.

Suitable cell based assays for assaying the activity of the claimed compounds include, but are not limited to, the cotransfection assay, the use of LBD-Gal 4 chimeras and protein-protein interaction assays (see, for example, Lehmann. et al., *J. Biol Chem.* (1997), Vol. 272, No. 6, pp. 3137-3140).

In addition many biochemical screening formats exist for screening compound activities to identify high affinity ligands which include, but are not limited to, direct binding assays, ELISAs, fluorescence polarization (FP) assays, and fluorescence resonance energy transfer energy transfer (FRET) and time resolved FRET based coactivator recruitment assays (see, generally, Glickman et al., *J. Biomolecular Screening* (2002), Vol. 7, No. 1, pp. 3-10).

Direct binding assays can be established to determine the relative binding of the claimed compounds to the RXR protein and the NGFI-B/RXR heterodimer protein complex. Binding to the RXR can be accomplished by expression of full length or ligand binding domain of human RXR in a Baculovirus or bacterial protein expression system. Binding affinity can be calculated based on competition of $^3$H-9-cis-retenoic acid from the RXR protein with the claimed compounds.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., *Biomol. Screen* (2000 October), Vol. 5, No. 5, pp. 297), scintillation proximity assays (SPA) (see, for example, Carpenter et al., *Methods Mol. Biol.* (2002), Vol 190, pp. 31-49) and fluorescence resonance energy transfer energy transfer (FRET) or time resolved FRET based coactivator recruitment assays (Mukherjee et al., *J. Steroid Biochem. Mol. Biol.* (2002 July); Vol. 81, No. 3, pp. 217-25; (Zhou et al., *Mol. Endocrinol.* (1998 October), Vol. 12, No. 10, pp. 1594-604).

Methods of performing assays on fluorescent materials are well known in the art and are described in, e.g., Lakowicz, J. R., *Principles of Fluorescence Spectroscopy*, New York: Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y. L., San Diego: Academic Press (1989), pp. 219-243; Turro, N. J., *Modern Molecular Photochemistry*, Menlo Park: Benjamin/Cummings Publishing Col, Inc. (1978), pp. 296-361.

Fluorescence in a sample can be measured using a fluorimeter, a fluorescent microscope or a fluorescent plate reader. In general, all of these systems have an excitation light source which can be manipulated to create a light source with a defined wavelength maxima and band width which passes through excitation optics to excite the sample.

Typically the excitation wavelength is designed to selectively excite the fluorescent sample within its excitation or absorption spectrum. For most FRET based assays the excitation wavelength is usually selected to enable efficient excitation of the donor while minimizing direct excitation of the acceptor. In response the sample (if fluorescent) emits radiation that has a wavelength that is different from the excitation wavelength. Collection optics then collect the emission from the sample, and direct it to one or more detectors, such as photomultiplier tubes or CCD cameras. Preferably the detector will include a filter to select specific wavelengths of light to monitor. For time resolved applications, for example time resolved FRET, the excitation and or emission optical paths include control mechanisms to precisely terminate illumination and then to wait for a precise period of time before collecting emitted light. By using compounds such as lanthanides that exhibit relatively long-lived light emission it is possible to gain significant enhancements in detection sensitivity and accuracy.

The detection devices can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, autofocusing feature, and electronics associated with imaging and data collection can be managed by an appropriately programmed digital computer. The computer also can transform the data collected during the assay into another format for presentation.

Suitable instrumentation for fluorescence microplate readers include without limitation the CytoFluor™ 4000 available from PerSeptive Biosystems. For 96-well based assays black walled plates with clear bottoms, such as those manufactured by Costar are preferred.

Suitable instrumentation for luminescence measurements include standard liquid scintillation plate readers, including without limitation the Wallac Microbeta, or PE Biosystems Northstar, or equivalents commercially available from Packard, Perkin Elmer and a number of other manufacturers.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, a radiolabelled ligand such as tritiated 9-cis-retinoic acid (Amersham) generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of a nuclear receptor can also be measured by fluorescence resonance energy transfer (FRET), or time resolved FRET, to monitor the ability of the compounds provided herein to bind to the nuclear receptor. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of lanthanide labeled streptavidin (Wallac Inc.), and the purified LBD of RXR, is labeled with a suitable fluorophore such as CY5™. Equimolar amounts of each modified LBD are mixed together and allowed to equilibrate for at least 1 hour prior to addition to either variable or constant concentrations of the test compound for which the activity is to be determined. After equilibration, the time-resolved fluorescent signal is quantitated using a fluorescent plate reader. The activity of the test compound can then be estimated from a plot of fluorescence versus concentration of test compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant epitope, or affinity tagged nuclear receptor ligand binding domain (LBD) fusion protein and a synthetic biotinylated peptide derived from the receptor interacting domain (-LXXLL motif) of a co-activator peptide such as the steroid receptor coactivator 1 (SRC-1), TIF2, DRIP1 or AIB1. Typically the tagged-LBD is labeled with a lanthanide chelate such as europium (Eu), via the use of antibody specific for the tag, and the co-activator peptide is labeled with allophycocyanin via a streptavidin-biotin linkage. Such labeling protocols are well known in the art, and are readily available in kit form, for example based on the DELFIA® assay system from Perkin Elmer, (MA).

In the presence of an agonist for the nuclear receptor, the peptide is recruited to the tagged-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit the activity of an agonist for the nuclear receptor.

In addition, a variety of cell based assay methodologies may be successfully used in screening assays to identify and profile the affinity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor. (See for example U.S. Pat. Nos. 5,071, 773; 5,298,429 and 6,416,957). Treatment of the transfected cells with an agonist for the nuclear receptor increases the transcriptional activity of that receptor which is reflected by an increase in expression of the reporter gene which may be measured by a variety of standard procedures.

In one embodiment of this method the host cell endogenously expresses the nuclear receptor heterodimer (typically with RXR) and appropriate co-factors. Typically such a situation may occur with a primary cell or cell lines derived directly from a primary cell type, is used to characterize compounds of the present invention. Accordingly creation of the assay system requires the transfection into the cell of a suitable reporter gene(s) as are described herein. Alternatively the expression of endogenous gene can be used to monitor NGFI-B family transcriptional activity in response to the addition of a test compound.

In another aspect the host cell may lack sufficient endogenous expression of a suitable nuclear receptor, in which case one may be introduced by transfection of the cell line with an expression plasmid, as described below.

Typically, the expression plasmid comprises: (1) a promoter, such as an SV40 early region promoter, HSV tk promoter or phosphoglycerate kinase (pgk) promoter, CMV promoter, Srα promoter or other suitable control elements known in the art, (2) a cloned polynucleotide sequence, such as a cDNA encoding a receptor, co-factor, or fragment thereof, ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. Genes & Development 9 1033-1045 (1995)) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example see U.S. Pat. Nos. 6,534,261 and 6,503,7171) or a strong promoter or enhancer sequence together with a targeting sequence to enable homologous or non-homologous recombination of the activating sequence upstream of the gene of interest.

In one aspect of these methods, full-length genes encoding the complete cDNA sequence of NGFI-B α (Accession No XM_083884), NGFI-B β (Accession No NM_006186) and NGFI-B γ (XM_037370).

In another embodiment of these methods chimeras of these full-length genes are used in place of the full-length nuclear receptor. Such chimeras typically comprise the ligand binding domain (amino acids 353-598) of the human Nurr1 coupled to a heterologous DNA binding domain (DBD). Such chimeras additionally comprise the ligand binding domain (amino acids 222-462) of the human RXRalpha coupled to a heterologous DNA binding domain (DBD).

Typically for such chimeric constructs, heterologous DNA binding domains from distinct, well-defined nuclear receptors are used, for example including without limitation, the DBDs of the glucocorticoid receptor, GR (accession no. NM_000176) (amino acids 421-486), mineralocorticoid receptor, MR (accession no. NM_055775) (amino acids 603-668), androgen receptor, AR (accession no XM_010429NM_055775) (amino acids 929-1004), progesterone receptor, PR (amino acids 622-695), and estrogen receptor alpha, ERα (accession no. XM_045967) (amino acids 185-250).

Alternatively DNA binding domains from yeast or bacterially derived transcriptional regulators such as members of the GAL 4 and Lex A (GenBank accession number ILEC)/Umud super families may be used.

GAL4 (GenBank Accession Number P04386,) is a positive regulator for the expression of the galactose-induced genes. (see for example, Keegan et al., Science 231: 699-704 (1986)). Preferably the first 96 amino acids of the Gal4 protein are used, most preferably the first 147 amino acid residues of yeast Gal4 protein are used.

For those receptors that can function as heterodimers with RXR, such as the Nurr1, the method typically includes the use of expression plasmids for both the nuclear receptor of interest and RXR. Such sequences include, but are not limited to the following members of the RXR gene family, including RXRα (GenBank Accession No. NM_002957), RXRβ (GenBank Accession No. XM_042579) and RXRγ (GenBank Accession No. XM_053680).

To identify compounds that act to modulate co-factor, or nuclear receptor heterodimerization, a mammalian two-hybrid assay can be used (see, for example, U.S. Pat. Nos. 5,667,973, 5,283,173 and 5,468,614). This approach identifies protein-protein interactions in vivo through reconstitution of a strong transcriptional activator upon the interaction of two proteins, a "bait" and "prey" (Fields S and Song O (1989) Nature 340: 245; Willey et al., (1995) Gene & Development 9 1033-1045).

This system relies on functional dimeric interactions between two fusion proteins, one carrying the GAL4 DNA-binding domain fusion with the ability to bind to a GAL4$_{UAS}$-containing reporter gene. The other carries the VP16 transactivation domain fusion. When expressed together, DNA binding and transcriptional activation is reconstituted in a single complex. Functional interaction, for example between a GAL4-SRC-1 fusion protein and VP16-RXR fusion protein should lead to constitutive activation of a suitable reporter plasmid, such as luciferase reporter construct comprising GAL4 Upstream Activating Sequences (UAS).

Such reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., (1987) Mol. Cell. Biol. 7 725-735) down stream from the herpes virus thymidine kinase promoter (located at nucleotides residues −105 to +51 of the thymidine kinase nucleotide sequence, pBLCAT2 (Luckow & Schutz (1987) Nucl.

Acid. Res. 15 5490-5494)) which is linked in turn to the appropriate response elements.

Transactivation domains are well known in the art and can be readily identified by the artisan. Examples include the GAL4 activation domain, TAT, VP16, and analogs thereof.

Response elements are well known and have been thoroughly described in the art. Such response elements can include direct repeat structures or inverted repeat structures based on well defined hexad half sites, as described in greater detail below. Exemplary hormone response elements are composed of at least one direct repeat of two or more half sites, separated by a spacer having in the range of 0 up to 6 nucleotides. The spacer nucleotides can be randomly selected from any one of A, C, G or T. Each half site of response elements contemplated for use in the practice of the invention comprises the sequence: -RGBNNM-, wherein R is selected from A or G; B is selected from G, C, or T; each N is independently selected from A, T, C, or G; and M is selected from A or C; is with the proviso that at least 4 nucleotides of said -RGBNNM- sequence are identical with the nucleotides at corresponding positions of the sequence -AGGTCA-. Response elements employed to profile the compounds of the present invention can optionally be preceded by N, wherein x falls in the range of 0 up to 5. Preferred response elements useful in the methods of the present invention include DR5 types response elements.

The choice of hormone response element is dependent upon the type of assay to be used. In the case of the use of the full length NGFI-B β, (Nurr1) a known Nurr1 RE would typically be used. In the case of the use of the full length Nurr1 with full length RXR, a known Nurr1/RXR heterodimer response element such as a DR5 element would typically be used. In the case of a Nurr1-LBD-Gal4 fusion, a GAL4 UAS would be used. Typically the GAL4 UAS would comprise the sequence 5'CGGRNNRCYNYNCNCCG-3', where Y=C or T, R=A or G, and N=A, C, T or G, and would be present as a tandem repeat of 4 copies.

Numerous reporter gene systems are known in the art and include, for example, alkaline phosphatase (see, Berger, J., et al., *Gene* (1988), Vol. 66, pp. 1-10; and Kain, S. R., *Methods. Mol. Biol.* (1997), Vol. 63, pp. 49-60), β-galactosidase (See, U.S. Pat. No. 5,070,012, issued Dec. 3, 1991 to Nolan et al., and Bronstein, I., et al., *J. Chemilum. Biolum.* (1989), Vol. 4, pp. 99-111), chloramphenicol acetyltransferase (See, Gorman et al., *Mol. Cell Biol.* (1982), Vol. 2, pp. 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., *Annu. Rev. Biochem.* (1998), Vol. 67, pp. 509-44).

Numerous methods of co-transfecting the expression and reporter plasmids are known to those of skill in the art and may be used for the co-transfection assay to introduce the plasmids into a suitable cell type.

These screening approaches enable the selection of compounds that interact with the NGFI-B/RXR heterodimer complexes, preferably such as NGFI-Bβ/RXR, with high affinity. Preferably such compounds exhibit an affinity, as measured via any of the methods disclosed herein, of at least 1000 nM, preferably at least 500 nM, more preferably at least 100 nM, and most preferably at least 50 nM. In one aspect preferred compounds should exhibit at least a 10 fold separation of NGFI-B/RXR heterodimer activation compared to other nuclear/RXR heterodimer complexes, such as for example, RAR/RXR, ER/RXR FXR/RXR. More preferably such compounds would exhibit at least a 50 fold separation, and most preferable would be at least a 100 fold separation.

Any compound which is a candidate for activation of NGFI-B/RXR may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by Nurr1, RXR or Nurr1/RXR heterodimer and other nuclear receptors in vivo, using Northern-blot, RT PCR or oligonucleotide microarray analysis to analyze RNA levels. Western-blot analysis can be used to measure expression of proteins encoded by Nurr1, RXR or Nurr1/RXR target genes.

Established animal models exist for a number of diseases of direct relevance to the claimed compounds and these can be used to further profile and characterize the claimed compounds. Additionally Nurr1 or RXR animal models (e.g., knockout mice) can be used to further evaluate the present compounds and compositions in vivo.

Methods of Use of the Compounds and Compositions

Methods of use of the compounds and compositions provided herein are also provided.

The methods involve both in vitro and in vivo uses of the compounds and compositions for altering nuclear receptor activity, including the NGFI-B family and or RXR/NGFI-B heterodimers, for the treatment, prevention, or amelioration of one or more symptoms of diseases or disorder that are modulated by nuclear receptor activity, including the NGFI-B family, or in which nuclear receptor activity, including the NGFI-B family is implicated. Such compounds or compositions will typically exhibit agonist, partial agonist, partial antagonist or antagonist activity against the NGFI-B family in one of the in vitro assays described herein. Preferably such compounds and compositions will modulate the activity of NGFI-Bβ/RXR activity.

Methods of altering nuclear receptor activity, including the NGFI-B family and or their corresponding RXR heterodimers, by contacting the receptor with one or more compounds or compositions provided herein, are provided.

Methods of treatment, prevention, or amelioration of one or more symptoms of a disease or disorder in which NGFI-B family activity is implicated are provided, including without limitation Parkinson's disease, cancer, Alzheimer's disease, schizophrenia, manic depressive illness, multiple sclerosis, neuronal inflammatory responses, neuronal injury, stroke, neuronal degeneration, inflammation, acute inflammatory reactions, osteoporosis, arthritis, rheumatoid arthritis, psoriatic arthritis, sarcoid arthritis, osteoarthritis, ulcerative colitis, thyrroiditis, atherosclerosis, and atherosclerosis related cardiovascular and coronary heart disease by administering a compound or composition of the present invention to patient in need of such treatment.

Methods are provided for the treatment, prevention, or amelioration of one or more complications of diseases in which NGFI-B family activity is implicated including without limitation Parkinson's disease, cancer, Alzheimer's disease, schizophrenia, manic depressive illness, multiple sclerosis, neuronal inflammatory responses, neuronal injury, stroke, neuronal degeneration, inflammation, acute inflammatory reactions, osteoporosis, arthritis, rheumatoid arthritis, psoriatic arthritis, sarcoid arthritis, osteoarthritis, ulcerative colitis, thyrroiditis, atherosclerosis, and atherosclosis related cardiovascular and coronary heart disease by administering a compound or composition of the present invention to patient in need of such treatment.

Methods are provided for regulating the activity of NGFI-B β/RXR heterodimers in neuronal cells, and for improving the differentiation and survival of dopaminergic neuronal cells in culture comprising incubating a stem cell with a compound or composition of the present invention. In one aspect the stem cell can comprise an embryonic stem cell, in another embodiment in can comprise a stem cell derived from an adult.

Major impediments in the use of cell transplantation therapies for the treatment of neurological disorders such as, for example, neuronal degeneration, Parkinson's disease, stroke, Alzheimer's, Huntington's disease and multiple sclerosis are the lack of an adequate supply of competent donor cells and poor viability of the cells prior to and during transplantation (Kordower et al., Mov. Disord. 13: 88-95 (Suppl.), 1998) Thus, there is a need for improved culture methods for the production of cells for transplantation, and the need for improved cell packaging methods (i.e. culture conditions and factors) or maintaining cell viability during before and during the transplantation procedure.

Accordingly, the present invention includes methods for the use of a compound or composition of the present invention for the production of neuronal cells for issue transplantation. In another aspect the present invention includes methods for the use of a compound or composition of the present invention for maintaining neuronal cell viability during before and during a transplantation procedure.

Parkinsonism is a clinical syndrome characterized by a disturbance in motor functions such as slowness of voluntary movement, diminished facial expressions, stooped posture, rigidity and tremor. The disease appears later in life. A growing body of evidence indicates that Parkinson disease is caused by genetic defects or by undefined environmental insults acting on genetically predisposed individual. Genetic factors that have been linked to familial Parkinson disease include SNCA (encoding a-synuclein;), PARK2, MAPT (encoding microtubule-associated protein tau; UCHL1 (encoding ubiquitin carboxyl-terminal esterase L1), NGFI-B β and several undefined genes that map to 1p32, 1p35, 1p36, 2p13, 4p15.7 and 12p11.2-q13.1

Experimental evidence based on knock out mice lacking NGFI-B β (Nurr 1) demonstrates that Nurr1 expression is essential for the late stages of dopaminergic neuron differentiation and survival in the ventral midbrain. In Parkinson's disease, the loss of dopaminergic neurons of the substantial nigra results in a decrease in striatal dopamine content which is proportional to the severity of the motor syndrome. Furthermore Nurr1+/− adult knock out mice show greater susceptibility to damage in response to treatment with 1-methyl-4-phenyl-1,2,3,6-tetrahydropyridine (MPTP), a neurotoxin that elicits Parkinson's disease symptoms.

These results suggest in sum that maintaining Nurr1 activity may delay or prevent onset of Parkinson's disease and according the compounds and compositions of the present invention have utility for the treatment, prevention, or amelioration of one or more symptoms of, as well as treating the complications of Parkinson's disease.

Thus, within one embodiment methods are provided for treatment, prevention, or amelioration of neurological diseases such as Parkinson's, comprising administering to a patient in need thereof of one of the compounds or compositions of the present invention.

NGFI-B expression is high within the CNS of adults and NGFI-B family members expression is induced by pro-inflammatory cytokines suggested a role for the NGFI-B family in mediating inflammatory responses in neuronal tissues. Accordingly any of the compounds of the present invention, that modulate NGFI-B/RXR heterodimers would be likely to have utility for use in the treatment, prevention or amoliration of the symptoms of Alzheimer's disease and multiple sclerosis.

Alzheimer's disease is clinically manifested as insidious impairment of higher intellectual function with alterations in mood and behavior. Later, progressive memory loss and disorientation are observed and eventually, profound disability and death. Alzheimer's disease affects a large portion of the increasingly aging population with a prevalence as high as 47% of those over 85 years old. The total costs required for formal and informal care of AD patients was $67 million in the United States. Although there is much variability, average life expectancy is 8-10 years after dementia onset.

Alzheimer's disease is characterized by the appearance of cerebral extracellular beta-amyloid deposits as senile plaques, intraneuronal neurofibrillary tangles, granulovascular degeneration and amyloid angiopathy. Senile plaques are extracellular lesions comprised of degenerating neuronal processes and abnormal deposits of beta-amyloid protein. Senile plaques range in size from 20 to 200 μm in diameter. Microglia and reactive fibrous astrocytes are enriched in the periphery of plaques, suggesting the recruitment of cells to the diseased site. These plaques are widely distributed in the cerebral cortex and can be considered to be central to the process of disease development.

Response to neuronal injury is characterized by the activation of glial cells and the expression of a number of genes that participate in the repair of damaged neurons. Some of those products include the beta-amyloid precursor protein and neurotrophins. The glial cell recruitment and responses may compromise neuronal viability by producing cytokines, reactive oxygen species and degradative enzymes. It is generally hypothesized that in local neuronal injury, an increased beta-amyloid production results in glial cell recruitment and activation which results in the production of pro-inflammatory processes and tissue destruction. Thus, it is most likely the accumulative effects of a defective repair process that results in neuronal cell death and the formation of senile plaques.

The involvement of neuronal inflammatory events in disease progression suggest that activating NGFI-B family activity may delay or prevent onset of Alzheimer's disease and according the compounds and compositions of the present invention have utility for the treatment, prevention, or amelioration of one or more symptoms of, as well as treating the complications of Alzheimer's disease.

Thus, within one embodiment methods are provided for treatment, prevention, or amelioration of neurological diseases such as Alzheimer's disease, comprising administering to a patient in need thereof of one of the compounds or compositions of the present invention.

Multiple sclerosis is the most common of the demyelinating disorders, having a prevalence of approximately 1 in 1000 persons in most of the United States and Europe. Although the etiology of multiple sclerosis (MS) is unknown, genetic, environmental and immunological factors are believed responsible for a coordinated attack on myelin. The hallmark lesion in MS is a punched-out area in which the axon is surrounded by astrocytic processes. The accompanying inflammatory reaction is characterized by infiltration of lymphocytes, monocytes and macrophages into the parenchyma of the central nervous system (CNS), analogous to the chronic inflammation in other diseases such as arthritis and psoriasis. Thus, in MS, there is increased inflammatory cell activation and infiltration, increased fibrous astrocyte activation, migration and proliferation, increased production of cytokines and matrix metalloproteinases, increased demyelination, axonal degeneration and plaque formation.

These results suggest that activating NGFI-B family activity may delay or prevent onset of multiple sclerosis by alleviating the inflammatory component of the disease, and according the compounds and compositions of the present invention have utility for the treatment, prevention, or amelioration of one or more symptoms of, as well as treating the complications of multiple sclerosis.

Thus, within one embodiment methods are provided for treatment, prevention, or amelioration of neurological diseases such as multiple sclerosis, comprising administering to a patient in need thereof of one of the compounds or compositions of the present invention.

Inflammatory immune diseases affect the immune system of an organism, causing inflammation of particular regions of the body. Examples of inflammatory immune diseases include arthritis, such as rheumatoid arthritis, psoriatic arthritis and sarcoid arthritis, osteoarthritis, ulcerative colitis and thyrroiditis. The inflammation may be a primary symptom of the disease or may be indirectly related to the disease. In a specific embodiment, the inflammation may be a low level grade of inflammation such as with a degenerative form of arthritis including osteoarthritis.

"Arthritis" as used herein means all conditions characterized by inflammation of one or more joints. Any disease or disorder associated with joint inflammation, tissue destruction, and/or degeneration of extracellular matrix structures, particularly joint cartilage and bone, may cause arthritis. Such conditions include, without limitation, rheumatoid arthritis (RA); psoriatic arthritis, infectious arthritis, juvenile rheumatoid arthritis; osteoarthritis, and spondyloarthropaties.

Symptoms of arthritis include, but are not limited to, swelling, warmth, redness of the overlying skin, pain, and restriction of motion. Arthritis can be monitored or diagnosed by X-ray or blood analysis, examination of synovial fluid taken from affected joints, and, diagnosed according to the American Rheumatism Association criteria, as is known in the art.

Rheumatoid arthritis (RA) is a chronic syndrome characterized by nonspecific, usually symmetric inflammation of the peripheral joints, potentially resulting in progressive destruction of articular and periarticular structures. Inflammation and hyperplasia of the synovium are hallmarks of rheumatoid arthritis. The normal synovium is a delicate tissue lining the joint capsule; however, in RA, the synovium transforms into an aggressive, tumor-like structure called the pannus. Synoviocytes (fibroblasts) and macrophages within the synovium orchestrate a self-perpetuating inflammatory response via the autocrine actions of cytokines (i.e. IL1 β, TNFα and IL6). Proliferating synoviocytes in the vicinity of the affected cartilage produce matrix-degrading molecules, including matrix metalloproteinases (MMPs) and express growth factors and adhesion molecules. Gradual destruction of articular cartilage is the most debilitating sign of the disease.

Osteoarthritis (OA) is the most common form of arthritis and is characterized by degenerative loss of articular cartilage, subchondral bony sclerosis, cartilage and bone proliferation at the joint margins with subsequent osteophyte formation and, commonly, secondary synovial inflammation. Osteoarthritis (OA) is a slowly progressive degeneration of the articular cartilage that manifests in the weight-bearing joints such as the knees and hips. Osteoarthritis, described as "wear and tear" arthritis, is characterized by narrowing of the joint owing to the loss of articular cartilage and thickening of the subchondral bone. At a later stage, inflammation of the synovium may occur which plays an important role in the pathologic process by accelerating the catabolism. All these events lead to nonfunctional and painful joint.

The modulation of locally produced corticotropin-releasing hormone (CRH) plays a role in both vascular changes and pathologic mechanisms associated with joint inflammation, a process that may be mediated through the NGFI-B family (Ann. N.Y. Acad Sci (2002) 966 119-30).

Accordingly, the present invention also provides a method of treating or preventing inflammatory immune disease in a subject by administering to the subject in need of such treatment any compound or composition of the present invention.

In one aspect the inflammatory disease includes arthritis, including without limitation rheumatoid arthritis (RA); psoriatic arthritis, infectious arthritis, juvenile rheumatoid arthritis; osteoarthritis, and spondyloarthropaties.

Cardiovascular disease is a serious problem and accounts for 44% of the mortality in the USA. Atherosclerotic cardiovascular disease is generalized process that involves the brain, heart and peripheral arteries. Atherosclerosis is characterized by intimal thickening caused by the accumulation of cells, infiltration of inflammatory cells, lipids, and connective tissues leading to the formation of atherosclerotic plaques.

Plaques can grow large enough to significantly reduce the blood's flow through an artery. However significant damage to the body can also occur when the artery walls become fragile and rupture. Atherosclerotic plaques that rupture can cause blood clots to form that can block blood flow or break off and travel to another part of the body. If either happens and the blood clot blocks a blood vessel that feeds the heart, it can cause a heart attack. If the blood clot blocks a blood vessel that feeds the brain, it can cause a stroke. And if blood supply to the arms or legs is reduced, it can cause difficulty walking and eventually gangrene.

Accordingly atherosclerosis encompasses a range of vascular diseases and conditions that arise as a result of the primary disease modality. Atherosclerotic cardiovascular diseases can be recognized and understood by physicians practicing in the relevant fields of medicine and include the following: Restenosis, coronary heart disease (also known as coronary artery heart disease or ischemic heart disease), cerebrovascular disease including ischemic stroke, multi-infarct dementia, and peripheral vessel disease, including erectile dysfunction.

Plaque formation is thought to occur via the invasion of the artery wall by inflammatory cells, such as macrophages, the recruitment and migration of smooth muscle cells and the intracellular accumulation of lipoproteins and lipids. Inflammatory cytokines induce an inflammatory response leading to inflammatory cell infiltration, production of matrix metalloproteinases further activating tissue destruction.

NGFI-B family members are expressed in smooth muscle cells that play a key role in intimal thickening in atherosclerosis and restenosis (Arterioscler. Thromb. Vasc. Biol. (2003) 23 (9) 153540). Experiments with knockout expressing dominant negative mutants of NGF-B β and γ demonstrate that these family members act to inhibit vascular plaque formation (Circulation (2002) 106 (12) 1530-5).

Accordingly a compound or composition of the present invention may be administered to prevent or reduce the risk of occurrence, or recurrence where the potential exists, of coronary heart disease event, a cerebrovascular event, and/or intermittent claudication.

Coronary heart disease events are intended to include coronary heart disease death, myocardial infarction and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease.

The term "atherosclerotic disease event" as used herein is intended to encompass coronary heart disease events, cerebrovascular events, and intermittent claudication. It is intended that person who have previously experienced one or more non-fatal atherosclerotic disease events are those for whom the potential for recurrence of such an event exists.

Osteoporosis is a term used to define increased bone porosity of the skeleton resulting from a reduction in bone mass. This disease affects the elderly, is particularly prevalent amongst females, and is sometimes a secondary response to other clinical conditions. Thus, osteoporosis may be primary or secondary, and depending on numerous parameters, can be localized to a certain bone region or limb, or may involve the entire skeleton. Osteoporosis normally refers to the common primary forms such as senile and postmenopausal osteoporosis, whereas secondary forms include endocrine disorders (hyperparathyroidism, hyperthyroidism, hypothyroidism, acromegaly, Cushing's syndrome, prolactinaoma, Type I diabetes), neoplasia (multiple myeloma, sarcinomatosis, mast cell disease, thyroid/parathyroid ademo), gastrointestinal disorders (malnutrition, malabsorption, hepatic insufficiency), osteoarthritis and rheumatoid arthritis, drugs (anticoagulants, chemotherapeutics, corticosteroids, lithium), and a number of other non-specific disorders (immobilization or inactivity, pulmonary disease, anemia). Regardless of the etiology, the critical loss of bone makes the skeleton vulnerable to fractures and pain. Over 15 million individuals suffer from primary osteoporosis in the United States and their direct medical costs are over $1 billion annually.

Postmenopausal osteoporosis is characterized by a hormonal dependent accelerated bone loss. Following menopause, the yearly loss of bone mass may reach 2% of the cortical bone and 9% of the cancellous bone. Estrogen is believed to play an important role in the reduction of bone loss. The estrogen effects are thought to be mediated by cytokines, which are found elevated in osteoporotic bone. It appears that decreased estrogen levels are capable of inducing cytokines such as IL-1, which are capable of stimulating bone resorption. IL-1 is the most potent stimulator of osteoclast recruitment and activity and thought to play an important role in bone resorption in post-menopausal osteoporosis.

A number of genes that are induced by IL-1 (cathepsin K, matrix metalloproteinases and COX-2) are elevated in osteoporotic bone and produced by osteoblasts and osteoclasts in vitro. Inhibition of osteoclast recruitment and activation are key steps in shifting the balance from resorption to bone formation, resulting in increased bone mass. Parathyroid hormone (PTH) induces NGFI-B expression in osteoblasts (Biochem. Biophys. Res. Comm. (2003) 306 (1) 14450) and accordingly the modulation NGFI-B family activity by compounds of the present invention provides a mechanism of regulating, preventing and or treating osteoporosis.

Accordingly in one aspect, the present compounds and compositions are intended to treat, or prevent the occurrence of all diseases classified as osteoporosis, particularly post-menopausal osteoporosis, senile osteoporosis, idiopathic osteoporosis, immobilization osteoporosis, post-partum osteoporosis, juvenile osteoporosis, and osteoporosis secondary to gonadal insufficiency, malnutrition, hyperprolactinemia, prolactinoma, disorders of the gastrointestinal tract, liver, or kidneys, and osteoporosis that is a sequella of prior osteomalacia, chronic acidosis, thyrotoxicosis, hyperparathyroidism, glucocorticoid excess or chronic disorders involving the bone marrow, and heritable forms of osteoporosis such as osteogenesis imperfecta and its variants, and other heritable disorders of connective tissue.

Combination Therapy

Combination therapy includes administration of a single pharmaceutical dosage formulation which contains a compound of the present invention and one or more additional active agents, as well as administration of a compound of the present invention and each active agent in its own separate pharmaceutical dosage formulation. For example, a NGFI-B family receptor agonist, partial agonist, partial antagonist, or antagonist of the present invention and an additional active compound. These compounds and pharmaceutical compositions can be administered to the patient together in a single oral dosage composition such as a tablet or capsule, or each agent administered in separate oral dosage formulations. Where separate dosage formulations are used, the compounds described herein and one or more additional active agents can be administered at essentially the same time, i.e., concurrently, or at separately staggered times, i.e., sequentially; combination therapy is understood to include all these regimens.

For treatment Parkinson's disease in accordance with the present invention, a compound or composition of the present invention is suitably administered alone as an active ingredient in a pharmaceutical composition, or is co-administered with at least one compound selected from levodopa (L-DOPA or L-dihydroxyphenylalanine), L-aromatic amino acid decarboxylase (AADC) inhibitors and/or catechol O-methyl transferase (COMT) inhibitors.

For treatment for inflammatory immune diseases in accordance with the present invention, a compound or composition of the present invention is suitably administered alone as an active ingredient in a pharmaceutical composition, or is co-administered with at least one anti-inflammatory compound selected from a matrix metalloproteinase inhibitor, an inhibitor of pro-inflammatory cytokines (e.g., anti-TNF molecules, TNF soluble receptors, and IL1, non-steroidal anti-inflammatory drugs (NSAIDs) such as prostaglandin synthase inhibitors (e.g., choline magnesium salicylate, salicylsalicyclic acid), COX-1 or COX-2 inhibitors, or corticosteroids, such as methylprednisone, prednisone, or cortisone.

In certain embodiments a composition of the present invention and the anti-inflammatory compound are part of a single therapeutic composition (e.g. such that the administration may be accomplished with a single composition). In other embodiments, a composition of the present invention and the anti-inflammatory compound are separate compositions (e.g. such that each composition may be administered separately to the subject). In preferred embodiments, a compound or composition of the present invention and the anti-inflammatory compound are administered to the subject at about the same time (e.g., within a few seconds, minutes, or hours of each other). In certain embodiments it may also be advantageous to administer the active compound together with an analgesic or other pain killer medication such as acetaminophen or ibuprofen.

For treatment for Arthritis in accordance with the present invention, a compound or composition of the present invention is suitably administered alone as an active ingredient in a pharmaceutical composition, or is co-administered with at least one anti-arthritic compound selected from a matrix metalloproteinase inhibitor, an inhibitor of pro-inflammatory cytokines (e.g., anti-TNF molecules, TNF soluble receptors, and IL1 beta, non-steroidal anti-inflammatory drugs (NSAIDs) such as prostaglandin synthase inhibitors (e.g., choline magnesium salicylate, salicylsalicyclic acid), or corticosteroids, such as methylprednisone, prednisone, or cortisone. In certain embodiments it may also be advantageous to administer the active compound together with an analgesic or other pain killer medication such as acetaminophen or ibuprofen.

An example of combination therapy that modulates, or prevents the onset of the symptoms, or associated complications of atherosclerosis, comprises the administration of one or more of the compounds of the present invention in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; LXR α or β agonists, antagonists, or partial agonists, FXR agonists, antagonists, or partial agonists, an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin.

The present invention also comprises a combination therapy for the administration, to a human afflicted with osteoporosis, comprising a combination of a parathyroid hormone (PTH) or physiologically active fragment thereof, (hPTHF 1-34) for example with any of the compounds or compositions claimed herein.

In another embodiment the combination therapy further comprises a dietary calcium supplement and any of the compounds or compositions claimed herein. The invention also comprises pharmaceutical compositions intended for use in this method.

In certain embodiments a compound or composition of the present invention and the parathyroid hormone or calcium supplement are part of a single therapeutic composition (e.g. such that the administration may be accomplished with a single composition). In other embodiments, a compound or composition of the present invention and the parathyroid hormone or calcium supplement are separate compositions (e.g. such that each composition may be administered separately to the subject). In preferred embodiments, a composition of the present invention and the parathyroid hormone or calcium supplement are administered to the subject at about the same time (e.g., within a few seconds, minutes, or hours of each other).

Ranges of administration of parathyroid hormone hPTHF 1-34, may be used, for example, 100-700 units/day, more preferably 200-600 units/day, and most preferably 400-500 units/day, wherein "units" are defined in terms of the International Reference Preparation of hPTHF 1-34 and comparative bioassays in one of the established PTH bioassays. Potency ratios of different PTH analogues differ in different assays. The "units" are expressed in the chick hypercalcemic assay.

For other PTHF molecules, the ranges of administration are those high enough to stimulate bone remodeling in humans, yet not so high as to produce net bone resorption nor enough bone mineral mobilization to produce hypercalcemia or hypercalciuria. For compounds other than hPTH 1-34, dosage can be quantitated on a weight basis, or in terms of an appropriately established reference standard.

By "dietary calcium supplement" as used in this invention is meant supplementing the normal diet with calcium at a level greater than that level which is recommended as the daily dietary allowance. Accordingly, a dietary calcium supplement for an adult would involve the administration of sufficient calcium to increase the total oral intake of diet plus supplement to 38-50 millimoles/day. When a dietary calcium supplement is used, the calcium is administered in a non-toxic form. The dosage rates mentioned herein refer to the amounts of calcium present, and the dosage rate of the actual compound used can be easily calculated therefrom using the formula weight of the compound being administered. Milk or any non-toxic salt of calcium may be utilized provided that the counter ion is not toxic to the human in which it is being administered. Typical suitable non-toxic counter ions include carbonate, citrate, phosphate, gluconate, lactate, chloride, and glycerol phosphate. The upper limit of the dietary calcium supplement is determined by the toxic effects of calcium, which varies slightly from patient to patient, as is well understood by those skilled in the art. Typically, in humans, the maximum allowance per day is 2000 mg calcium per day.

EXAMPLES

Example 1

Analysis of compound activity via a Gal-4-chimera—reporter gene screening assay. Compound activity was determined using a co-transfection assay with Nurr1-LBD-GAL4 co-transfected with the ligand binding domain (LBD) of RXRα into CV-1 cells.
Molecular Biology pCMX-GAL4-Nurr1-LBD receptor chimera was constructed by cloning nucleotides encoding amino acids 353-598 of mouse Nurr1 protein into the Asp718/BamH1 sites of pCMX-GAL4 (Umesono et al. Cell (1991) 65 (7) 1255-66). pCMX-RXR alpha-LBD was constructed by cloning nucleotides including amino acids 222-462 of the human RXR alpha into the vector pCMX (Perlmann et al. (1993) Genes & Development 7 1411-1422).

Gal-4-tk-Luc ($GAL4_{UAS}$-Tk-Luciferase) reporter constructs were constructed by insertion of four copies of the Gal4 UAS (Kang et al. (1993) J. Biol. Chem. 268 9629-9635) into the Hind III site of tk-Luc. The parental plasmid tk-Luc was prepared by insertion of the Herpes simplex virus thymidine kinase gene promoter (−105 to +51) obtained from the plasmid pBLCAT2 by digestion with HindIII and XhoI (described in Luckow et al (1987) Nuc. Acid. Res. 15 5490) into the plasmid MTV-LUC described by Hollenberg and Evans (Cell (1988) 55 899-906) after removal of MTV-LTR promoter sequence from MTV-LUC via digestion with HindIII and XhoI. Correct cloning was confirmed by restriction digestion and/or sequencing.

Assay Procedure

Assays were performed using CV-1 (African Green Monkey Kidney Cells) (ATTC) cells at 70 percent confluency in T175 flasks transiently transfected with the expression plasmids.

Assays were performed using CV-1 (African Green Monkey Kidney Cells) (ATTC) cells at 70 percent confluency in T175 flasks grown with media containing 10% charcoal/Dextran-treated fetal bovine serum. Cells were transiently transfected with a DNA mixture containing (3 μg pCMX-GAL4-Nurr1-LBD, 2 μg pCMX-RXR-LBD, 30 μg of pCMX-GAL4$_{UAS}$-Tk-Luciferase, 5.5 μg of pCMX-beta-galactosidase), using the transfection reagent FuGENE6 (Roche Molecular Biochemicals, Indianapolis, Ind.) following recommended protocols and instructions provided by the manufacturer. Following incubation with transfection reagents for 5 hours at 37° C., cells were washed, removed from the flasks with 1× Trypsin-EDTA solution (Sigma-Aldrich, Inc. St. Louis, Mo., and then resuspended in media containing 5% charcoal/Dextran-treated fetal bovine serum to give a final concentration of $1.1 \times 10^5$ cells/ml.

Assay plates were prepared by dispensing approximately 5 μl of each compound into a well of a 384 well plate to achieve a final compound concentration of approximately 10 μM after addition of cells. Cells were added to assay plates (45 μl via the use of a MultiDrop dispenser (MTX Labs, Inc., Vienna, Va.). The assay plates containing both compounds and screening cells were incubated for approximately 20 hours at 37° C. in a tissue culture incubator.

After incubation of the transfected cells with compounds, Lysis buffer (1% Triton X-100, 10% Glycerol, 5 mM DTT, 1 mM EGTA, 25 mM Tricine) and Luciferin assay buffer (0.73 mM ATP, 22.3 mM Tricine, 0.11 mM EDTA, 33.3 mM DTT, 0.2M MgSO$_4$, 11 mM Luciferin, 6.1 mM Coenzyme A, 0.01 mM HEPES) were prepared. Media was removed from the plates and lysis buffer and luciferin assay buffer mixed in a 1:1 ratio and then 30 μl was added to each well (384-well plate). Plates were read on the Northstar (Northstar Technologies, Inc., Acton, Mass.) and data was analyzed using ActivityBase (ID Business Solutions, Ltd., Guildford, Surrey, UK). Luciferase values were normalized with β-galactosidase values using the pCMX-GAL4 expression vector, to normalize for transfection efficiency as described previously (Willey et al., Gene & Development, (1995) 9:1033-1045).

Results for representative members of the tested compounds are shown in FIG. 1.

Example 2

Specificity assays were conducted with Gal4 chimera—reporter gene assays with the ligand binding domain of the nuclear receptor of interest fused to—GAL4 co-transfected with the ligand binding domain of RXRα.

Molecular Biology pCMX-GAL4-FXR-LBD receptor chimera was constructed by cloning nucleotides encoding amino acids 248-476 of human FXR protein into pCMX-GAL4 (Umesono et al. Cell (1991) 65 (7) 1255-66).

pCMX-GAL4PPARγ receptor chimera: Nucleotides encoding amino acids 174 to 475 of human PPARγ was PCR amplified and cloned to pCMX-GAL4 (Umesono et al. Cell (1991) 65 (7) 1255-66).

pCMX-GAL4-PPARα receptor chimera: Nucleotides encoding amino acids 168 to 468 of human PPARα was PCR amplified and cloned to pCMX-GAL4 (Umesono et al. Cell (1991) 65 (7) 1255-66).

pCMX-GAL4 PPARδ-LBD receptor chimera was constructed by PCR cloning of nucleotides encoding amino acids 179-442 of human PPARδ into pCMX-GAL4 (Umesono et al. Cell (1991) 65 (7) 1255-66). The amplified gene contains a silent mutation at 1119 bp from C to A which does not result in an amino acid change.

pCMX-GAL4LXRα receptor chimera: Nucleotides encoding amino acids 164-447 of human LXRα was PCR amplified and cloned to pCMX-GAL4 (Umesono et al. Cell (1991) 65 (7) 1255-66).

pCMX-GAL4-LXRβ receptor chimera: Nucleotides encoding amino acids 155-461 of human LXRb was PCR amplified and cloned into pCMX-GAL4 (Umesono et al. Cell (1991) 65 (7) 1255-66).

pCMX-GAL4-SXR: A fragment encoding amino acids 107-434 of human SXR was cloned into pCMX-GAL4 (Umesono et al. Cell (1991) 65 (7) 1255-66).

pCMX-GAL4-RXRa LBD: Nucleotides encoding amino acids 203 to 462 of human RXRa were PCR amplified and cloned into pCMX-GAL4 (Forman et. Al. (1995) Cell 81 541-550).

pCMX-GAL4-NGFI-Bγ LBD: Nucleotides encoding amino acids 348-597 of NGFI-Bγ (Perlmann and Jansson (1995) Genes & Dev 9 769-782) were PCR amplified and cloned into pCMX-GAL4 (Forman et. Al. (1995) Cell 81 541-550).

pCMX-GAL4-Nor-1 LBD: Nucleotides encoding amino acids 350-625 of Nor-1 (Zetterstrom et. Al. (1996) Mol Endo 10 1656-1666) were PCR amplified and cloned into pCMX-GAL4 (Forman et. Al. (1995) Cell 81 541-550).

pCMX-GAL4-RARa LBD: Nucleotides encoding amino adds 156-462 of human RARα (Forman et. Al. (1995) Cell 81 541-550) were PCR amplified and cloned into pCMX-GAL4 (Forman et. Al. (1995) Cell 81 541-550).

pCMX-GAL4-RARβ receptor chimera: Nucleotides encoding amino acids 147 to 448 of human RARβ was PCR amplified and cloned into pCMX-GAL4 (Umesono et al. Cell (1991) 65 (7) 1255-66).

pCMX-GAL4-RARγ receptor chimera: Nucleotides encoding amino acids 198 to 496 of human RARγ was PCR amplified and cloned into pCMX-GAL4 (Umesono et al. Cell (1991) 65 (7) 1255-66).

pCMX-GAL4-VDR receptor chimera: Nucleotides encoding amino acids 92-427 of human VDR was cloned into pCMX-GAL4 (Umesono et al. Cell (1991) 65 (7) 1255-66).

Correct cloning was confirmed in each case by restriction digestion and/or sequencing.

Assay Procedure

Assays were performed using CV-1 (African Green Monkey Kidney Cells) (ATTC) cells at 70 percent confluency in TI 75 flasks transiently transfected with the expression plasmids (3 μg pCMX-GAL4-LBD of the nuclear receptor of interest, 2 μg pCMX-RXR-LBD, 30 μg of pCMX-GAL4$_{UAS}$-Tk-Luciferase, 5.5 μg of pCMX-beta-galactosidase), using the transfection reagent FuGENE6 (Roche Molecular Biochemicals, Indianapolis, Ind.) following recommended protocols and instructions provided by the manufacturer. Following incubation with transfection reagents for 5 hours at 37° C., cells were washed, removed from the flasks with 1× Trypsin- EDTA solution (Sigma-Aldrich, Inc. St. Louis, Mo., and then resuspended in media containing 5% charcoal/Dextran-treated fetal bovine serum to give a final concentration of $1.1 \times 10^5$ cells/ml.

Assay plates were prepared by dispensing approximately 5 µl of each compound into a well of a 384 well plate to achieve a final compound concentration of approximately 10 µM after addition of cells. Cells were added to assay plates (45 µl) via the use of a MultiDrop dispenser (MTX Labs, Inc., Vienna, Va.). The assay plates containing both compounds and screening cells were incubated for approximately 20 hours at 37° C. in a tissue culture incubator.

After incubation of the transfected cells with compounds, Lysis buffer (1% Triton X-100, 10% Glycerol, 5 mM DTT, 1 mM EGTA, 25 mM Tricine) and Luciferin assay buffer (0.73 mM ATP, 22.3 mM Tricine, 0.11 mM EDTA, 33.3 mM DTT, 0.2M MgSO4, 11 mM Luciferin, 6.1 mM Coenzyme A, 0.01 mM HEPES) were prepared. Media was removed from the plates and lysis buffer and luciferin assay buffer mixed in a 1:1 ratio and then 30 µl was added to each well (384-well plate). Plates were read on the Northstar (Northstar Technologies, Inc., Acton, Mass.) and data was analyzed using ActivityBase (ID Business Solutions, Ltd., Guildford, Surrey, UK). Luciferase values were normalized with β-galactosidase values using the pCMX-GAL4 expression vector, to normalize for transfection efficiency as described previously (Willey et al., Gene & Development, (1995) 9:1033-1045).

Figure 2:
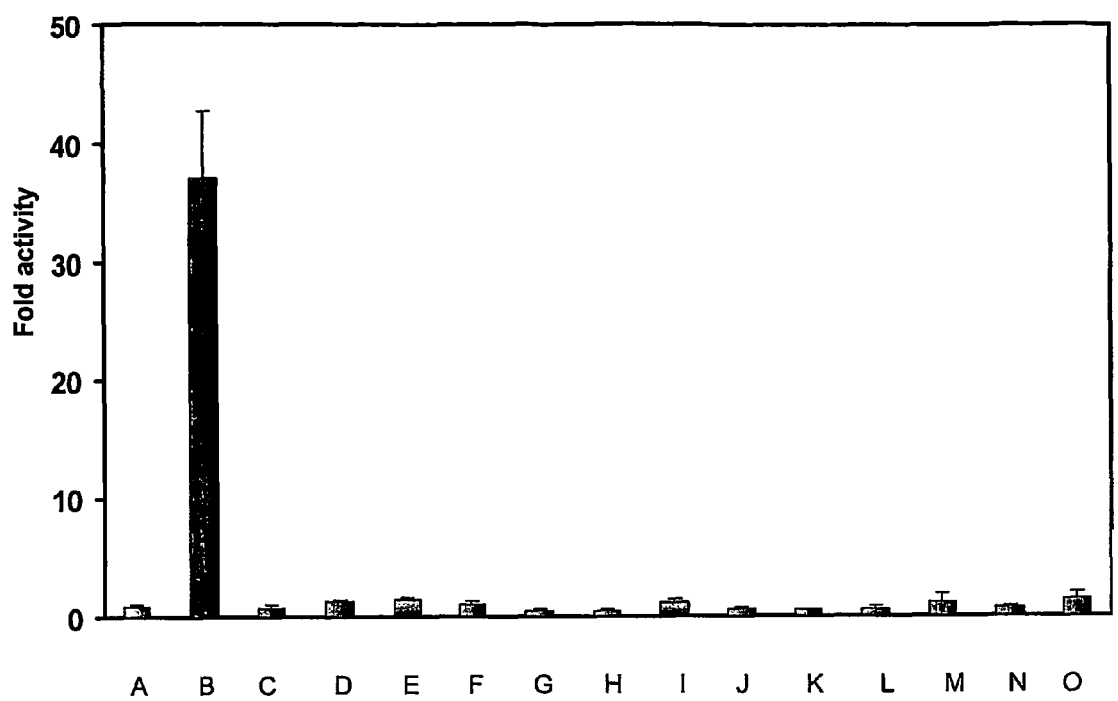
FIG. 2 Provides the results of a selectivity profile of certain compounds of the present invention with respect to the activation of different nuclear receptors, in the presence of RXR, in a Gal4 chimera/reporter gene assay.
Figure 3:
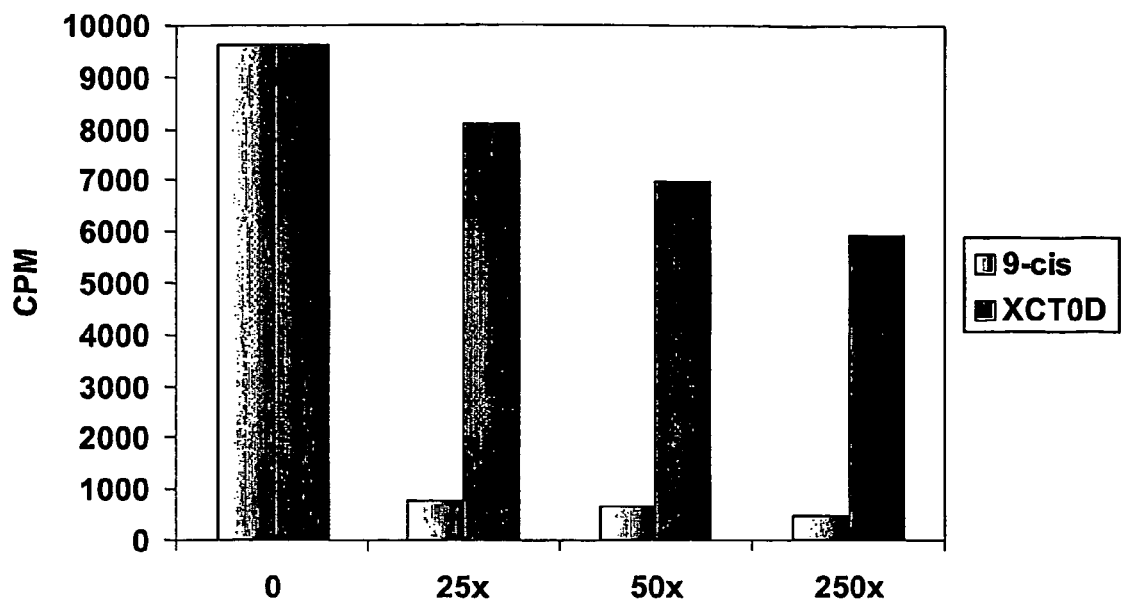
FIG. 3 Shows that certain compounds of the present invention bind poorly to RXR and are relatively inefficient in displacing radiolabelled 9-cis retinoic acid from RXR.

The results shown in FIG. 2 and FIG. 3 show a representative selectivity profile selective with respect to the disclosed nuclear receptor ligand binding domains.

Example 3

Selected compounds were analyzed to determine their ability to directly interact with RXR in a scintillation proximity assay (SPA) which measures the compounds ability to displace radioactively labeled retinoic acid.

Molecular Biology

A Baculovirus expression plasmid for human RXRα were made by cloning the appropriate full-length cDNA (GenBank Accession No. NM_002957) into the pBacPakhis1 vector (Clontech, CA) following standard procedures. Insertion of the cDNA into the pBAcPakhis1 vector polylinker created an in frame fusion of the cDNA to an N-terminal poly-His tag present in pBacPakhis1. Correct cloning was confirmed by restriction mapping, and/or sequencing.

Assay Procedure

Cell lysates were prepared by infecting healthy, Sf9 insect cells at a density of approximately $1.25 \times 10^6$/ml at 27° C., in a total volume of 500 ml per 1 L sized spinner flasks, cultured under standard conditions. To prepare RXRα lysate, insect cells were transfected with the RXR α expression cassette at an M.O.I-1.0. After incubation for 48 hours cells were harvested by centrifugation and pelleted. Cell pellets were resuspended in two volumes of ice-cold freshly prepared extraction buffer (20 mM Tris pH 8.0, 10 mM Imidazole, 400 mM NaCl, containing one EDTA free protease inhibitor tablet (Roche Catalog No: 1836170) per 10 ml of extraction buffer).

Cells were homogenized slowly on ice using a Douncer to achieve 80-90% cell lysis. The homogenate was centrifuged in a pre-chilled rotor (Ti50 or Ti70, or equivalent) at 45,000 rpm for 30 minutes at 4° C. Aliquots of the supernatant were frozen on dry ice and stored frozen at −80° C. until quantification and quality control. Aliquots of the lysates were tested in the SPA assay to ensure lot to lot consistency, and via SDS-PAGE analysis after purification using Ni-NTA Resin (Qiagen) to normalize for protein concentration and expression level prior to use in screening assays.

Assays were performed using 96-well, non-binding surface plates(Corning) in a total volume of 50 µl by adding the following components per well in the order given;
(1) 12.5 µl of 2× SPA buffer with EDTA (40 mM $K_2HPO_4$/$KH_2PO_4$ pH7.3, 100 mM NaCl, 0.05% Tween 20, 20% Glycerol, 4 mM EDTA).
(2) 0.5 µl of distilled $H_2O$
(3) 1 µL of XCT compound or 1 µL of 40% DMSO (dilute 40% DMSO)
(4) 1 µL of $^3$H]-9-cis-Retinoic acid (RA; Amersham): 43Ci/nmol, 50 µCi/250 µl (25 nM final concentration in EtOH)
(5) 10 µl RXRα lysate (5 µl RXRα lysate+5 µl 1×His binding buffer, (20 mM Tris-HCl pH 7.9, 500 mM NaCl, 5 mM Imidazole)).
(6) 25 µl of His-tag SPA beads (12.5 µl beads+12.5 µl 2×SPA buffer w/o EDTA, (40 mM $K_2HPO_4$/$KH_2PO_4$ pH 7.3, 100 mM NaCl, 0.05% Tween 20, 20% Glycerol)

Plates were incubated at room temperature for 45 minutes and read on Microbeta liquid scintillation counter (Perkin Elmer) with the following settings: Counting Mode: DPM; Sample Type: SPA; ParaLux Mode: low background; Count time: 30 sec.

Figure 4A:
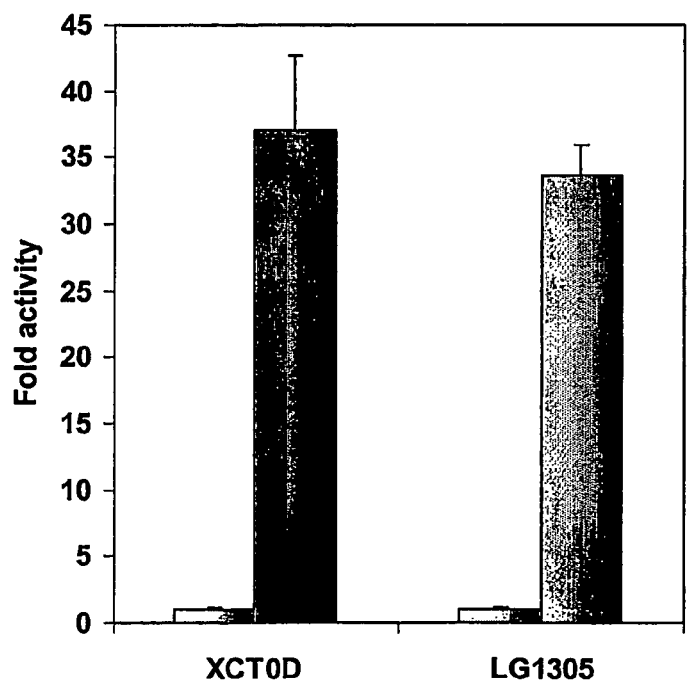
FIGS. 4A and 4B Show that certain compounds of the present invention are able to selectively activate Nurr1/RXR heterodimers but have minimal ability to directly activate RXR.
Figure 4B:
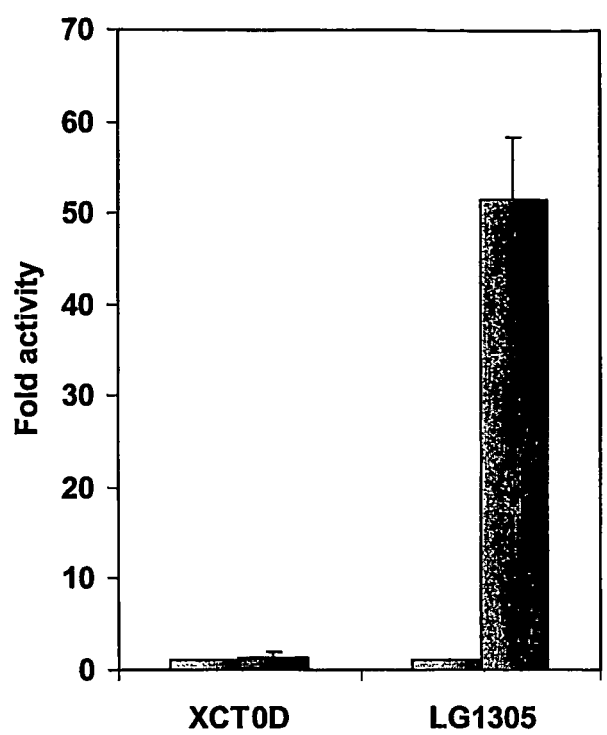

Representative results, are shown in FIG. 4 for a compound of the present invention.

What is claimed is:

1. A pharmaceutical composition comprising a compound of formula (I)

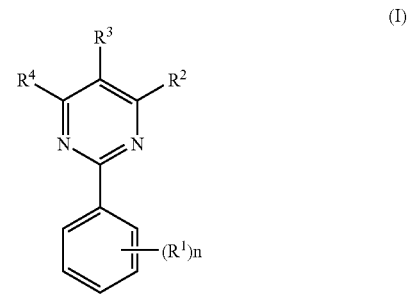

or a pharmaceutical acceptable salt thereof, wherein
n is 0 to 5;
$R^1$ is each independently selected from the group consisting of halo, cyanato, thiocyanato, selenocyanato, trifluoromethoxy, azido, cyano, nitro, hydroxyl, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;
$R^2$ is selected from the group consisting of optionally substituted cycloalkyl, optionally substituted aralkyl, —$OR^6$, —$S(O)R^6$, —$S(O)_2R^6$, —$N(R^9)S(O)_zR^{10}$, —$C(O)R^6$, —$C(O)OR^6$, and —$C(O)N(R^7)R^8$;
$R^3$ is independently selected from the group consisting of hydrogen, halo, cyanato, thiocyanato, selenocyanato, trifluoromethoxy, azido, nitro, hydroxyl, mercapto, alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl; and R⁴ selected from the group consisting of cyanato, thiocyanato, selenocyanato, trifluoromethoxy, azido, cyano, nitro, hydroxyl, formyl, mercapto, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl, optionally substituted heterocyclylalkyl, —R¹²—N(R¹⁴)R¹⁵, —R¹²—C(O)R¹³, —R¹²—C(O)OR¹⁵, —R¹²—N(R¹⁴)C(O)R¹⁵, —R¹²—N(R¹⁴)C(O)OR¹⁵, —R¹²—S(O)ᵣR¹⁵ and —R¹²—S(O)ᵣN(R¹⁴)R¹⁵;

R⁶ represents substituted alkyl, optionally substituted aryl, optionally substituted aralkyl or optionally substituted heterocyclyl;

R⁷ represents H or optionally substituted alkyl;

R⁸ represents optionally substituted alkyl, optionally substituted aryl, optionally substituted aralkyl or optionally substituted heterocyclyl;

R⁹ represents H or optionally substituted alkyl;

R¹⁰ represents optionally substituted alkyl, optionally substituted aryl, optionally substituted aralkyl or optionally substituted heterocyclyl;

R¹² represents a $C_1$-$C_6$ alkylene, $C_2$-$C_6$ alkenylene, $C_2$-$C_6$ alkynylene or $C_1$-$C_6$ alkyleneoxy;

R¹³ represents optionally substituted alkyl, optionally substituted aryl, optionally substituted aralkyl or optionally substituted heterocyclyl;

R¹⁴ represents H or optionally substituted alkyl;

R¹⁵ represents optionally substituted alkyl, optionally substituted aryl, optionally substituted aralkyl or optionally substituted heterocyclyl, and where each t is independently 0 to 2, wherein the optional substituents are independently Q¹, where Q¹ represents alkyl, haloalkyl, cycloalkyl, cycloalkylalkyl, heterocyclylalkyl, aryl, aralkyl, heteroaryl, heteroaralkyl, cyano, halo, hydroxyl, hydroxycarbonyl, cyanato, thiocyanato, selenocyanato trifluoromethox azido, —R³⁰—OR³¹, —R³⁰—SR¹⁶, —R³⁰—N(R³²)(R³³), —R³⁰—C(J)R³⁴, —R³⁰—C(J)OR³¹, —R³⁰—C(J)N(R³¹)N(R³²)(R³³), —R³⁰—N(R³¹)C(J)R³⁴, —R³⁰—N(R³¹)C(J)OR³¹, —R³⁰—N(R³¹)C(J)N(R³²)(R³³), —R³⁰—OC(J)R³⁴, —R³⁰—OC(J)OR³¹, —R³⁰—OC(J)N(R³²)(R³³), —Si(R³⁵)₃, —N(R³¹)S(O)ᵧR³⁶ or —R³⁰—S(O)ᵧR³⁶;

where each R³⁰ is independently a direct bond or a straight or branched alkylene chain;

R³¹ and R³⁴ are each independently hydrogen, alkyl, alkenyl, alkynyl, haloalkyl, cycloalkyl, cycloalkylalkyl, heterocyclylalkyl, aryl, aralkyl, heteroaryl or heteroaralkyl;

R³² and R³³ are each independently hydrogen, alkyl, alkenyl, alkynyl, haloalkyl, cycloalkyl, cycloalkylalkyl, heterocyclyl, aryl, aralkyl, heteroaryl or heteroaralkyl;

or R³² and R³³ together with the nitrogen atom to which they are attached, form a heterocyclylalkenyl, or heteroaryl;

R³⁵ R³⁶ and R¹⁶ are each independently alkyl, alkenyl, alkynyl, haloalkyl, cycloalkyl, cycloalkylalkyl, heterocyclyl, heterocyclylalkyl, aryl, aralkyl, heteroaryl or heteroaralkyl;

each J is independently O or S; and each y is independently 0 to 2;

and a pharmaceutically acceptable excipient.

2. A pharmaceutical composition comprising the compound of formula (II)

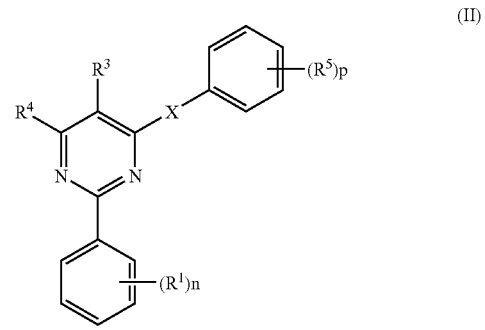

wherein n is 0 to 2; p is 0 to 2;

X is O, or S(O)ᵣ where r is 0 to 2;

R¹ is each independently selected from the group consisting of halo, cyanato, thiocyanato, selenocyanato, trifluoromethoxy, azido, cyano, nitro, hydroxyl, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

R³ is independently selected from the group consisting of hydrogen, halo, cyanato, thiocyanato, selenocyanato, trifluoromethoxy, azido, nitro, hydroxyl, formyl, mercapto, alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

R⁴ selected from the group consisting of cyanato, thiocyanato, selenocyanato, trifluoromethoxy, azido, cyano, nitro, hydroxyl, formyl, mercapto, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl, optionally substituted heterocyclylalkyl, —R¹²—OR¹³, —R¹²—N(R¹⁴)R¹⁵, —R¹²—C(O)R¹³, —R¹²—C(O)OR¹⁵, —R¹²—N(R¹⁴)C(O)R¹⁵, —R¹²—N(R¹⁴)C(O)OR¹⁵, —R¹²—S(O)ᵣR¹⁵ and —R¹²—S(O)ᵣN(R¹⁴)R¹⁵; and each R⁵ independently selected from the group consisting of halo, cyanato, thiocyanato, selenocyanato, trifluoromethoxy, azido, cyano, hydroxyl, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, —OR²⁰, —S(O)ᵣR²⁰, —N(R⁷)R²⁰, —N(R⁹)S(O)ᵣR²⁰, —C(O)R²⁰, and —C(O)OR²⁰;

R⁷ and R⁹ are each independently H or optionally substituted alkyl;

R¹² represents a $C_1$-$C_6$ alkylene, $C_2$-$C_6$ alkenylene, $C_2$-$C_6$ alkynylene or $C_1$-$C_6$ alkyleneoxy;

R¹³ represents optionally substituted alkyl, optionally substituted aryl, optionally substituted aralkyl or optionally substituted heterocyclyl;

R¹⁴ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl and where each t is independently 0 to 2 wherein the optional substituents are independently $Q^1$, where $Q^1$ represents alkyl, haloalkyl, cycloalkyl, cycloalkylalkyl, heterocyclyl, heterocyclylalkyl, aryl, aralkyl, heteroaryl, heteroaralkyl, cyano, halo, hydroxyl, hydroxycarbonyl, cyanato, thiocyanato, selenocyanato, trifluoromethoxy, azido, $-R^{30}-OR^{31}$, $-R^{30}-SR^{16}$, $-R^{30}-N(R^{32})(R^{33})$, $-R^{30}-C(J)R^{34}$, $-R^{30}-C(J)OR^{31}$, $-R^{30}-C(J)N(R^{31})N(R^{32})(R^{33})$, $-R^{30}-N(R^{31})C(J)R^{34}$, $-R^{30}-N(R^{31})C(J)OR^{31}$, $-R^{30}-N(R^{31})C(J)N(R^{32})(R^{33})$, $-R^{30}-OC(J)R^{34}$, $-R^{30}-OC(J)OR^{31}$, $-R^{30}-OC(J)N(R^{32})(R^{33})$, $-Si(R^{35})_3$, $-N(R^{31})S(O)_y R^{36}$ or $-R^{30}-S(O)_y R^{36}$;

where each $R^{30}$ is independently a direct bond or a straight or branched alkylene chain;

$R^{31}$ and $R^{34}$ are each independently hydrogen, alkyl, alkenyl, alkynyl, haloalkyl, cycloalkyl, cycloalkylalkyl, heterocyclyl, heterocyclylalkyl, aryl, aralkyl, heteroaryl or heteroaralkyl;

$R^{32}$ and $R^{33}$ are each independently hydrogen, alkyl, alkenyl, alkynyl, haloalkyl, cycloalkyl, cycloalkylalkyl, heterocyclyl, aryl, aralkyl, heteroaryl or heteroaralkyl;

or $R^{32}$ and $R^{33}$ together with the nitrogen atom to which they are attached, form a heterocyclylalkenyl, or heteroaryl;

$R^{35}$ $R^{36}$ and $R^{16}$ are each independently alkyl, alkenyl, alkynyl, haloalkyl, cycloalkyl, cycloalkylalkyl, heterocyclyl, heterocyclylalkyl, aryl, aralkyl, heteroaryl or heteroaralkyl;

each J is independently O or S; and each y is independently 0 to 2;

and a pharmaceutically acceptable excipient.

3. The pharmaceutical composition of claim 2 wherein n is 0; p is 0 to 2; X is O, or $S(O)_r$ where r is 0 to 2;

$R^3$ is independently selected from the group consisting of hydrogen, halo, cyanato, thiocyanato, selenocyanato, trifluoromethoxy, azido, nitro, hydroxyl, formyl, mercapto, alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^4$ selected from the group consisting of cyanato, thiocyanato, selenocyanato, trifluoromethoxy, azido, cyano, nitro, hydroxyl, formyl, mercapto, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl, optionally substituted heterocyclylalkyl, $-R^{12}-OR^{13}$, $-R^{12}-N(R^{14})R^{15}$, $-R^{12}-C(O)R^{13}$, $-R^{12}-C(O)OR^{15}$, $-R^{12}-N(R^{14})C(O)R^{15}$, $-R^{12}-N(R^{14})C(O)OR^{15}$, $-R^{12}-S(O)_r R^{15}$ and $-R^{12}-S(O)_r N(R^{14})R^{15}$;

each $R^5$ independently selected from the group consisting of halo, cyanato, thiocyanato, selenocyanato, trifluoromethoxy, azido, cyano, hydroxyl, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, $-OR^{20}$, $-S(O)_r R^{20}$, $-N(R^7)R^{20}$, $-N(R^9)S(O)_r R^{20}$, $-C(O)R^{20}$, and $-C(O)OR^{20}$;

$R^7$ and $R^9$ are each independently H or optionally substituted alkyl;

$R^{12}$ represents a $C_1$-$C_6$ alkylene, $C_2$-$C_6$ alkenylene, $C_2$-$C_6$ alkynylene or $C_1$-$C_6$ alkyleneoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl; and $R^{20}$ represents optionally substituted alkyl, optionally substituted aryl, optionally substituted aralkyl or optionally substituted heterocyclyl, and where each t is independently 0 to 2.

4. The pharmaceutical composition of claim 2 wherein n is 0 to 2; p is 0 to 2; X is O, or $S(O)_r$, where r is 0 to 2;

$R^1$ is each independently selected from the group consisting of halo, cyanato, thiocyanato, selenocyanato, trifluoromethoxy, azido, cyano, nitro, hydroxyl, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^3$ is independently selected from the group consisting of hydrogen, halo, cyanato, thiocyanato, selenocyanato, trifluoromethoxy, azido, nitro, hydroxyl, formyl, mercapto, lower alkyl, optionally substituted lower alkenyl, optionally substituted lower alkynyl, lower alkoxy, and lower aminoalkyl;

$R^4$ selected from the group consisting of cyanato, thiocyanato, selenocyanato, trifluoromethoxy, azido, cyano, nitro, hydroxyl, formyl, mercapto, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl, optionally substituted heterocyclylalkyl, $-R^{12}-OR^{13}$, $-R^{12}-N(R^{14})R^{15}$, $-R^{12}-C(O)R^{13}$, $-R^{12}-C(O)OR^{15}$, $-R^{12}-N(R^{14})C(O)R^{15}$, $-R^{12}-N(R^{14})C(O)OR^{15}$, $-R^{12}-S(O)_r R^{15}$ and $-R^{12}-S(O)_r N(R^{14})R^{15}$;

each $R^5$ independently selected from the group consisting of halo, cyanato, thiocyanato, selenocyanato, trifluoromethoxy, azido, cyano, hydroxyl, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, $-OR^{20}$, $-S(O)_r R^{20}$, $-N(R^7)R^{20}$, $-N(R^9)S(O)_r R^{20}$, $-C(O)R^{20}$, and $-C(O)OR^{20}$;

$R^7$ represents H or optionally substituted alkyl;

each $R^9$ is independently H or optionally substituted alkyl;

$R^{12}$ represents a $C_1$-$C_6$ alkylene, $C_2$-$C_6$ alkenylene, $C_2$-$C_6$ alkynylene or $C_1$-$C_6$ alkyleneoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ is represents optionally substituted alkyl, optionally substituted aryl, optionally substituted aralkyl or optionally substituted heterocyclyl, and where each t is independently 0 to 2.

5. The pharmaceutical composition of claim 2 wherein n is 0 to 2; p is 0 to 2; X is O, or $S(O)_r$ where r is 0 to 2;

$R^1$ is each independently selected from the group consisting of halo, cyanato, thiocyanato, selenocyanato, trifluoromethoxy, azido, cyano, nitro, hydroxyl, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^3$ is independently selected from the group consisting of hydrogen, halo, cyanato, thiocyanato, selenocyanato, trifluoromethoxy, azido, nitro, hydroxyl, formyl, mercapto, alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl; and $R^4$ selected from the group consisting of cyanato, thiocyanato, selenocyanato, trifluoromethoxy, azido, cyano, nitro, hydroxyl, formyl, mercapto, optionally substituted aryl, optionally substituted aralkyl, optionally substituted heteroaryl, optionally substituted heteroaralkyl, $-R^{12}-OR^{13}$, $-R^{12}-N(R^{14})R^{15}$, $-R^{12}-C(O)R^{13}-R^{12}-C(O)OR^{15}$, $-R^{12}-N(R^{14})C(O)R^{15}$, and $-R^{12}-S(O)_rR^{15}$;

each $R^5$ independently selected from the group consisting of halo, cyanato, thiocyanato, selenocyanato, trifluoromethoxy, azido, cyano, hydroxyl, formyl, mercapto, hydroxycarbonyl, optionally substituted alkyl, optionally substituted alkenyl, optionally substituted alkynyl, optionally substituted aryl, optionally substituted aralkyl, optionally substituted heteroaryl, optionally substituted cycloalkyl, optionally substituted heterocyclyl, $-OR^{20}$, $-S(O)_rR^{20}$, $-N(R^7)R^{20}$, $-N(R^9)S(O)_rR^{20}$, $-C(O)R^{20}$, and $-C(O)OR^{20}$;

$R^7$ represents H or optionally substituted alkyl;

each $R^9$ is independently H or optionally substituted alkyl;

$R^{12}$ represents a $C_1$-$C_6$ alkylene, $C_2$-$C_6$ alkenylene, $C_2$-$C_6$ alkynylene or $C_1$-$C_6$ alkyleneoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl, and where each t is independently 0 to 2.

6. The pharmaceutical composition of claim 2 wherein n is 0 to 2; p is 0 to 2; X is O, or $S(O)_r$ where r is 0 to 2;

$R^1$ is each independently selected from the group consisting of halo, cyanato, thiocyanato, selenocyanato, trifluoromethoxy, azido, cyano, nitro, hydroxyl, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^3$ is independently selected from the group consisting of hydrogen, halo, cyanato, thiocyanato, selenocyanato, trifluoromethoxy, azido, nitro, hydroxyl, formyl, mercapto, alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;

$R^4$ selected from the group consisting of cyanato, thiocyanato, selenocyanato, trifluoromethoxy, azido, cyano, nitro, hydroxyl, formyl, mercapto, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl, optionally substituted heterocyclylalkyl, $-R^{12}-OR^{13}$, $-R^{12}-N(R^{14})R^{15}$, $-R^{12}-C(O)R^{13}$, $-R^{12}-C(O)OR^{15}$, $-R^{12}-N(R^{14})C(O)R^{15}$, $-R^{12}-N(R^{14})C(O)OR^{15}$, $-R^{12}-S(O)_rR^{15}$ and $-R^{12}-S(O)_tN(R^{14})R^{15}$;

each $R^5$ independently selected from the group consisting of halo, cyano, hydroxyl, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, $-OR^{20}$, $-S(O)_rR^{20}$, $-N(R^7)R^{20}$, $-C(O)R^{20}$, and $-C(O)OR^{20}$;

$R^7$ represents H or optionally substituted alkyl;

each $R^9$ is independently H or optionally substituted alkyl;

$R^{12}$ represents a $C_1$-$C_6$ alkylene, $C_2$-$C_6$ alkenylene, $C_2$-$C_6$ alkynylene, or $C_1$-$C_6$ alkyleneoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl and $R^{20}$ represents optionally substituted alkyl, optionally substituted aryl, optionally substituted aralkyl or optionally substituted heterocyclyl, and where each t is independently 0 to 2.

7. The pharmaceutical composition of claim 2 wherein n is 0 or 1; p is 1 to 2; X is $S(O)_r$, where r is 0;

$R^1$ is each independently selected from the group consisting of halo, cyanato, thiocyanato, selenocyanato, trifluoromethoxy, azido, cyano, nitro, hydroxyl, hydroxycarbonyl, optionally substituted alkyl, alkoxy, and aminoalkyl;

$R^3$ is independently selected from the group consisting of hydrogen, halo, cyanato, thiocyanato, selenocyanato, trifluoromethoxy, azido, nitro, hydroxyl, formyl, mercapto, lower alkyl, optionally substituted lower alkenyl, optionally substituted lower alkynyl, lower alkoxy, lower aminoalkyl;

$R^4$ selected from the group consisting of cyanato, thiocyanato, selenocyanato, trifluoromethoxy, azido, cyano, nitro, hydroxyl, formyl, mercapto, optionally substituted aryl, optionally substituted aralkyl, optionally substituted heteroaryl, optionally substituted heteroaralkyl, —$R^{12}$—$OR^{13}$, —$R^{12}$—$N(R^{14})R^{15}$, —$R^{12}$—$C(O)R^{13}$, —$R^{12}$—$C(O)OR^{15}$, —$R^{12}$—$N(R^{14})C(O)R^{15}$, —$R^{12}$—$S(O)_tR^{15}$;

each $R^5$ independently selected from the group consisting of halo, cyano, nitro, hydroxyl, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, —$OR^{20}$, —$S(O)_tR^{20}$, —$N(R^7)R^{20}$, —$C(O)R^{20}$, and —$C(O)OR^{20}$;

$R^7$ represents H or optionally substituted alkyl;

each $R^9$ is independently H or optionally substituted alkyl;

$R^{12}$ represents a $C_1$-$C_6$ alkylene, $C_2$-$C_6$ alkenylene, $C_2$-$C_6$ alkynylene, or $C_1$-$C_6$ alkyleneoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl, and where each t is independently 0 to 2.

8. The pharmaceutical composition of claim 2 wherein n is 0 or 1; p is 1 to 2; X is O;

$R^1$ is each independently selected from the group consisting of halo, cyanato, thiocyanato, selenocyanato, trifluoromethoxy, azido, cyano, nitro, hydroxyl, hydroxycarbonyl, optionally substituted alkyl, alkoxy, and aminoalkyl;

$R^3$ is independently selected from the group consisting of hydrogen, halo, cyanato, thiocyanato, selenocyanato, trifluoromethoxy, azido, nitro, hydroxyl, formyl, mercapto, lower alkyl, optionally substituted lower alkenyl, optionally substituted lower alkynyl, alkoxy, and lower aminoalkyl;

$R^4$ selected from the group consisting of cyanato, thiocyanato, selenocyanato, trifluoromethoxy, azido, cyano, nitro, hydroxyl, formyl, mercapto, optionally substituted aryl, optionally substituted aralkyl, optionally substituted heteroaryl, optionally substituted heteroaralkyl, —$R^{12}$—$OR^{13}$, —$R^{12}$—$N(R^{14})R^{15}$, —$R^{12}$—$C(O)R^{13}$, —$R^{12}$—$C(O)OR^{15}$, —$R^{12}$—$N(R^{14})C(O)R^{15}$, and —$R^{12}$—$S(O)_tR^{15}$;

each $R^5$ independently selected from the group consisting of halo, cyano, hydroxyl, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, —$OR^{20}$, —$S(O)_tR^{20}$, —$N(R^7)R^{20}$, —$C(O)R^{20}$, and —$C(O)OR^{20}$;

$R^7$ represents H or optionally substituted alkyl;

each $R^9$ is independently H or optionally substituted alkyl;

$R^{12}$ represents a $C_1$-$C_6$ alkylene, $C_2$-$C_6$ alkenylene, $C_2$-$C_6$ alkynylene, or $C_1$-$C_6$ alkyleneoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl and $R^{20}$ represents optionally substituted alkyl, optionally substituted aryl, optionally substituted aralkyl or optionally substituted heterocyclyl, and where each t is independently 0 to 2.

9. The pharmaceutical composition of claim 2 wherein n is 0 or 1; p is 1 to 2; X is $S(O)_r$ where r is 2;

$R^1$ is each independently selected from the group consisting of halo, cyanato, thiocyanato, selenocyanato, trifluoromethoxy, azido, cyano, nitro, hydroxyl, hydroxycarbonyl, optionally substituted alkyl, alkoxy, and aminoalkyl;

$R^3$ is independently selected from the group consisting of hydrogen, halo, cyanato, thiocyanato, selenocyanato, trifluoromethoxy, azido, nitro, hydroxyl, formyl, mercapto, lower alkyl, optionally substituted lower alkenyl, optionally substituted lower alkynyl, lower alkoxy, and lower aminoalkyl;

$R^4$ selected from the group consisting of cyanato, thiocyanato, selenocyanato, trifluoromethoxy, azido, cyano, nitro, hydroxyl, formyl, mercapto, optionally substituted aryl, optionally substituted aralkyl, optionally substituted heteroaryl, optionally substituted heteroaralkyl, —$R^{12}$—$OR^{13}$, —$R^{12}$—$N(R^{14})R^{15}$, —$R^{12}$—$C(O)R^{13}$, —$R^{12}$—$C(O)OR^{15}$, —$R^{12}$—$N(R^{14})C(O)R^{15}$, and —$R^{12}$—$S(O)_tR^{15}$;

each $R^5$ independently selected from the group consisting of halo, cyano, hydroxyl, formyl, hydroxycarbonyl, optionally substituted alkyl, optionally substituted aryl, optionally substituted aralkyl, optionally substituted heteroaryl, optionally substituted cycloalkyl, optionally substituted heterocyclyl, —$OR^{20}$, —$S(O)_tR^{20}$, —$N(R^7)R^{20}$, —$C(O)R^{20}$, and —$C(O)OR^{20}$;

$R^7$ represents H or optionally substituted alkyl;

each $R^9$ is independently H or optionally substituted alkyl;

$R^{12}$ represents a $C_1$-$C_6$ alkylene, $C_2$-$C_6$ alkenylene, $C_2$-$C_6$ alkynylene, or $C_1$-$C_6$ alkyleneoxy;

$R^{13}$ represents optionally substituted alkyl, optionally substituted aryl, optionally substituted aralkyl or optionally substituted heterocyclyl;

$R^{14}$ represents H or optionally substituted alkyl;

$R^{15}$ represents optionally substituted alkyl, optionally substituted aryl, optionally substituted aralkyl or optionally substituted heterocyclyl;

$R^{20}$ represents optionally substituted alkyl, optionally substituted aryl, optionally substituted aralkyl or optionally substituted heterocyclyl, and where each t is independently 0 to 2.

10. The pharmaceutical composition of claim 1 wherein each t is independently 0 or 2.

11. The pharmaceutical composition of claim 1 wherein the optional substituents are independently $Q^1$, wherein $Q^1$ represents alkyl, alkoxy, aminoalkyl, haloalkyl, cycloalkyl, cycloalkylalkyl, heterocyclylalkyl, aryl, aralkyl, heteroaryl, heteroaralkyl, cyano, halo, hydroxyl, hydroxycarbonyl cyanato, thiocyanato, selenocyanato, trifluoromethoxy or azido.

12. A pharmaceutical composition comprising a pharmaceutically acceptable excipient and a compound selected from the group consisting of:
4-(4-nitrophenoxy)-2,6-diphenylpyrimidine;
2-(4-bromophenyl)-4-phenoxy-6-phenylpyrimidine;
2,4-diphenyl-6-(4-propylphenoxy)pyrimidine;
4-(2,6-diphenylpyrimidin-4-yloxy)benzaldehyde;
4-(2,6-diphenylpyrimidin-4-yloxy)benzonitrile;
4-phenoxy-2,6-diphenylpyrimidine;
4-(2-(4-bromophenyl)-6-phenylpyrimidin-4-yloxy)benzonitrile;

2-(4-bromophenyl)-4-methyl-6-phenoxypyrimidine;
4-(biphenyl-4-yloxy)-2-(4-bromophenyl)-6-phenylpyrimidine;
4-(4-butylphenoxy)-2,6-diphenylpyrimidine;
4-(biphenyl-4-yloxy)-2-(4-bromophenyl)-6-methylpyrimidine;
1-(4-(2-(4-bromophenyl)-6-methylpyrimidin-4-yloxy)phenyl)ethanone;
2-(4-(biphenyl-4-yloxy)-6-methylpyrimidin-2-yl)phenol;
2-(4-bromophenyl)-4-methyl-6-(4-nitrophenoxy)pyrimidine;
2-(4-bromophenyl)-4-methyl-6-(4-propylphenoxy)pyrimidine;
4-((4-chlorophenylthio)methyl)-2-phenyl-6-(phenylthio)pyrimidine;
4-(4-chlorophenylthio)-6-((4-chlorophenylthio)methyl)-2-phenylpyrimidine;
2-phenyl-4-(phenylsulfonylmethyl)-6-(phenylthio)pyrimidine;
4-phenoxy-2-phenyl-6-(phenylsulfonylmethyl)pyrimidine;
4-(4-chlorophenylthio)-2-phenyl-6-(phenylsulfonylmethyl)pyrimidine;
4-((4-chlorophenylsulfinyl)methyl)-6-phenoxy-2-phenylpyrimidine;
4-((4-chlorophenylsulfinyl)methyl)-6-(4-chlorophenylthio)-2-phenylpyrimidine;
2-phenyl-4-(phenylsulfinylmethyl)-6-(phenylthio)pyrimidine;
4-phenoxy-2-phenyl-6-(phenylsulfonylmethyl)pyrimidine;
4-phenoxy-2-phenyl-6-(phenylsulfinylmethyl)pyrimidine;
4-(methylthiomethyl)-2-phenyl-6-(phenylthio)pyrimidine;
4-(methylthiomethyl)-2-phenyl-6-(3-(trifluoromethyl)phenylthio)pyrimidine;
4-(methylthiomethyl)-6-phenoxy-2-phenylpyrimidine;
4-(4-chlorophenylthio)-6-(methylsulfonylmethyl)-2-phenylpyrimidine;
methyl 2-(6-(methylsulfonylmethyl)-2-phenylpyrimidin-4-ylthio)benzoate;
4-(2,3-dichlorophenylthio)-6-(methoxymethyl)-2-phenylpyrimidine;
4-(2,6-dichlorophenylthio)-6-(methoxymethyl)-2-phenylpyrimidine;
4-(2,4-dichlorophenylthio)-6-(methoxymethyl)-2-phenylpyrimidine;
4-(4-bromophenylthio)-6-(methoxymethyl)-2-phenylpyrimidine;
4-(methoxymethyl)-6-(4-methoxyphenylthio)-2-phenylpyrimidine;
4-(4-bromophenylthio)-2-phenyl-6-(phenylthiomethyl)pyrimidine;
4-(4-chlorophenylthio)-6-(methoxymethyl)-2-phenylpyrimidine;
4-((4-chlorophenylthio)methyl)-2-phenyl-6-(p-tolylthio)pyrimidine;
4-((4-chlorophenylthio)methyl)-6-(2,6-dichlorophenylthio)-2-phenylpyrimidine;
4-(3-chlorophenylthio)-6-((4-chlorophenylthio)methyl)-2-phenylpyrimidine;
4-((4-chlorophenylthio)methyl)-6-(2,4-dichlorophenylthio)-2-phenylpyrimidine;
4-((4-chlorophenylthio)methyl)-6-(4-methoxyphenylthio)-2-phenylpyrimidine;
4-(4-chlorophenylthio)-6-((4-chlorophenylthio)methyl)-2-phenylpyrimidine;
4-((4-chlorophenylthio)methyl)-6-(4-fluorophenylthio)-2-phenylpyrimidine;
4-(4-bromophenylthio)-6-(methylsulfonylmethyl)-2-phenylpyrimidine;
methyl 4-(2,6-diphenylpyrimidin-4-yloxy)benzoate;
methyl 4-(2-(4-bromophenyl)-6-methylpyrimidin-4-yloxy)benzoate;
4-(2-(2-hydroxyphenyl)-6-methylpyrimidin-4-yloxy)benzoic acid; and
4-(biphenyl-4-yloxy)-6-methyl-2-phenylpyrimidine.

13. A pharmaceutical composition comprising the composition of claim 1 and an additional therapeutically active compound.

14. The pharmaceutical composition of claim 13, wherein said additional therapeutically active compound is selected from levodopa (L-dihydroxyphenylalanine), L-aromatic amino acid decarboxylase (AADC) inhibitors and catechol O-methyl transferase (COMT) inhibitors.

15. The pharmaceutical composition of claim 13, wherein said additional therapeutically active compound is selected from an anti-inflammatory compound.

16. The pharmaceutical composition of claim 15, wherein said anti-inflammatory compound is selected from a matrix metalloproteinase inhibitor, an inhibitor of pro-inflammatory cytokines, non-steroidal anti-inflammatory drugs (NSAIDs), prostaglandin synthase inhibitors, cyclooxygenase-1 (COX-1) or cyclooxygenase-2 (COX-2) inhibitors, or corticosteroids.

17. The pharmaceutical composition of claim 13, wherein said additional therapeutically active compound is selected from an antihyperlipidemic agent; a plasma high-density lipoprotein (HDL)-raising agent; an antihypercholesterolemic agent; an acyl-coenzyme A cholesterol acyltransferase (ACAT) inhibitor; probucol; nicotinic acid and the salts thereof and niacinamide; a cholesterol absorption inhibitor; a bile acid sequestrant anion exchange resin; an LDL (low density lipoprotein) receptor inducer; ciofibrate; bezafibrate; fenofibrate; gemfibrizo; vitamin $B_6$ (pyridoxine) and the pharmaceutically acceptable salts thereof; vitamin $B_{12}$ (cyanocobalamin); vitamin $B_3$; anti-oxidant vitamins; a beta-blocker; liver X receptor (LXR) α or β agonists, antagonists, or partial agonists, farnesoid X receptor (FXR) agonists, antagonists, or partial agonists, an angiotensin II antagonist; an angiotensin converting enzyme inhibitor; and a platelet aggregation inhibitor and aspirin.

18. The pharmaceutical composition of claim 13, wherein said additional therapeutically active compound comprises parathyroid hormone (PTH) or human parathyroid hormone fragment (hPTHF) 1-34.

19. A pharmaceutical composition comprising a compound selected from the group consisting of:

4-(6-methyl-2-phenylpyrimidin-4-ylamino)benzoic acid;

4-(5-allyl-6-methyl-2-phenylpyrimidin-4-ylamino)benzoic acid; and 3-(6-methyl-2-phenylpyrimidin-4-ylamino)benzoic acid; and a pharmaceutically acceptable excipient.

20. A pharmaceutical composition comprising a compound of formula (I)

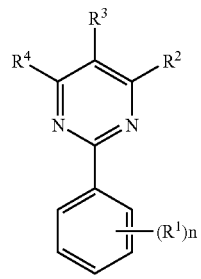

or a pharmaceutical acceptable salt thereof, wherein
n is 0 to 5;
$R^1$ is each independently selected from the group consisting of halo, cyanato, thiocyanato, selenocyanato, trifluoromethoxy, azido, cyano, nitro, hydroxyl, formyl, mercapto, hydroxycarbonyl, optionally substituted alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl;
$R^2$ is selected from the group consisting of optionally substituted cycloalkyl, optionally substituted aralkyl, $-OR^6$, $-S(O)R^6$, $-S(O)_2R^6$, $-N(R^9)S(O)_tR^{10}$, $-C(O)R^6$, $-C(O)OR^6$, and $-C(O)N(R^7)R^8$;
$R^3$ is independently selected from the group consisting of hydrogen, halo, cyanato, thiocyanato, selenocyanato, trifluoromethoxy, azido, nitro, hydroxyl, mercapto, alkyl, optionally substituted alkenyl, optionally substituted alkynyl, alkoxy, aminoalkyl, optionally substituted aryl, optionally substituted heteroaryl, optionally substituted cycloalkyl, and optionally substituted heterocyclyl; and
$R^4$ selected from the group consisting of cyanato, thiocyanato, selenocyanato, trifluoromethoxy, azido, cyano, nitro, hydroxyl, formyl, mercapto, optionally substituted cycloalkyl, optionally substituted cycloalkylalkyl, optionally substituted aryl, optionally substituted aralkyl, optionally substituted heterocyclyl, optionally substituted heteroaryl, optionally substituted heteroaralkyl, optionally substituted heterocyclylalkyl, $-R^{12}-OR^{13}$, $-R^{12}-N(R^{14})R^{15}$, $-R^{12}-C(O)R^{13}$, $-R^{12}-C(O)OR^{15}$, $R^{12}-N(R^{14})C(O)R^{15}$, $-R^{12}-N(R^{14})C(O)OR^{15}$, $-R^{12}-S(O)_tR^{15}$ and $-R^{12}-S(O)_tN(R^{14})R^{15}$;

$R^6$ represents substituted alkyl, optionally substituted aryl, optionally substituted aralkyl or optionally substituted heterocyclyl;
$R^7$ represents H or optionally substituted alkyl;
$R^8$ represents optionally substituted alkyl, optionally substituted aryl, optionally substituted aralkyl or optionally substituted heterocyclyl;
$R^9$ represents H or optionally substituted alkyl;
$R^{10}$ represents optionally substituted alkyl, optionally substituted aryl, optionally substituted aralkyl or optionally substituted heterocyclyl;
$R^{12}$ represents a $C_1$-$C_6$ alkylene, $C_2$-$C_6$ alkenylene, $C_2$-$C_6$ alkynylene or $C_1$-$C_6$ alkyleneoxy;
$R^{13}$ represents optionally substituted alkyl, optionally substituted aryl, optionally substituted aralkyl or optionally substituted heterocyclyl;
$R^{14}$ represents H or optionally substituted alkyl;
$R^{15}$ represents optionally substituted alkyl, optionally substituted aryl, optionally substituted aralkyl or optionally substituted heterocyclyl, and where each t is independently 0 to 2,
wherein the optional substituents are independently $Q^1$, where $Q^1$ represents alkyl, haloalkyl, cycloalkyl, cycloalkylalkyl, heterocyclylalkyl, aryl, aralkyl, heteroaryl, heteroaralkyl, cyano, halo, hydroxyl, hydroxycarbonyl, cyanato, thiocyanato, selenocyanato, trifluoromethoxy, azido, $-R^{30}-OR^{31}$, $-R^{30}-SR^{16}$, $-R^{30}-N(R^{32})(R^{33})$, $-R^{30}-C(J)R^{34}$, $-R^{30}-C(J)OR^{31}$, $-R^{30}-C(J)N(R^{31})N(R^{32})(R^{33})$, $-R^{30}-N(R^{31})C(J)R^{34}$, $-R^{30}-N(R^{31})C(J)OR^{31}$, $-R^{30}-N(R^{31})C(J)N(R^{32})(R^{33})$, $-R^{30}-OC(J)R^{34}$, $-R^{30}-OC(J)OR^{31}$, $-R^{30}-OC(J)N(R^{32})(R^{33})$, $-Si(R^{35})_3$, $-N(R^{31})S(O)_yR^{36}$ or $-R^{30}-S(O)_yR^{36}$;
where each $R^{30}$ is independently a direct bond or a straight or branched alkylene chain;
$R^{31}$ and $R^{34}$ are each independently hydrogen, alkyl, alkenyl, alkynyl, haloalkyl, cycloalkyl, cycloalkylalkyl, heterocyclylalkyl, aryl, aralkyl, heteroaryl or heteroaralkyl;
$R^{32}$ and $R^{33}$ are each independently hydrogen, alkyl, alkenyl, alkynyl, haloalkyl, cycloalkyl, cycloalkylalkyl, heterocyclyl, aryl, aralkyl, heteroaryl or heteroaralkyl;
or $R^{32}$ and $R^{33}$ together with the nitrogen atom to which they are attached, from a heterocyclylalkenyl, or heteroaryl;
$R^{35}$ $R^{36}$ and $R^{16}$ are each independently alkyl, alkenyl, alkynyl, haloalkyl, cycloalkyl, cycloalkylalkyl, heterocyclyl, heterocyclylalkyl, aryl, aralkyl, heteroaryl or heteroaralkyl;
each J is independently O or S; and each y is independently 0 to 2;
and a pharmaceutically acceptable excipient.

* * * * *